United States Patent
Hashiro et al.

(10) Patent No.: US 11,884,951 B2
(45) Date of Patent: *Jan. 30, 2024

(54) METHOD FOR PRODUCING RNA

(71) Applicant: AJINOMOTO CO., INC., Tokyo (JP)

(72) Inventors: Shuhei Hashiro, Kanagawa (JP); Hisashi Yasueda, Kanagawa (JP); Mayu Mitsuhashi, Kanagawa (JP); Sergei Vladimirovich Mashko, Moscow (RU); Aleksandr Aleksandrovich Krylov, Moscow (RU); Yuliya Sergeevna Lobanova, Moscow (RU)

(73) Assignee: AJINOMOTO CO., INC., Tokyo (JP)

(*) Notice: Subject to any disclaimer, the term of this patent is extended or adjusted under 35 U.S.C. 154(b) by 256 days.

This patent is subject to a terminal disclaimer.

(21) Appl. No.: 17/326,677

(22) Filed: May 21, 2021

(65) Prior Publication Data

US 2021/0269840 A1 Sep. 2, 2021

Related U.S. Application Data

(63) Continuation of application No. 16/582,385, filed on Sep. 25, 2019, now Pat. No. 11,046,986, which is a continuation of application No. PCT/JP2018/003692, filed on Feb. 2, 2018.

(30) Foreign Application Priority Data

Mar. 28, 2017 (JP) ................... 2017-063777
Aug. 24, 2017 (RU) .......................... RU2017129988

(51) Int. Cl.
| | |
|---|---|
| C12P 19/34 | (2006.01) |
| C12N 15/10 | (2006.01) |
| C12N 15/77 | (2006.01) |
| C12N 1/20 | (2006.01) |
| C12R 1/13 | (2006.01) |
| C12R 1/05 | (2006.01) |

(52) U.S. Cl.
CPC .............. *C12P 19/34* (2013.01); *C12N 1/205* (2021.05); *C12N 15/1003* (2013.01); *C12N 15/77* (2013.01); *C12R 2001/05* (2021.05); *C12R 2001/13* (2021.05)

(58) Field of Classification Search
None
See application file for complete search history.

(56) References Cited

U.S. PATENT DOCUMENTS

| | | | |
|---|---|---|---|
| 3,880,738 A | | 4/1975 | Suzuki et al. |
| 11,046,986 B2* | | 6/2021 | Hashiro ............. C12N 15/1003 |
| 2002/0119449 A1 | | 8/2002 | Cheynet-Sauvion et al. |
| 2019/0093108 A1 | | 3/2019 | Killmer et al. |
| 2020/0024629 A1 | | 1/2020 | Hashiro et al. |

FOREIGN PATENT DOCUMENTS

| | | |
|---|---|---|
| WO | WO02/024904 A2 | 3/2002 |
| WO | WO02/024904 A3 | 3/2002 |
| WO | WO2009/063969 A1 | 5/2009 |
| WO | WO2010/084371 A1 | 7/2010 |
| WO | WO2014/151581 A1 | 9/2014 |
| WO | WO2014/151581 A9 | 12/2015 |
| WO | WO2014/151581 A9 | 1/2016 |
| WO | WO2017/025120 A1 | 2/2017 |
| WO | WO2017/160600 A1 | 9/2017 |

OTHER PUBLICATIONS

Ikeda et al. Appl. Microbiol Biotechnol 62:99-109 (Year: 2003).*
Yang et al. BMC Genomics 940, pp. 1-13 (Year: 2017).*
Office Action from Chinese Patent App. No. 201880021697.7 (dated Nov. 21, 2022) with English language translation thereof.
"Multispecies: ribonuclease 3 [Corynebacterium]", GenBank DataBase, Accession No. WP_003861938, retrieved from internet on Nov. 8, 2022, 1 pg.
Jin, X.-K., et al., "Two antibacterial C-type lectins from crustacean, *Eriocheir sinensis*, stimulated cellular encapsulation in vitro," Developmental and Comparative Immunology 2013;41:544-552.
"Bacteriophage BFK20 gene sequence, complete f1 promoter," GenBank DataBase, Accession No. L13772, retrieved from internet on Nov. 9, 2022, 1 pg.
Decision of Refusal from Japanese Patent App. No. 2019-554009 (dated Aug. 9, 2022) with English language translation.
Kikuchi, Y., et al., "Secretion of Active-Form Streptoverticillium mobaraense Transglutaminase by Corynebacterium glutamicum: Processing of the Pro-Transglutaminase by a Cosecreted Subtilisin-Like Protease from Streptomyces albogriseolus," Appl. Environmen. Microbiol. 2003;69(1):358-366.
Tenllado, F., et al., "Crude extracts of bacterially expressed dsRNA can be used to protect plants against virus infections," BMC Biotechnol. 2003;3(3), pp. 1-11.
Aalton, A. P., et al., "Large-scale production of dsRNA and siRNA pools for RNA interference utilizing bacteriophage φ6 RNA-dependent RNA polymerase," RNA 2007;13(3):422-429.
Ponchon, L., et al., "A generic protocol for the expression and purification of recombinant RNA in *Escherichia coli* using a tRNA scaffold," Nature Protocols 2009;4(6):947-959.

(Continued)

*Primary Examiner* — Brian Whiteman

(74) *Attorney, Agent, or Firm* — Cermak Nakajima & McGowan LLP; Shelly Guest Cermak

(57) ABSTRACT

A method for producing RNA is provided. Objective RNA is produced by culturing a coryneform bacterium having an expression unit for the objective RNA, which has been modified so that the activity of ribonuclease III is reduced, in a medium, to express the objective RNA and accumulate the objective RNA in cells of the bacterium, and collecting the objective RNA from the cells.

10 Claims, 24 Drawing Sheets

Specification includes a Sequence Listing.

(56) References Cited

OTHER PUBLICATIONS

Huang, L., et al., "Efficient and specific gene knockdown by small interfering RNAs produced in bacteria," Nature Biotechnol. 2013;31(4):350-356.
International Search Report and Written Opinion for PCT Patent App. No. PCT/JP2018/003692 (dated Apr. 30, 2018).
Maeda, T., et al., "Rnase III mediated cleavage of the coding region of mraZ mRNA is required for efficient cell division in Corynebacterium glutamicum," Molecular Microbiol. 2016;99(6):1149-1166.
Kortmann, M., et al., "A chromosomally encoded T7 RNA polymerase-dependent gene expression system for Corynebacterium glutamicum: construction and comparative evaluation at the single-cell level," Microbial Biotechnol. 2015;8:253-265.
Friehs, K., "Plasmid Copy Number and Plasmid Stability," Adv. Biochem. Engin./Biotechnol. 2004,86:47-82.
Fong, R., et al., "Characterization of a Large, Stable, High-Copy-Number Streptomyces Plasmid That Requires Stability and Transfer Functions for Heterologous Polyketide Overproduction," Environmental Microbiol. 2007;73(4):1296-1307.
Kurpiel, P. M., et al., "Point mutations in the inc antisense RNA gene are associated with increased plasmid copy number, expression of blaCMY-2 and resistance to piperacillin/tazobactam in Escherichia coli," J. Antimicrob. Chemother. 2012;67:339-345.
Couturier, E., et al., "Replication-associated gene dosage effects shape the genomes of fast-growing bacteria but only for transcription and translation genes," Molecular Microbiol. 2006;59(5):1506-1518.
Communication Pursuant to Rule 114(2) EPC from European Patent App. No. 18705998.5 (dated May 4, 2021).
Third Party Observation for European Patent App. No. 18705998.5 (Apr. 28, 2021).
Communication pursuant to Rule 114(2) EPC; Third Party Observations for Application No. 18705998.5, dated May 22, 2023.
Papic, L. et al., "Double-stranded RNA production and the kinetics of recombinant Escherichia coli HT115 in fed-batch culture," Biotechnology Reports 20, (2018), 4 pp.
Grabherr, R. et al., "Impact of targeted vector design on ColE1 plasmid replication," Trends in Biotechnology, vol. 20, No. 6, (2002), pp. 257-260.
Ahn, S-J. et al., "Microbial-Based Double-Stranded RNA Production to Develop Cost-Effective RNA Interference Application for Insect Pest Management," International Journal of Insect Science; vol. 11, (2019) pp. 1-8.

* cited by examiner

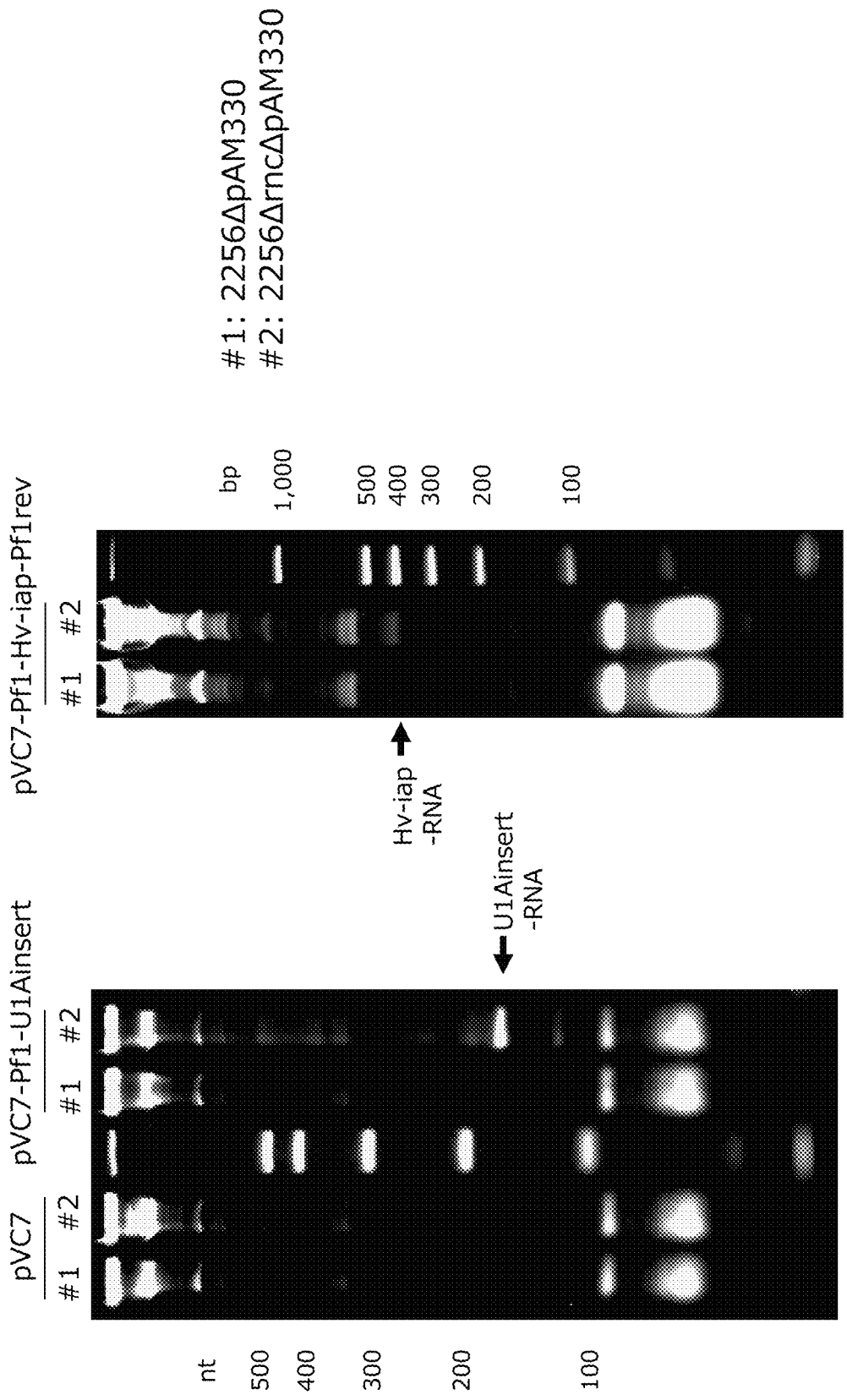

METHOD FOR PRODUCING RNA

This application is a Continuation of, and claims priority under 35 U.S.C. § 120 to, U.S. patent application Ser. No. 16/582,385, filed Sep. 25, 2019, which was a Continuation of, and claimed priority under 35 U.S.C. § 120 to, International Application No. PCT/JP2018/003692, filed Feb. 2, 2018 and claimed priority therethrough under 35 U.S.C. § 119 to Russian Patent Application 2017129988, filed Aug. 24, 2017 and Japanese Patent Application No. 2017-063777, filed Mar. 28, 2017, the entireties of which are incorporated by reference herein. Also, the Sequence Listing filed electronically herewith is hereby incorporated by reference (File name: 2021-05-21T_US-597C_Seq_List; File size: 23 KB; Date recorded: May 21, 2021).

BACKGROUND

Technical Field

The present invention relates to a method for producing RNA (ribonucleic acid) by fermentation using a microorganism.

Background Art

Methods for producing RNA by using a microorganism have been previously reported and include for example, a method of using *Escherichia coli* deficient in ribonuclease III (RNaseIII) as a host to accumulate RNA in bacterial cells (see Tenllado F, et. al., Crude extracts of bacterially expressed dsRNA can be used to protect plants against virus infections. BMC Biotechnol. 2003 Mar. 20; 3:3), a method of using *Pseudomonas syringae* as a host in combination with the function of phi 6 bacteriophage to accumulate RNA in capsids (see Aalto A P, et. al., Large-scale production of dsRNA and siRNA pools for RNA interference utilizing bacteriophage phi6 RNA-dependent RNA polymerase. RNA. 2007 March; 13(3):422-9), a method of using *Escherichia coli* as a host to accumulate RNA fused with a partial sequence of tRNA in bacterial cells (see Ponchon L, et. al., A generic protocol for the expression and purification of recombinant RNA in *Escherichia coli* using a tRNA scaffold. Nat Protoc. 2009; 4(6):947-59), a method of using *Escherichia coli* as a host to produce siRNA while allowing the siRNA to form a complex with a protein that binds to the siRNA (see Huang L, et. al., Efficient and specific gene knockdown by small interfering RNAs produced in bacteria. Nat Biotechnol. 2013 April; 31(4):350-6), a method of using a bacterium of the genus *Rhodovulum* as a host to produce RNA by secretory production (see WO2009/063969), and a method of using yeast as a host to accumulate RNA in yeast mitochondria (see WO2010/084371).

SUMMARY

It is an aspect of the present invention to provide a method for efficiently producing RNA.

It has been found that RNA can be efficiently produced by using a coryneform bacterium deficient in ribonuclease III (RNaseIII) as a host, and is described herein.

It is an aspect of the present invention to provide a method for producing objective RNA, the method comprising: culturing a coryneform bacterium having an expression unit for the objective RNA in a medium, to express the objective RNA and accumulate the objective RNA in cells of the bacterium; and collecting the objective RNA from the cells, wherein the bacterium has been modified so that the activity of ribonuclease III is reduced as compared with a non-modified strain.

It is a further aspect of the present invention to provide the method as described above, wherein the ribonuclease III is a protein selected from the group consisting of: (a) a protein comprising the amino acid sequence of SEQ ID NO: 52; (b) a protein comprising the amino acid sequence of SEQ ID NO: 52, but which includes substitution, deletion, insertion, and/or addition of 1 to 10 amino acid residues, and having ribonuclease III activity; and (c) a protein comprising an amino acid sequence having an identity of 90% or higher to the amino acid sequence of SEQ ID NO: 52, and having ribonuclease III activity.

It is a further aspect of the present invention to provide the method as described above, wherein the activity of ribonuclease III is reduced by attenuating the expression of a gene encoding ribonuclease III, or by disrupting the gene.

It is a further aspect of the present invention to provide the method as described above, wherein the activity of ribonuclease III is reduced by deletion of a gene encoding ribonuclease III.

It is a further aspect of the present invention to provide the method as described above, wherein the bacterium comprises 5 copies/cell or more of the expression unit.

It is a further aspect of the present invention to provide the method as described above, wherein the bacterium comprises 70 copies/cell or more of the expression unit.

It is a further aspect of the present invention to provide the method as described above, wherein the bacterium comprises a vector containing the expression unit.

It is a further aspect of the present invention to provide the method as described above, wherein the expression unit comprises a promoter sequence that functions in the coryneform bacterium and a nucleotide sequence encoding the objective RNA in the direction from 5' to 3'.

It is a further aspect of the present invention to provide the method as described above, wherein the promoter sequence is derived from a phage.

It is a further aspect of the present invention to provide the method as described above, wherein the promoter sequence is F1 promoter or T7 promoter.

It is a further aspect of the present invention to provide the method as described above, wherein the promoter sequence is a promoter selected from the group consisting of: (a) a promoter comprising the nucleotide sequence of SEQ ID NO: 13 or 78; and (b) a promoter comprising a nucleotide sequence having an identity of 90% or higher to the nucleotide sequence of SEQ ID NO: 13 or 78.

It is a further aspect of the present invention to provide the method as described above, wherein the bacterium is a bacterium belonging to the genus *Corynebacterium*.

It is a further aspect of the present invention to provide the method as described above, wherein the bacterium is *Corynebacterium glutamicum*.

BRIEF DESCRIPTION OF DRAWINGS

FIG. 6 shows agarose gel electrophoretograms (photographs) showing an improved effect in RNA production due to deletion of the rnc gene.

DETAILED DESCRIPTION

Figure 1:
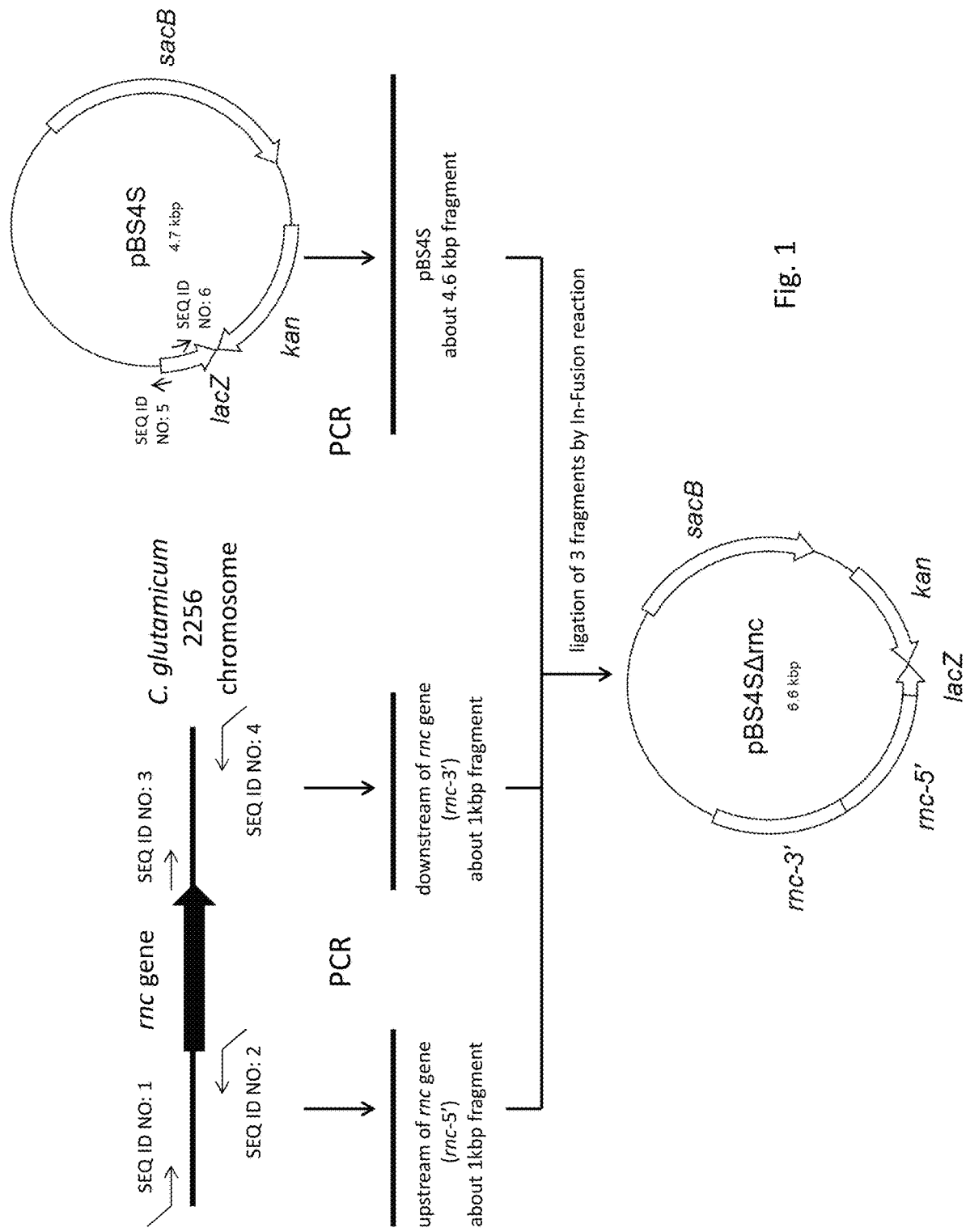
FIG. 1 shows a diagram of the construction scheme of plasmid pPBS4SΔrnc.

The method as described herein is a method for producing objective RNA by culturing a coryneform bacterium having an expression unit for the objective RNA in a medium, and collecting the transcribed objective RNA, wherein the bacterium has been modified so that the activity of ribonuclease III is reduced. The coryneform bacterium used for this method can also be referred to as "bacterium" or "bacterium as described herein".

<1> Bacterium as Described Herein

The bacterium is a coryneform bacterium having an expression unit for objective RNA, which has been modified so that the activity of ribonuclease III is reduced.

The bacterium can be obtained by introducing the expression unit for the objective RNA and reducing the activity of ribonuclease III in a coryneform bacterium. Modifications for constructing the bacterium can be performed in an arbitrary order. That is, the bacterium can be obtained by, for example, introducing the expression unit for the objective RNA to a coryneform bacterium, and then modifying the coryneform bacterium so that the activity of ribonuclease III is reduced. The bacterium can also be obtained by, for example, modifying a coryneform bacterium so that the activity of ribonuclease III is reduced, and then introducing the expression unit for the objective RNA to the coryneform bacterium. The bacterium or a bacterium from which the bacterium is constructed can also be referred to as "host".

The bacterium has an ability to produce the objective RNA (objective RNA-producing ability). Specifically, the bacterium has the objective RNA-producing ability at least because the bacterium has the expression unit for the objective RNA. The bacterium may be, for example, a bacterium that has acquired the objective RNA-producing ability due to introduction of the expression unit for the objective RNA, or due to a combination of introduction of the expression unit for the objective RNA and reduction in the activity of ribonuclease III. That is, a strain to be used for constructing the bacterium and before being modified so that the activity of ribonuclease III is reduced may or may not be able to produce the objective RNA, on the assumption that the strain has the expression unit for the objective RNA.

The bacterium may have any characteristics so long as the bacterium has the objective RNA-producing ability. For example, the bacterium may or may not have a vector such as plasmid, other than a vector containing the expression unit for the objective RNA. That is, for example, when the bacterium inherently has a plasmid, the plasmid may be cured (removed).

<1-1> Bacterium Having Objective RNA-Producing Ability

The phrase "bacterium having an objective RNA-producing ability" refers to a bacterium having an ability to express and accumulate the objective RNA in cells of the bacterium to such a degree that the objective RNA can be collected, when the bacterium is cultured in a medium. The bacterium having the objective RNA-producing ability may be a bacterium that is able to accumulate the objective RNA in cells of the bacterium in an amount larger than that obtainable with a non-modified strain. The term "non-modified strain" refers to a control strain that has not been modified so that the activity of ribonuclease III is reduced. That is, examples of the non-modified strain include a wild-type strain and parental strain. The bacterium having the objective RNA-producing ability may also be a bacterium that is able to accumulate the objective RNA in cells of the bacterium in an amount of 1 mg/L-culture or more, 2 mg/L-culture or more, 5 mg/L-culture or more, 10 mg/L-culture or more, 20 mg/L-culture or more, 50 mg/L-culture or more, or 100 mg/L-culture or more.

A coryneform bacterium can be used as a host. Examples of the coryneform bacterium include bacteria belonging to the genus *Corynebacterium*, *Brevibacterium*, *Mycobacterium*, *Microbacterium*, or the like.

Specific examples of the coryneform bacteria include the following species:

*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*

*Corynebacterium melassecola*
*Corynebacterium thermoaminogenes (Corynebacterium efficiens)*
*Corynebacterium herculis*
*Brevibacterium divaricatum (Corynebacterium glutamicum)*
*Brevibacterium flavum (Corynebacterium glutamicum)*
*Brevibacterium immariophilum*
*Brevibacterium lactofermentum (Corynebacterium glutamicum)*
*Brevibacterium roseum*
*Brevibacterium saccharolyticum*
*Brevibacterium thiogenitalis*
*Corynebacterium ammoniagenes (Corynebacterium stationis)*
*Brevibacterium album*
*Brevibacterium cerinum*
*Microbacterium ammoniaphilum*

Specific examples of the coryneform bacteria include the following strains:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium efficiens (Corynebacterium thermoaminogenes)* AJ12340 (FERM BP-1539)
*Corynebacterium herculis* ATCC 13868
*Brevibacterium divaricatum (Corynebacterium glutamicum)* ATCC 14020
*Brevibacterium flavum (Corynebacterium glutamicum)* ATCC 13826, ATCC 14067, AJ12418 (FERM BP-2205)
*Brevibacterium immariophilum* ATCC 14068
*Brevibacterium lactofermentum (Corynebacterium glutamicum)* ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes (Corynebacterium stationis)* ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria include bacteria that had previously been classified into the genus *Brevibacterium*, but are presently united into the genus *Corynebacterium* (Int. J. Syst. Bacteriol., 41, 255 (1991)). Moreover, *Corynebacterium stationis* includes bacteria that had previously been classified as *Corynebacterium ammoniagenes*, but are presently re-classified into *Corynebacterium stationis* on the basis of nucleotide sequence analysis of 16S rRNA etc. (Int. J. Syst. Evol. Microbiol., 60, 874-879 (2010)).

These strains are available from, for example, the American Type Culture Collection (Address: 10801 University Boulevard, Manassas, Va. 20110 United States of America). That is, registration numbers are given to the respective strains, and the strains can be ordered by using these registration numbers (refer to atcc.org). The registration numbers of the strains are listed in the catalogue of the American Type Culture Collection. These strains can also be obtained from, for example, the depositories at which the strains were deposited.

<1-2> Introduction of Expression Unit for Objective RNA

The bacterium has the expression unit for the objective RNA. A coryneform bacterium having the expression unit for the objective RNA can be obtained by introducing the expression unit for the objective RNA to a coryneform bacterium.

The term "objective RNA" refers to RNA to be produced according to the method as described herein. One kind of objective RNA may be produced, or two or more kinds of objective RNAs may be produced.

The objective RNA is not particularly limited so long as it is RNA exogenous to the host, that is, so long as it is RNA other than the RNAs native to the host. The objective RNA can be appropriately selected according to various conditions such as the purpose of use of the objective RNA. The objective RNA may be, for example, naturally existing RNA, modified RNA thereof, or artificially designed RNA. The objective RNA may be, for example, RNA derived from a microorganism, RNA derived from a plant, RNA derived from an animal, or RNA derived from a virus. The term "derived from" means "native to". The objective RNA may be, for example, mRNA (messenger RNA), or non-coding RNA such as rRNA (ribosomal RNA), tRNA (transfer RNA), miRNA (micro RNA), siRNA (small interfering RNA), ribozyme, and RNA aptamer. The mRNA may be, for example, one encoding a protein having some function such as enzyme, receptor, transporter, antibody, structural protein, and regulator, or one encoding a protein having no function per se. Incidentally, the term "protein" includes so-called peptides such as oligopeptide and polypeptide. The objective RNA may be, for example, RNA having any of the nucleotide sequences of such RNAs as mentioned above. The objective RNA may also be, for example, RNA having a partial sequence of any of the nucleotide sequences of such RNAs as mentioned above. The objective RNA may also be, for example, RNA having a complementary sequence of any of the nucleotide sequences of such RNAs as mentioned above or partial sequences thereof. The objective RNA may also be, for example, RNA having a variant sequence of any of the nucleotide sequences of such RNAs as mentioned above, partial sequences thereof, or complementary sequences thereof. The descriptions concerning variants of the ribonuclease III gene mentioned later can be similarly applied to such a variant sequence. The objective RNA may also have, for example, a combination of two or more nucleotide sequences selected from the nucleotide sequences of such RNAs as mentioned above, partial sequences thereof, complementary sequences thereof, and variant sequences thereof. Specific examples of the objective RNA include a partial sequence of mRNA of inhibitor of apoptosis protein of *Henosepilachna vigintioctopunctata*, and a partial sequence of mRNA of subunits A and E constituting ATPase in a vacuole of Colorado potato beetle (*Leptinotarsa decemlineata*).

The objective RNA may be, for example, single-stranded RNA (RNA having one molecule of RNA chain), or double-stranded RNA (RNA having two molecules of RNA chain). The double-stranded RNA may be a double strand having a single kind of RNA molecule (homo-double strand), or a double strand having two different kinds of RNA molecules (hetero-double strand). Specific examples of the double-stranded RNA include, for example, double-stranded RNA having an RNA strand and a complementary strand thereof. The objective RNA may also be, for example, a double strand having one molecule of RNA chain and one molecule of DNA chain. The objective RNA may contain both a single-stranded region and a double-stranded region. That is, for example, the single-stranded RNA may partially form a double-stranded structure, such as stem-loop structure, within a molecule. Also, for example, the double-stranded RNA may partially contain a single-stranded structure.

The length of the objective RNA is not particularly limited. The length of the objective RNA, for example, may be 10 residues or more, 20 residues or more, 50 residues or more, or 100 residues or more, or may be 10000 residues or less, 5000 residues or less, 2000 residues or less, 1000 residues or less, or 500 residues or less, or may be a range defined as a combination thereof.

The term "expression unit for objective RNA" refers to a genetic construct configured so that the objective RNA can be expressed therefrom. The expression unit for the objective RNA contains a promoter sequence that functions in a coryneform bacterium and a nucleotide sequence encoding the objective RNA in the direction from 5' to 3'. The promoter sequence is also simply referred to as "promoter". The nucleotide sequence encoding the objective RNA is also referred to as "gene encoding objective RNA" or "objective RNA gene". It is sufficient that the objective RNA gene is ligated downstream of a promoter so that the objective RNA is expressed under control of the promoter. The expression unit for the objective RNA may also contain regulator sequence(s) effective for expressing the objective RNA in a coryneform bacterium, such as operator and terminator, at appropriate position(s) so that the regulator sequence(s) can function. Incidentally, the phrases "expression of an objective RNA gene", "transcription of an objective RNA gene", "expression of objective RNA", and "transcription of objective RNA" may be used synonymously with each other. The expression unit for the objective RNA can be appropriately designed according to various conditions such as the type and transcription pattern of the objective RNA.

The transcription pattern of the objective RNA is not particularly limited so long as the objective RNA is obtained. The objective RNA gene may be transcribed, for example, in one direction, that is, by using either one strand of a double strand as the template, or in both directions, that is, by using both strands of a double strand as the template. Transcription of the objective RNA gene in both directions can be performed by transcribing the gene from promoters arranged interposing the gene in mutually opposite directions, that is, promoters arranged at 5'-side of the gene in the respective strands of a double strand. That is, the expression unit for the objective RNA may contain such two promoters. In such a case, the two promoters may or may not be identical to each other. By transcribing the objective RNA gene in one direction, there can be typically obtained single-stranded RNA. By transcribing the objective RNA gene in both directions, there can be typically obtained double-stranded RNA. Double-stranded RNA can also be obtained by transcribing both strands of the double-stranded RNA from the respective expression units thereof.

The objective RNA gene can be obtained by, for example, cloning. For cloning, for example, nucleotides containing the objective RNA gene, such as genomic DNA and cDNA, can be used. The objective RNA gene can also be obtained by, for example, total synthesis on the basis of the nucleotide sequence thereof (Gene, 60(1), 115-127 (1987)). The obtained objective RNA gene can be used as it is, or after being modified as required. That is, a variant of the objective RNA gene may be obtained by modifying the gene. A gene can be modified by a known technique. For example, an objective mutation can be introduced into an objective site of DNA by the site-specific mutation method. Examples of the site-specific mutation method include the method of utilizing PCR (Higuchi, R., 61, in PCR Technology, Erlich, H. A. Eds., Stockton Press (1989); Carter, P., Meth. in Enzymol., 154, 382 (1987)), and the method of utilizing phage (Kramer, W. and Frits, H. J., Meth. in Enzymol., 154, 350 (1987); Kunkel, T. A. et al., Meth. in Enzymol., 154, 367 (1987)). Alternatively, a variant of the objective RNA gene may be totally synthesized. In addition, the expression unit for the objective RNA can be obtained by appropriately modifying the unit, such as introduction of a promoter sequence, to the obtained objective RNA gene. Incidentally, other elements constituting the expression unit for the objective RNA, such as a promoter sequence, or the whole of the expression unit for the objective RNA can be obtained in the same manner as the objective RNA gene.

The promoter for expressing the objective RNA gene is not particularly limited so long as it functions in the host. The phrase "promoter that functions in a host" refers to a promoter that shows a promoter activity, such as gene transcription activity, in the host. The promoter may be a promoter derived from the host, or a heterogenous promoter. The promoter may be the native promoter of the objective RNA gene, or a promoter of another gene. The promoter may be an inducible promoter or a constitutive promoter for gene expression.

Examples of the promoter include, for example, promoters of genes of the glycolytic pathway, pentose phosphate pathway, TCA cycle, amino acid biosynthesis systems, and cell surface layer proteins. As the promoter, a stronger promoter such as the following ones may also be used. Examples of the stronger promoter include, for example, the artificially modified P54-6 promoter (Appl. Microbiol. Biotechnol., 53, 674-679 (2000)); pta, aceA, aceB, adh, and amyE promoters inducible with acetic acid, ethanol, pyruvic acid, or the like; and cspB, SOD, and tuf promoters, which are potent promoters (Journal of Biotechnology, 104 (2003) 311-323; Appl. Environ. Microbiol., 2005 December; 71 (12):8587-96); as well as lac promoter, tac promoter, trc promoter, F1 promoter, T7 promoter, T5 promoter, T3 promoter, and SP6 promoter. Particular examples of the promoter include promoters derived from phages, such as F1 promoter, T7 promoter, T5 promoter, T3 promoter, and SP6 promoter. More particular examples of the promoter include F1 promoter and T7 promoter. The nucleotide sequence of the F1 promoter is shown as SEQ ID NO: 13. The nucleotide sequence of the T7 promoter is shown as SEQ ID NO: 78.

As the promoter, a highly-active type of an existing promoter may also be obtained and used by using various reporter genes. For example, by making the −35 and −10 regions in a promoter region closer to the consensus sequence, the activity of the promoter can be enhanced (WO00/18935). Examples of highly active-type promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The promoter may be a promoter having any of the nucleotide sequences of the promoters exemplified above, such as the nucleotide sequences shown as SEQ ID NO: 13 and 78. The promoter may also be a conservative variant of any of the nucleotide sequences of the promoters exemplified above, such as the nucleotide sequences shown as SEQ ID NO: 13 and 78). That is, the promoters exemplified above each can be used as they are, or after being modified as required. Promoters defined with the above-mentioned promoter names include not only the promoters exemplified above, respectively, but also include conservative variants thereof. Namely, for example, the term "F1 promoter" includes not only a promoter having the nucleotide sequence shown as SEQ ID NO: 13, but also includes conservative variants thereof. Also, for example, the term "T7 promoter" includes not only a promoter having the nucleotide sequence shown as SEQ ID NO: 78, but also includes conservative variants thereof. The descriptions concerning conservative variants of the ribonuclease III gene mentioned later can be similarly applied to conservative variants of promoters. For example, the promoter may be a promoter having a nucleotide sequence showing a homology of, for example, 80% or more, 90% or more, 95% or more, 97% or more, or 99% or more, to the nucleotide sequence shown as SEQ ID NO: 13 or 78, so long as the original function is maintained. Incidentally, the term "original function" used for promoters refers to a function of providing the expression of a gene ligated immediately downstream thereof under certain conditions. The term "certain conditions" refers to conditions under which the original promoter provides the expression of a gene ligated immediately downstream thereof. For example, a gene can be constitutively expressed from the F1 promoter. Also, for example, a gene can be inducibly expressed from the T7 promoter, T5 promoter, T3 promoter, or SP6 promoter in the presence of T7 RNA polymerase, T5 RNA polymerase, T3 RNA polymerase, or SP6 RNA polymerase. A conservative variant of a promoter may have a transcription activity of, for example, 80% or more, 90% or more, or 100% or more, of that of the original promoter. The presence or absence of gene expression and intensity of gene expression (transcription activity) can be confirmed by, for example, using a reporter gene.

A terminator for termination of gene transcription may be located downstream of the objective RNA gene. The terminator is not particularly limited so long as it functions in the host. The terminator may be a terminator derived from the host, or a heterogenous terminator. The terminator may be the native terminator of the objective RNA gene, or a terminator of another gene. Specific examples of the terminator include, for example, the terminator of bacteriophage BFK20.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Methods for introducing the expression unit for the objective RNA into a coryneform bacterium are not particularly limited. The phrase "introduction of an expression unit for objective RNA" refers to making a host to harbor the expression unit for the objective RNA, and may specifically refer to expressively introducing the objective RNA gene into a host. The phrase "introduction of an expression unit for objective RNA" includes not only cases of collectively introducing the expression unit for the objective RNA that has been preliminarily constructed into a host, but also includes cases of introducing at least the objective RNA gene into a host so as to construct the expression unit for the objective RNA in the host, unless otherwise stated. In the bacterium, the expression unit for the objective RNA may be present in a vector autonomously replicable separately from the chromosome, such as plasmid, or may be integrated into the chromosome. That is, the bacterium, for example, may have the expression unit for the objective RNA on a vector, and in other words, may have a vector containing the expression unit for the objective RNA. The bacterium, for example, may also have the expression unit for the objective RNA on the chromosome. The bacterium may have only one copy of the expression unit for the objective RNA, or two or more copies of the expression unit for the objective RNA. The copy number of the expression unit for the objective RNA present in the bacterium, for example, may be 5 copies/cell or more, 10 copies/cell or more, 20 copies/cell or more, 30 copies/cell or more, 50 copies/cell or more, 70 copies/cell or more, 100 copies/cell or more, 150 copies/cell or more, 200 copies/cell or more, 300 copies/cell or more, 500 copies/cell or more, 1000 copies/cell or more, or may be 2000 copies/cell or less, 1500 copies/cell or less, 1000 copies/cell or less, 500 copies/cell or less, or 300 copies/cell or less, or may be a range defined as a non-contradictory combination thereof. The bacterium may have only one kind of expression unit for the objective RNA, or two or more kinds of expression units for the objective RNA. The copy number and kind of the expression unit for the objective RNA may also be read as the copy number and kind of the objective RNA gene, respectively. When the bacterium has two or more expression units for the objective RNA, it is sufficient that those expression units are harbored by the bacterium so that the objective RNA is produced. For example, all of those expression units may be harbored on a single expression vector or on the chromosome. Alternatively, those expression units may be harbored separately on a plurality of expression vectors, or separately on a single or plurality of expression vectors and the chromosome.

The expression unit for the objective RNA can be introduced into a host by, for example, using a vector containing the expression unit for the objective RNA. The vector containing the expression unit for the objective RNA is also referred to as "expression vector for objective RNA". The expression vector for the objective RNA can be constructed by, for example, ligating the expression unit for the objective RNA with a vector. Alternatively, for example, when a vector contains a promoter that functions in a coryneform bacterium, the expression vector for the objective RNA can also be constructed by ligating the objective RNA gene downstream of the promoter. By transforming a host with the expression vector for the objective RNA, a transformant into which the vector has been introduced can be obtained, namely, the expression unit for the objective RNA can be introduced into the host. As the vector, a vector autonomously replicable in cells of the host can be used. The vector can be a multi-copy vector. The copy number of the vector, for example, may be 5 copies/cell or more, 10 copies/cell or more, 20 copies/cell or more, 30 copies/cell or more, 50 copies/cell or more, 70 copies/cell or more, 100 copies/cell or more, 150 copies/cell or more, 200 copies/cell or more, 300 copies/cell or more, 500 copies/cell or more, 1000 copies/cell or more, or may be 2000 copies/cell or less, 1500 copies/cell or less, 1000 copies/cell or less, 500 copies/cell or less, or 300 copies/cell or less, or may be a range defined as a non-contradictory combination thereof. Furthermore, the vector can contain a marker such as an antibiotic resistance gene or auxotrophy-complementing gene for selection of transformants. Furthermore, the vector may contain a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vectors autonomously replicable in coryneform bacteria include, for example, pHl519 (Agric. Biol. Chem., 48, 2901-2903 (1984)); pAM330 (Agric. Biol. Chem., 48, 2901-2903 (1984)); plasmids obtained by improving these and having a drug resistance gene; pCRY30 (Japanese Patent Laid-open (Kokai) No. 3-210184); pCRY21, pCRY2KE, pCRY2KX, pCRY31, pCRY3KE, and pCRY3KX (Japanese Patent Laid-open (Kokai) No. 2-72876 and U.S. Pat. No. 5,185,262); pCRY2 and pCRY3 (Japanese Patent Laid-open (Kokai) No. 1-191686); pAJ655, pAJ611, and pAJ1844 (Japanese Patent Laid-open (Kokai) No. 58-192900); pCG1 (Japanese Patent Laid-open (Kokai) No. 57-134500); pCG2 (Japanese Patent Laid-open (Kokai) No. 58-35197); pCG4 and pCG11 (Japanese Patent Laid-open (Kokai) No. 57-183799); pPK4 (U.S. Pat. No. 6,090,597); pVK4 (Japanese Patent Laid-open (Kokai) No. 9-322774); pVK7 (Japanese Patent Laid-open (Kokai) No. 10-215883); pVK9 (US2006-0141588); pVC7 (Japanese Patent Laid-open (Kokai) No. 9-070291); and pVS7 (WO2013/069634). Specific examples of vectors autonomously replicable in coryneform bacteria also include, for example, pVC7H1, pVC7H2, pVC7H3, pVC7H4, pVC7H5, pVC7H6, and pVC7H7 (present Examples), which are variants of pVC7. Specific examples of vectors autonomously replicable in coryneform bacteria also include, for example, pPK4H1, pPK4H2, pPK4H3, pPK4H4, pPK4H5, and pPK4H6 (present Examples), which are variants of pPK4.

Furthermore, the expression unit for the objective RNA can be introduced into the chromosome of a host by, for example, using a transposon such as artificial transposon. When a transposon is used, the expression unit for the objective RNA can be introduced into the chromosome via homologous recombination or due to the transposition activity thereof. The expression unit for the objective RNA can also be introduced into the chromosome of a host by introduction methods utilizing homologous recombination. Examples of the introduction methods utilizing homologous recombination include, for example, methods of using a linear DNA, a plasmid containing a temperature sensitive replication origin, a plasmid capable of conjugative transfer, a suicide vector not having a replication origin that functions in a host, or the like. Only one copy or two or more copies of the expression unit for the objective RNA may be introduced. For example, by performing homologous recombination using a sequence present in multiple copies on a chromosome as a target, multiple copies of the expression unit for the objective RNA can be introduced into the chromosome. Examples of the sequence present in multiple copies on a chromosome include repetitive DNAs, and inverted repeats located at the both ends of a transposon. In addition, at least the objective RNA gene may be introduced into the chromosome so as to construct the expression unit for the objective RNA on the chromosome. For example, by introducing the objective RNA gene downstream of a promoter sequence on the chromosome of a host, the expression unit for the objective RNA can be constructed on the chromosome. Incidentally, introduction of a part of the expression unit for the objective RNA, such as the objective RNA gene, into the chromosome can be performed in the same manner as introduction of the whole of the expression unit for the objective RNA into the chromosome.

Methods for transformation are not particularly limited, and generally used methods, such as the protoplast method (Gene, 39, 281-286 (1985)), the electroporation method (Bio/Technology, 7, 1067-1070 (1989)), and the electric pulse method (JP H2-207791 A), can be used.

<1-2> Reduction in Ribonuclease III Activity

The bacterium has been modified so that the activity of ribonuclease III (RNaseIII) is reduced. Specifically, the bacterium has been modified so that the activity of ribonuclease III is reduced as compared with a non-modified strain. The activity of ribonuclease III may be reduced to, for example, 50% or less, 20% or less, 10% or less, 5% or less, or 0% of that of a non-modified strain. That is, the bacterium may have been modified so that, for example, the activity of ribonuclease III is deleted (eliminated). By modifying a coryneform bacterium so that the activity of ribonuclease III is reduced, the objective RNA-producing ability of the bacterium can be improved, and that is, production of the objective RNA by using the bacterium can be increased.

Hereinafter, ribonuclease III and a gene encoding it will be explained.

The term "ribonuclease III" refers to a protein that has an activity of catalyzing the reaction of cleaving specific RNA such as double-stranded RNA. A gene encoding ribonuclease III is also referred to as "ribonuclease III gene".

Examples of the ribonuclease III gene include rnc gene. A protein (ribonuclease III) encoded by rnc gene is also referred to as "Rnc protein".

The nucleotide sequences of ribonuclease III genes, such as rnc genes, possessed by coryneform bacteria and the amino acid sequences of ribonucleases III encoded by these genes, such as Rnc proteins, can be obtained from, for example, public databases such as NCBI (National Center for Biotechnology Information). The nucleotide sequence of the rnc gene of the *C. glutamicum* ATCC 13869 strain and the amino acid sequence of the Rnc protein encoded by the gene are shown in SEQ ID NOS: 51 and 52, respectively. That is, the ribonuclease III gene may be, for example, a gene having the nucleotide sequence of any of the ribonuclease III genes exemplified above, such as the nucleotide sequence shown as SEQ ID NO: 51. Also, ribonuclease III may be, for example, a protein having the amino acid sequence of any of the ribonucleases III exemplified above, such as the amino acid sequence shown as SEQ ID NO: 52). The expression "a gene or protein has a nucleotide or amino acid sequence" means that a gene or protein includes the nucleotide or amino acid sequence unless otherwise stated, and also includes cases where a gene or protein has only the nucleotide or amino acid sequence.

The ribonuclease III gene may be a variant of any of the ribonuclease III genes exemplified above, such as a gene having the nucleotide sequence shown as SEQ ID NO: 51, so long as the original function is maintained. Similarly, ribonuclease III may be a variant of any of the ribonucleases III exemplified above, such as a protein having the amino acid sequence shown as SEQ ID NO: 52, so long as the original function is maintained. Such a variant that maintains the original function is also referred to as "conservative variant". The term "rnc gene" includes not only the rnc genes exemplified above, but also includes conservative variants thereof. Similarly, the term "Rnc protein" includes not only the Rnc proteins exemplified above, but also includes conservative variants thereof. Examples of the conservative variants include, for example, homologues and artificially modified versions of the ribonuclease III genes and ribonucleases III exemplified above.

The expression "the original function is maintained" means that a variant of gene or protein has a function (such as activity or property) corresponding to the function (such as activity or property) of the original gene or protein. That is, the expression "the original function is maintained" used for the ribonuclease III gene means that a variant of the gene encodes a protein that maintains the original function, that is, a protein having ribonuclease III activity. Furthermore, the expression "the original function is maintained" used for ribonuclease III means that a variant of the protein has ribonuclease III activity.

Ribonuclease III activity can be measured by, for example, incubating the enzyme with RNA that serves as a substrate thereof (e.g. double-stranded RNA), and measuring the enzyme-dependent cleavage of the RNA. Specifically, ribonuclease III activity is generally measured in the manner described in Methods Enzymol. 2001; 342:143-58. One example is a method of adding an enzyme, such as a crude extract from cells or a partially purified enzyme thereof to a synthetic substrate of $^3$H-labeled poly (A-U) in a double-stranded form to react them at 35° C., treating the reaction mixture with trichloroacetic acid, and measuring the degree of the reaction-time-dependent decrease in radioactivity in the precipitate fraction, which contains high-molecular-weight nucleotides. That is, ribonuclease III activity can be calculated on the basis of the degree of the decrease in radioactivity as an indicator of cleavage of the substrate. In addition, another example is a method of adding $^{32}$P-radiolabeled double-stranded RNA as a substrate to a reaction mixture containing an enzyme (30 mM Tris-HCl (pH8.0), 250 mM potassium glutamate or 160 mM NaCl, 5 mM spermidine, 0.1 mM EDTA, and 0.1 mM DTT), incubating at 37° C. for 5 min, adding thereto MgCl$_2$ at a final concentration of 10 mM to initiate the RNA cleavage reaction, and adding thereto, after appropriate proceeding of the reaction, an equal volume of a mixture of EDTA and electrophoresis marker dye, of which the EDTA concentration is one providing a final concentration of 20 mM or more, to stop the reaction. Then, ribonuclease III activity can be detected by applying samples after the reaction to electrophoresis using a denaturing 15% (w/v) polyacrylamide gel with TBE buffer (89 mM Tris/Tris-borate, and 2 mM EDTA) containing 7 M urea, and applying the gel to a radiation imaging analyzer to analyze cleaved RNA fragments.

Hereinafter, examples of the conservative variants will be explained.

Homologues of the ribonuclease III gene or homologues of ribonuclease III can be easily obtained from public databases by, for example, BLAST search or FASTA search using the nucleotide sequence of any of the ribonuclease III genes exemplified above or the amino acid sequence of any of the ribonucleases III exemplified above as a query sequence. Furthermore, homologues of the ribonuclease III gene can be obtained by, for example, PCR using the chromosome of a coryneform bacterium as the template, and oligonucleotides prepared on the basis of the nucleotide sequence of any of these known ribonuclease III genes and adjacent regions thereof as primers.

The ribonuclease III gene may be a gene encoding a protein having the amino acid sequence of any of the ribonucleases III exemplified above (e.g. the amino acid sequence shown as SEQ ID NO: 52), but which includes substitution, deletion, insertion, and/or addition of one or several amino acid residues at one or several positions, so long as the original function is maintained. Although the number meant by the term "one or several" mentioned above may differ depending on the positions of amino acid residues in the three-dimensional structure of the protein or the types of amino acid residues, specifically, it is, for example, 1 to 50, 1 to 40, or 1 to 30, 1 to 20, 1 to 10, 1 to 5, or 1 to 3.

The aforementioned substitution, deletion, insertion, and/or addition of one or several amino acid residues are/is a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues as described above includes a naturally occurring mutation due to an individual difference, or a difference of species of the bacterium from which the gene is derived (mutant or variant).

The ribonuclease III gene may be a gene encoding a protein having an amino acid sequence showing a homology of, for example, 80% or more, 90% or more, 95% or more, 97% or more, or 99% or more, to the total amino acid sequence of any of the ribonucleases III exemplified above, so long as the original function is maintained. In this description, "homology" means "identity".

The ribonucleases III gene may also be a DNA that is able to hybridize under stringent conditions with a complementary sequence of the nucleotide sequence of any of the ribonucleases III genes exemplified above, such as the nucleotide sequence shown as SEQ ID NO: 51, or a probe that can be prepared from the complementary sequence, so long as the original function is maintained. The term "stringent conditions" refers to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, or not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe may be, for example, a part of a complementary sequence of the gene. Such a probe can be prepared by PCR using oligonucleotides prepared on the basis of a known gene sequence as primers and a DNA fragment containing any of these nucleotide sequences as a template. As the probe, for example, a DNA fragment having a length of about 300 bp can be used. In such a case, the washing conditions of the hybridization may be, for example, 50° C., 2×SSC and 0.1% SDS.

Furthermore, since the degeneracy of codons differs depending on the host, arbitrary codons in the ribonucleases III gene may be replaced with respective equivalent codons. That is, the ribonucleases III gene may be a variant of any of the ribonucleases III genes exemplified above due to the degeneracy of the genetic code.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as one described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

The aforementioned descriptions concerning variants of the genes and proteins can be similarly applied to variants of other arbitrary proteins and the objective RNA, and genes encoding them.

Hereinafter, methods for reducing the activity of a protein (enzyme) such as ribonucleases III will be explained.

The expression "the activity of a protein is reduced" means that the activity of the protein is reduced as compared with a non-modified strain. Specifically, the expression "the activity of a protein is reduced" means that the activity of the protein per cell is reduced as compared with that of a non-modified strain. The term "non-modified strain" refers to a control strain that has not been modified so that the activity of an objective protein is reduced. Examples of the non-modified strain include a wild-type strain and parent strain. Specific examples of the non-modified strain include the respective type strains of the species of bacteria. Specific examples of the non-modified strain also include strains exemplified above in relation to the description of coryneform bacteria. That is, in an embodiment, the activity of a protein may be reduced as compared with a type strain, i.e. the type strain of the species to which the bacterium as described herein belongs. In another embodiment, the activity of a protein may also be reduced as compared with the *C. glutamicum* ATCC 13032 strain. In another embodiment, the activity of a protein may also be reduced as compared with the *C. glutamicum* 2256 strain (ATCC 13869). The state that "the activity of a protein is reduced" also includes a state that the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein). The state that "the number of molecules of the protein per cell is reduced" also includes a state that the protein does not exist at all. The state that "the function of each molecule of the protein is reduced" also includes a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" means that the expression of the gene is reduced as compared with a non-modified strain such as a wild-type strain and parent strain. Specifically, the expression "the expression of a gene is reduced" means that the expression of the gene per cell is reduced as compared with that of a non-modified strain. More specifically, the expression "the expression of a gene is reduced" may mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter, a Shine-Dalgarno (SD) sequence (also referred to as ribosome-binding site (RBS)), and a spacer region between RBS and the start codon of the gene. When an expression control sequence is modified, one or more nucleotides, two or more nucleotides, or three or more nucleotides, of the expression control sequence are modified. For example, the transcription efficiency of a gene can be reduced by, for example, replacing the promoter of the gene on a chromosome with a weaker promoter. The term "weaker promoter" means a promoter providing an attenuated transcription of a gene compared with an inherently existing wild-type promoter of the gene. Examples of weaker promoters include, for example, inducible promoters. That is, an inducible promoter may function as a weaker promoter under a non-induced condition, such as in the absence of the corresponding inducer. Furthermore, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described herein.

The modification for reducing the activity of a protein can also be attained by, for example, disrupting a gene encoding the protein. The expression "a gene is disrupted" means that a gene is modified so that a protein that can normally function is not produced. The state that "a protein that normally functions is not produced" includes a state that the protein is not produced at all from the gene, and a state that the protein of which the function (such as activity or property) per molecule is reduced or eliminated is produced from the gene.

Disruption of a gene can be attained by, for example, deleting the gene on a chromosome. The term "deletion of a gene" refers to deletion of a partial or entire region of the coding region of the gene. Furthermore, the whole of a gene including sequences upstream and downstream from the coding region of the gene on a chromosome may be deleted. The region to be deleted may be any region such as an N-terminal region (region encoding an N-terminal region of a protein), an internal region, or a C-terminal region (region encoding a C-terminal region of a protein), so long as the activity of the protein can be reduced. Deletion of a longer region can usually more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, the reading frames of the sequences upstream and downstream from the region to be deleted do not have to be the same. Inconsistency of reading frames may cause a frameshift downstream of the region to be deleted.

Disruption of a gene can also be attained by, for example, introducing a mutation for an amino acid substitution (missense mutation), a stop codon (nonsense mutation), addition or deletion of one or two nucleotide residues (frame shift mutation), or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another nucleotide sequence into a coding region of the gene on a chromosome. Site of the insertion may be in any region of the gene, and insertion of a longer nucleotide sequence can usually more surely inactivate the gene. It is a particular example that reading frames of the sequences upstream and downstream from the insertion site are not the same. Inconsistency of reading frames may cause a frameshift downstream of the region to be deleted. The other nucleotide sequence is not particularly limited so long as a sequence that reduces or eliminates the activity of the encoded protein is chosen, and examples thereof include, for example, a marker gene such as antibiotic resistance genes, and a gene useful for production of an objective substance.

Particularly, disruption of a gene may be carried out so that the amino acid sequence of the encoded protein is deleted. In other words, the modification for reducing the activity of a protein can be attained by, for example, deleting the amino acid sequence of the protein, specifically, modifying a gene so as to encode a protein of which the amino acid sequence is deleted. The term "deletion of the amino acid sequence of a protein" refers to deletion of a partial or entire region of the amino acid sequence of the protein. In addition, the term "deletion of the amino acid sequence of a protein" means that the original amino acid sequence disappears in the protein, and also includes cases where the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or entire region of the coding region of a gene, a region encoded by the deleted region can be deleted in the encoded protein. In addition, for example, by introduction of a stop codon into the coding region of a gene, a region encoded by the downstream region of the introduction site can be deleted in the encoded protein. In addition, for example, by frameshift in the coding region of a gene, a region encoded by the frameshift region can be deleted in the encoded protein. The aforementioned descriptions concerning the position and length of the region to be deleted in deletion of a gene can be similarly applied to the position and length of the region to be deleted in deletion of the amino acid sequence of a protein.

Such modification of a gene on a chromosome as described above can be attained by, for example, preparing a disruption-type gene modified so that it is unable to produce a protein that normally functions, and transforming a host with a recombinant DNA containing the disruption-type gene to cause homologous recombination between the disruption-type gene and the wild-type gene on a chromosome and thereby substitute the disruption-type gene for the wild-type gene on the chromosome. In this procedure, if a marker gene selected according to the characteristics of the host such as auxotrophy is included in the recombinant DNA, the experimental operation becomes easier. Examples of the disruption-type gene include a gene of which a partial or entire region of the coding region is deleted, gene including a missense mutation, gene including a nonsense mutation, gene including a frame shift mutation, and gene including insertion of a transposon or marker gene. The protein encoded by the disruption-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

Such methods for reducing the activity of a protein as mentioned above may be used independently or in an arbitrary combination.

When a protein functions as a complex having a plurality of subunits, a part or all of the plurality of subunits may be modified, so long as the activity of the protein is eventually reduced. That is, for example, a part or all of a plurality of genes that encode the respective subunits may be disrupted or the like. Furthermore, when there is a plurality of isozymes of a protein, some or all of the activities of the plurality of isozymes may be reduced, so long as the activity of the protein is eventually reduced. That is, for example, some or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, microarray, RNA-seq, and so forth (Molecular Cloning, Cold Spring Harbor Laboratory Press, Cold Spring Harbor (USA), 2001). The amount of mRNA (such as the number of molecules of the mRNA per cell) can be reduced to, for example, 50% or less, 20% or less, 10% or less, 5% or less, or 0% of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein (such as the number of molecules of the protein per cell) can be reduced to, for example, 50% or less, 20% or less, 10% or less, 5% or less, or 0% of that of a non-modified strain.

Disruption of a gene can be confirmed by determining nucleotide sequence of a part or the whole of the gene, restriction enzyme map, full length, or the like of the gene depending on the means used for the disruption.

The aforementioned methods for reducing the activity of a protein can be applied to reduction in the activities of arbitrary proteins and reduction in the expression of arbitrary genes, as well as reduction in ribonucleases III activity.

<2> Method

The objective RNA can be produced by using the thus-obtained bacterium. The method is a method for producing the objective RNA, the method including the steps of culturing the bacterium, and collecting the transcribed objective RNA. By culturing the bacterium in a medium, the objective RNA can be transcribed and accumulated in cells of the bacterium. That is, specifically, the method is a method for producing the objective RNA, the method including the steps of culturing the bacterium in a medium, to transcribe the objective RNA and accumulate the objective RNA in cells of the bacterium, and collecting the objective RNA from the cells.

The bacterium can be cultured according to, for example, culture conditions usually used for culturing bacteria such as coryneform bacteria. The bacterium can be cultured in, for example, a usual medium containing a carbon source, a nitrogen source, and inorganic ions. In addition, for example, organic micronutrients such as vitamins and amino acids can also be added as required.

As the carbon source, for example, carbohydrates such as glucose and sucrose, organic acids such as acetic acid, alcohols, and others can be used. As the nitrogen source, for example, ammonia gas, aqueous ammonia, ammonium salts, and others can be used. As the inorganic ions, for example, calcium ions, magnesium ions, phosphate ions, potassium ions, iron ions, and so forth can be appropriately used as required. The culture can be performed within appropriate ranges of pH 5.0 to 8.5 and 15 to 37° C. under aerobic conditions for 10 to 120 hours. Furthermore, culture conditions for L-amino acid production using bacteria such as coryneform bacteria and culture conditions for methods of secretory production of a protein using bacteria such as coryneform bacteria can be referred to (WO01/23591, WO2005/103278, WO2013/065869, WO2013/065772, WO2013/118544, WO2013/062029, etc.). Furthermore, when an inducible promoter is used for expression of the objective RNA, the expression of the objective RNA can be appropriately induced.

By culturing the bacterium under such conditions, the objective RNA is transcribed and accumulated in cells of the bacterium.

The expression and accumulation of the objective RNA can be confirmed by, for example, applying a fraction containing a cell extract as a sample to electrophoresis, and detecting a band corresponding to the molecular weight of the objective RNA.

The objective RNA can be collected from the cells by appropriate methods used for separation and purification of compounds. Examples of such methods include, for example, centrifugation, salting out, ethanol precipitation, ultrafiltration, gel filtration chromatography, ion exchange chromatography, affinity chromatography, and electrophoresis. These methods can be independently used, or can be used in an appropriate combination. Specifically, for example, the cells can be disrupted with ultrasonic waves or the like, a supernatant can be obtained by removing the cells from the cell-disrupted suspension by centrifugation or the like, and the objective RNA can be collected from the supernatant by the ion exchange resin method or the like. The collected objective RNA may be a free compound, a salt thereof, or a mixture thereof. In addition, the collected objective RNA may also be a complex with a high-molecular-weight compound such as a protein. That is, the term "objective RNA" may refer to the objective RNA in a free form, a salt thereof, a complex thereof with a high-molecular-weight compound such as a protein, or a mixture thereof, unless otherwise stated. Examples of the salt include, for example, ammonium salt and sodium salt.

The collected objective RNA may contain, for example, such components as bacterial cells, medium components, moisture, and by-product metabolites of the bacterium, in addition to the objective RNA. The objective RNA may also be purified at a desired extent. Purity of the collected objective RNA may be, for example, 30% (w/w) or higher, 50% (w/w) or higher, 70% (w/w) or higher, 80% (w/w) or higher, 90% (w/w) or higher, or 95% (w/w) or higher.

EXAMPLES

Hereinafter, the present invention will be more specifically explained with reference to examples. However, the present invention is not limited by these examples.

<1> Acquisition of Ribonuclease III Gene-Deficient Strain of *Corynebacterium glutamicum*

A disruption strain of a ribonuclease III (RNaseIII) homologue gene (hereinafter also referred to as "rnc gene") of the *C. glutamicum* 2256 strain (ATCC 13869 strain, hereinafter also referred to simply as "2256 strain") was constructed in the following manner.

First, a region located at REGION: 2115207 . . . 2115950 of the genomic sequence information of the *C. glutamicum* 2256 strain (Accession No. AP017557) in a gene database (GenBank) was deduced to be an rnc gene on the basis of amino acid sequence homology with respect to known RNaseIII. Then, as necessary information for deleting this gene, DNA nucleotide sequence information of the ORF (open reading frame) region thereof and of about 1000 nucleotides (1 kb) each of upstream and downstream regions thereof was obtained from the gene database (GenBank).

Next, genome DNA was obtained from cells of the 2256 strain with DNeasy Blood & Tissue Kit (QIAGEN). PCR amplification was performed by using this genome DNA as the template and PrimeSTAR GXL DNA Polymerase (TAKARA BIO), as well as primers of SEQ ID NOS: 1 and 2 to obtain a DNA fragment of about 1 kb containing an upstream region of the rnc gene, and primers of SEQ ID NOS: 3 and 4 to obtain a DNA fragment of about 1 kb containing a downstream region of the rnc gene. The PCR conditions were set according to a protocol recommended by the manufacturer. Then, these DNA fragments were ligated with a plasmid pBS4S (WO2005/113745 and WO2005/113744; not having replication ability in *C. glutamicum*), which harbors a sacB gene, in the following manner. Specifically, PCR amplification was performed by using pBS4S as the template, primers of SEQ ID NOS: 5 and 6, and PrimeSTAR GXL DNA Polymerase to obtain an amplified fragment of pBS4S. Then, both the DNA fragments of the upstream and downstream regions of the rnc gene obtained above and the amplified fragment of pBS4S were mixed, and these three fragments were mutually ligated by using In-Fusion HD Cloning Kit (Clontech) (FIG. 1). Competent cells of the *Escherichia coli* JM109 strain (TAKARA BIO) were transformed with the reaction mixture, applied to LB agar medium containing 25 μg/mL of kanamycin, and cultured at 37° C. overnight. Then, single colonies were isolated from colonies that appeared on the agar medium, to obtain transformants resistant to kanamycin. Plasmids were extracted from the obtained transformants in the usual manner. A plasmid containing the DNA fragments of the upstream and downstream regions of the rnc gene was identified by a structural analysis, and designated as pBS4SΔrnc (FIG. 1).

This plasmid is not able to autonomously replicate in coryneform bacteria. Therefore, if coryneform bacteria are transformed with this plasmid, transformants in which this plasmid is incorporated into the chromosome by homologous recombination and which thereby have kanamycin resistance appear, although it occurs at an extremely low frequency. Thus, the 2256 strain was transformed with a high concentration of the plasmid pBS4SΔrnc by the electric pulse method, applied to CM-Dex agar medium (5 g/L of glucose, 10 g/L of polypeptone, 10 g/L of yeast extract, 1 g/L of $KH_2PO_4$, 0.4 g/L of $MgSO_4$-$7H_2O$, 0.01 g/L of $FeSO_4$-$7H_2O$, 0.01 g/L of $MnSO_4$-$7H_2O$, 3 g/L of urea, 1.2 g/L of soybean hydrolysate, adjusted to pH 7.5 with KOH, 20 g/L of agar) containing 25 μg/mL of kanamycin, and cultured at 30° C. overnight. As a result, a few colonies appeared. These strains grown on the medium each were a so-called once-recombinant strain, in which the kanamycin resistance gene and the sacB gene derived from the plasmid were incorporated into the genome as a result of homologous recombination between a DNA sequence fragment adjacent to (upstream or downstream of) the rnc gene on the plasmid and a region adjacent to the rnc gene on the genome of the 2256 strain.

Figure 2:
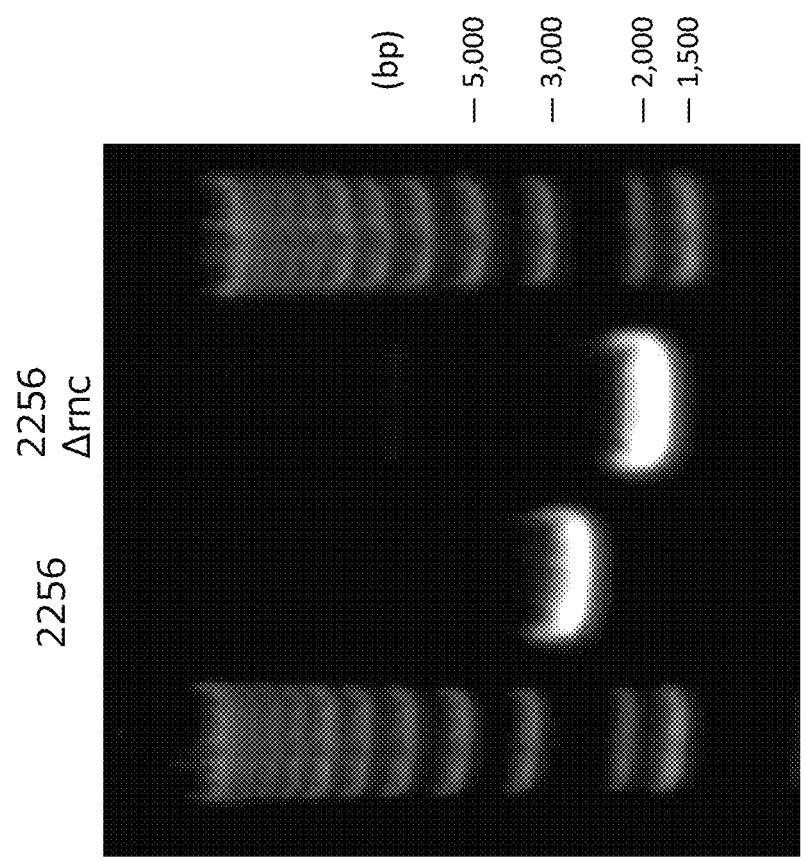
FIG. 2 shows an agarose gel electrophoretogram (photograph) that confirms deletion of the rnc gene.

Then, these once-recombinant strains were each cultured in CM-Dex medium (having the same composition as that of CM-Dex agar medium except that it does not contain agar) not containing kanamycin at 30° C. overnight. The culture broth was appropriately diluted, applied to 10% (w/v)-sucrose-containing Dex-S10 agar medium (100 g/L of sucrose, 10 g/L of polypeptone, 10 g/L of yeast extract, 1 g/L of $KH_2PO_4$, 0.4 g/L of $MgSO_4$-$7H_2O$, 0.01 g/L of $FeSO_4$-$7H_2O$, 0.01 g/L of $MnSO_4$-$4$-$5H_2O$, 3 g/L of urea, 1.2 g/L of soybean protein hydrolysate solution, 10 μg/L of biotin, adjusted to pH 7.5 with KOH, 20 g/L of agar) not containing kanamycin, and cultured at 30° C. overnight. As a result, a few colonies appeared. These strains were each considered to be a strain in which the sacB gene was removed as a result of the $2^{nd}$ homologous recombination and which thereby became insensitive to sucrose. The thus-obtained strains would include strain(s) of which the rnc gene was replaced with the deficient-type, and strain(s) of which the rnc gene reverted to the wild-type. Thus, the colonies that appeared were applied to colony PCR using KOD FX NEO (TOYOBO), to select rnc gene-deficient strains. As a result of an analysis of the length of the rnc gene region of those strains through PCR amplification with primers of SEQ ID NOS: 7 and 8, some strains provided a DNA fragment having a shorter length in PCR amplification than that observed for the case of using the genome DNA of the 2256 strain (wild-type) as the template. Thus, one strain thereof was selected as an rnc gene-deficient strain, and designated as 2256Δrnc. Incidentally, the length of the PCR-amplified DNA fragment observed for the case of the wild-type rnc gene is about 3 kbp, while the length of the PCR-amplified DNA fragment observed for the case of deficient-type rnc gene is about 2 kbp (FIG. 2).

<2> Curing of Endogenous Plasmid

The 2256 strain has an endogenous plasmid pAM330 (Yamaguchi, Ryuji, et al. "Determination of the complete nucleotide sequence of *Brevibacterium lactofermentum* plasmid pAM330 and analysis of its genetic information." Agricultural and biological chemistry 50.11 (1986): 2771-

Figure 3:
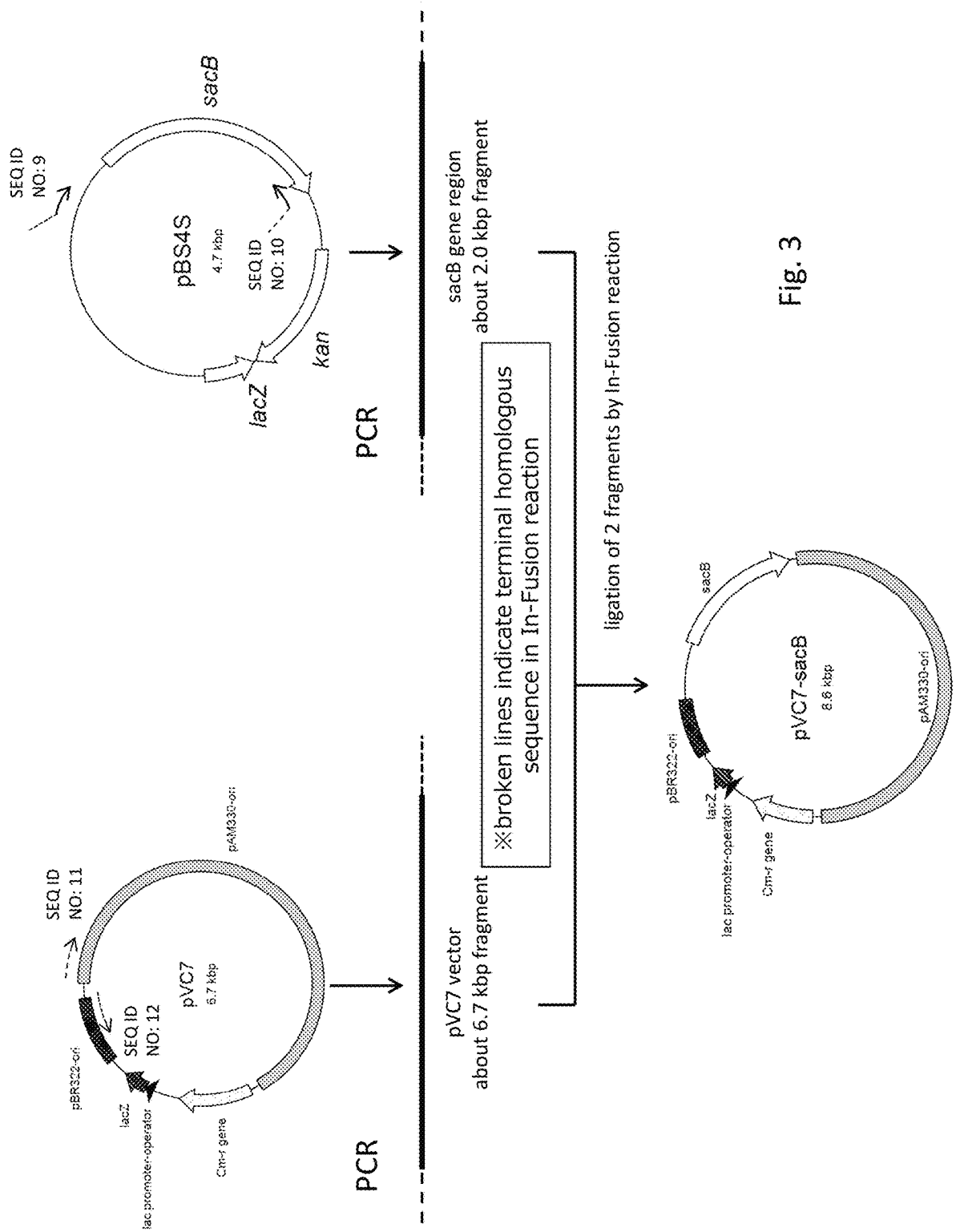
FIG. 3 shows a diagram of the construction scheme of plasmid pVC7-sacB.

2778). There was constructed a plasmid pVC7-sacB, which corresponds to a plasmid pVC7 (JP1997-070291A) incorporated with a sacB gene. pVC7 is a composite plasmid of pAM330 and an *Escherichia coli*-universal vector pHSG399 (TAKARA BIO). Specifically, PCR amplification was performed by using pBS4S as the template, primers of SEQ ID NOS: 9 and 10, and PrimeSTAR GXL DNA Polymerase to obtain an amplified fragment of the sacB gene. Separately, PCR amplification was performed by using pVC7 as the template, primers of SEQ ID NOS: 11 and 12, and KOD FX NEO (TOYOBO) to obtain an amplified fragment of pVC7. Both the amplified fragments were mixed, and mutually ligated by using In-Fusion HD Cloning Kit (Clontech). Then, competent cells of the *Escherichia coli* JM109 strain (TAKARA BIO) were transformed with the reaction mixture, applied to LB agar medium containing 25 µg/mL of chloramphenicol, and cultured at 37° C. overnight. Then, single colonies were isolated from colonies that appeared. Plasmids were extracted from the obtained transformants in the usual manner. An objective plasmid was identified by DNA sequencing analysis, and designated as pVC7-sacB (FIG. 3). The strains 2256 and 2256Δrnc were each introduced with pVC7-sacB by the electric pulse method, applied to CM-Dex agar medium containing 5 µg/mL of chloramphenicol, and cultured at 30° C. overnight, to obtain a plurality of transformants for each of strains 2256/pVC7-sacB and 2256Δrnc/pVC7-sacB. Then, from them, there were obtained strains 2256ΔpAM330/pVC7-sacB and 2256ΔrncΔpAM330/pVC7-sacB, of which the endogenous plasmid pAM330 was removed. Then, these strains were each applied to Dex-S10 agar medium, and cultured at 30° C. overnight, to obtain strains 2256ΔpAM330 and 2256ΔrncΔpAM330, which were cured of pVC7-sacB to thereby become insensitive to sucrose.

<3> Construction of Single-Direction Transcription Plasmid pVC7-Pf1-U1Ainsert

A plasmid, pVC7-Pf1-U1Ainsert, for transcription of a U1A-binding sequence as objective RNA under control of F1 promoter in a single direction was constructed in the following manner.

Figure 4:
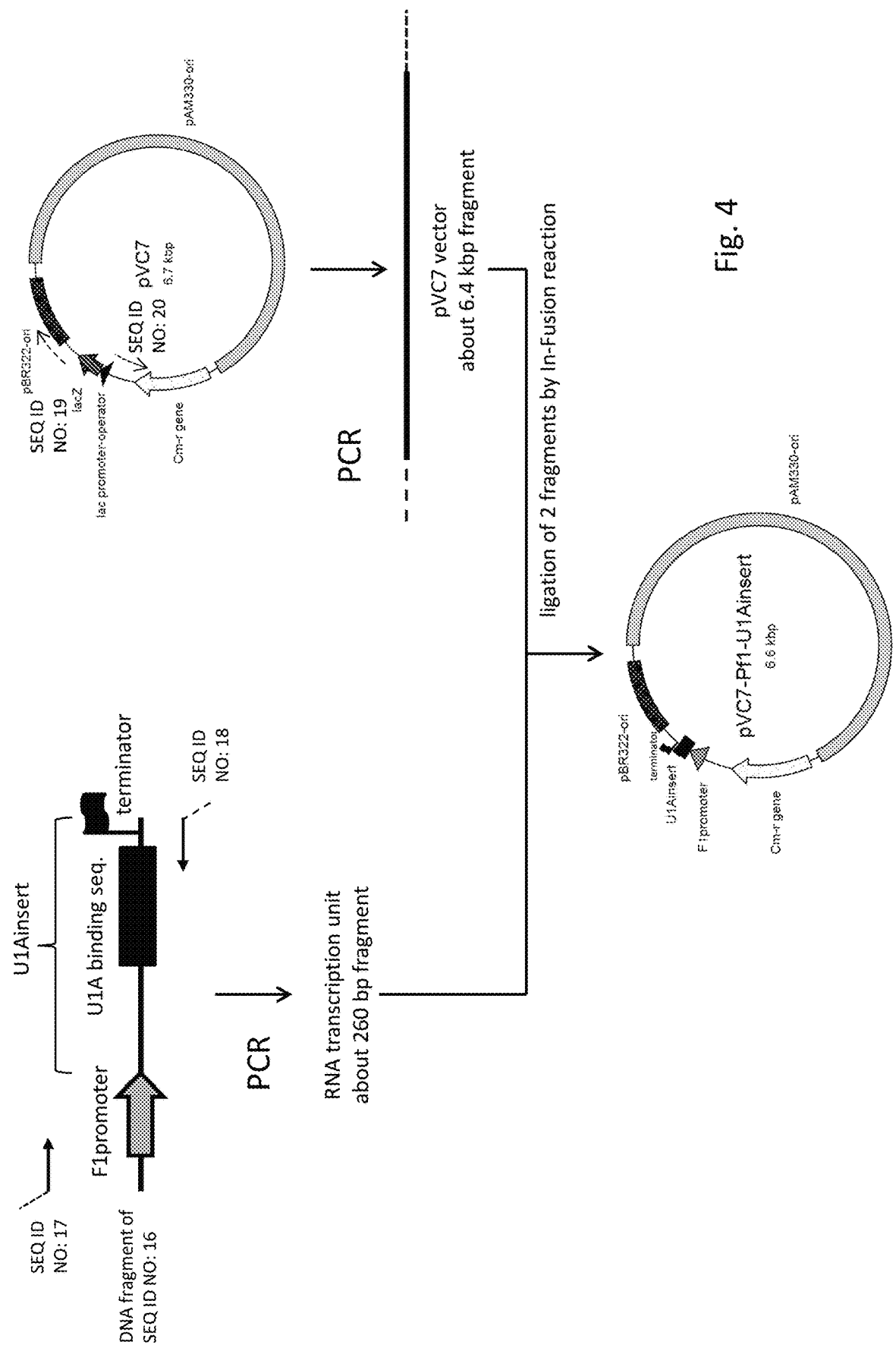
FIG. 4 shows a diagram of the construction scheme of plasmid pVC7-Pf1-U1Ainsert.

A promoter functional region (SEQ ID NO: 13; also referred to as "F1 promoter"; Koptides, M., et al., (1992). Characterization of bacteriophage BFK20 from *Brevibacterium flavum*. Microbiology, 138(7), 1387-1391) from the promoter sequence (Accession No. L13772) of a bacteriophage BFK20, which is infectious to coryneform bacteria, a terminator (ter) region of the same (SEQ ID NO: 14; Bukovska, G., et al., (2006). Complete nucleotide sequence and genome analysis of bacteriophage BFK20-a lytic phage of the industrial producer *Brevibacterium flavum*. Virology, 348(1), 57-71.), and the U1A-binding sequence as objective RNA (SEQ ID NO: 15, in which "T" should be read as "U"; Endoh, T., et al., (2008). Cellular siRNA delivery mediated by a cell-permeant RNA-binding protein and photoinduced RNA interference. Bioconjugate chemistry, 19(5), 1017-1024.), which has a binding capacity to a small nucleolar ribonucleoprotein U1A, were chosen, and a DNA sequence of a transcription unit for the U1A-binding sequence (U1Ainsert RNA transcription unit; SEQ ID NO: 16) was designed (FIG. 4). A DNA fragment of the U1Ainsert RNA transcription unit was prepared by chemical synthesis (Eurofins Genomics). Then, PCR amplification was performed by using the DNA fragment as the template, primers of SEQ ID NOS: 17 and 18, and KOD FX NEO (TOYOBO) to obtain an amplified fragment of the U1Ainsert RNA transcription unit. Separately, PCR amplification was performed by using pVC7 as the template, primers of SEQ ID NOS: 19 and 20, and KOD FX NEO (TOYOBO) to obtain an amplified fragment of pVC7. These amplified fragments were mixed, and mutually ligated by using In-Fusion HD Cloning Kit (Clontech). Then, competent cells of the *Escherichia coli* JM109 strain (TAKARA BIO) were transformed with the reaction mixture, applied to LB agar medium containing 25 µg/mL of chloramphenicol, and cultured at 37° C. overnight. Then, single colonies were isolated from colonies that appeared to obtain transformants. Plasmids were extracted from the obtained transformants in the usual manner. An objective plasmid was identified by DNA sequencing analysis, and designated as pVC7-Pf1-U1Ainsert (FIG. 4).

<4> Construction of Dual-Direction Transcription Plasmid pVC7-Pf1-Hv-Iap-Pf1rev

A plasmid, pVC7-Pf1-Hv-iap-Pf1rev, for transcription of Hv-iap RNA as objective RNA under control of F1 promoter in dual directions was constructed in the following manner.

Figure 5A:
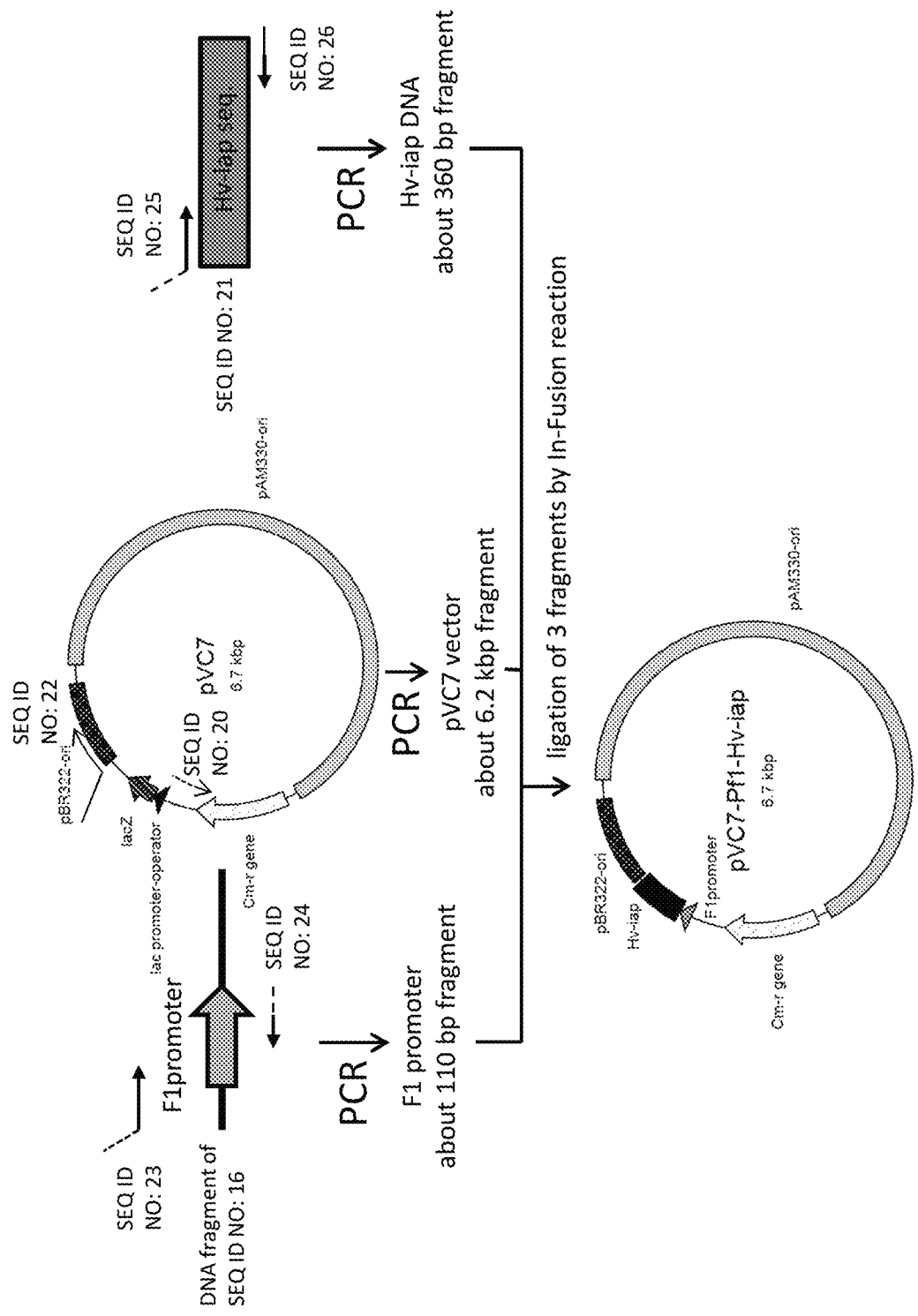
FIG. 5A shows the construction scheme of plasmid pVC7-Pf1-Hv-iap.

A DNA fragment of Hv-iap (SEQ ID NO: 21), which is a partial sequence of cDNA of an iap gene encoding an inhibitor of apoptosis protein IAP of *Henosepilachna vigintioctopunctata*, was prepared by chemical synthesis on the basis of information described in WO2010/140675. There was constructed a plasmid containing a DNA sequence containing the F1 promoter and the Hv-iap sequence ligated immediately downstream thereof in the following manner (FIG. 5A). First, PCR amplification was performed by using pVC7 as the template, primers of SEQ ID NOS: 20 and 22, and KOD FX NEO (TOYOBO) to obtain an amplified fragment of pVC7. Separately, PCR amplification was performed by using the DNA fragment of SEQ ID NO: 16 as the template, primers of SEQ ID NOS: 23 and 24, and PrimeSTAR HS (TAKARA BIO) to obtain a DNA fragment containing the F1 promoter sequence. Separately, PCR amplification was performed by using the DNA fragment of SEQ ID NO: 21 as the template, primers of SEQ ID NOS: 25 and 26, and PrimeSTAR HS (TAKARA BIO) to obtain a DNA fragment of the Hv-iap sequence. These three DNA fragments were mixed, and mutually ligated by using In-Fusion HD Cloning Kit (Clontech). Then, competent cells of the *Escherichia coli* JM109 strain (TAKARA BIO) were transformed with the reaction mixture, and strains resistant to 25 µg/mL of chloramphenicol were obtained. Plasmids were extracted from the obtained transformants in the usual manner. Objective plasmids were identified by DNA sequencing analysis, and one of them was designated as pVC7-Pf1-Hv-iap (FIG. 5A).

Figure 5B:
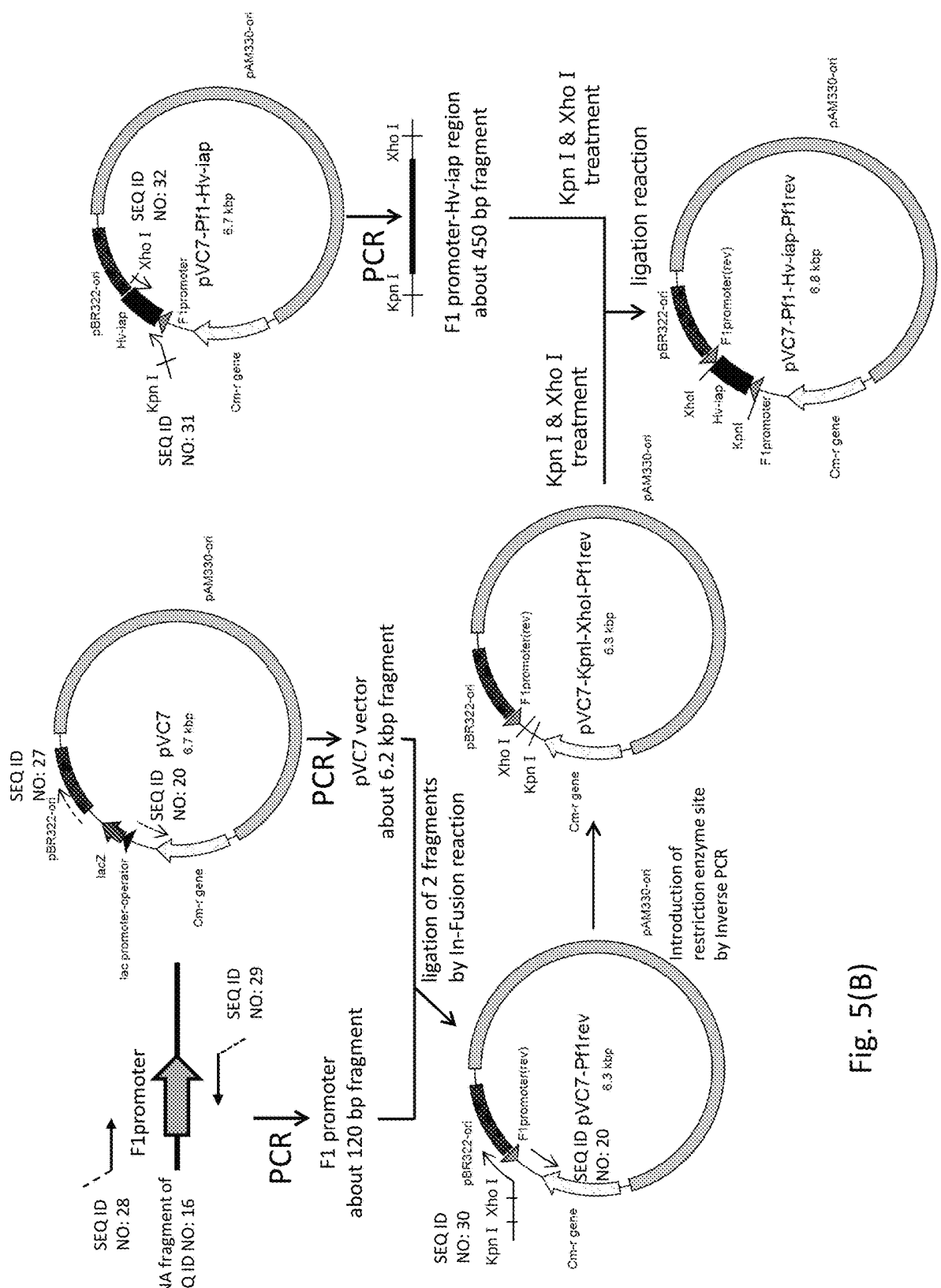
FIG. 5B shows the construction scheme of plasmid pVC7-Pf1-Hv-iap-Pf1rev.

PCR amplification was performed by using pVC7 as the template, primers of SEQ ID NOS: 20 and 27, and KOD FX NEO (TOYOBO) to obtain an amplified fragment of pVC7. Separately, PCR amplification was performed by using the DNA fragment of SEQ ID NO: 16 as the template, primers of SEQ ID NOS: 28 and 29, and PrimeSTAR HS (TAKARA BIO) to obtain an amplified fragment of the F1 promoter sequence. Both the amplified fragments were mixed, and mutually ligated by using In-Fusion HD Cloning Kit (Clontech). Then, competent cells of the *Escherichia coli* JM109 strain (TAKARA BIO) were transformed with the reaction mixture, applied to LB agar medium containing 25 µg/mL of chloramphenicol, and cultured at 37° C. overnight. Then, single colonies were isolated from colonies that appeared. Plasmids were extracted from the obtained transformants in the usual manner. An objective plasmid was identified by DNA sequencing analysis, and designated as pVC7-Pf1rev (FIG. 5B).

Next, in order to introduce restriction enzyme sites KpnI and XhoI downstream of the F1 promoter of pVC7-Pf1rev, inverse PCR was performed by using pVC7-Pf1rev as the template, primers of SEQ ID NOS: 20 and 30, and KOD-Plus-Mutagenesis Kit (TOYOBO). Then, the amplified DNA fragment was subject to DpnI treatment, phosphorylation reaction, and self-ligation reaction to thereby be cyclized, and introduced into competent cells of the *Escherichia coli* JM109 strain (TAKARA BIO). The cells were applied to LB agar medium containing 25 μg/mL of chloramphenicol, and cultured at 37° C. overnight. Then, single colonies were isolated from colonies that appeared. Plasmids were extracted from the obtained transformants in the usual manner. An objective plasmid was identified by DNA sequencing analysis, and designated as pVC7-KpnI-XhoI-Pf1rev (FIG. 5B).

Then, PCR was performed by using pVC7-Pf1-Hv-iap as the template, primers of SEQ ID NOS: 31 and 32, and PrimeSTAR HS (TAKARA BIO) to obtain a DNA fragment containing the KpnI restriction enzyme site, F1 promoter region, Hv-iap region, and XhoI restriction enzyme site in this order. This DNA fragment and pVC7-KpnI-XhoI-Pf1rev were each digested with restriction enzymes KpnI and XhoI, and purified with MinElute PCR Purification Kit (QIAGEN). Both the purified products were mixed, and mutually ligated by a ligation reaction using Ligation high Ver.2 (TOYOBO). Then, competent cells of the *Escherichia coli* JM109 strain (TAKARA BIO) were transformed with the reaction mixture, and strains resistant to 25 μg/mL of chloramphenicol were obtained. Plasmids were extracted from the obtained transformants in the usual manner. An objective plasmid was identified by DNA sequencing analysis, and designated as pVC7-Pf1-Hv-iap-Pf1rev (FIG. 5B).

<5> Production of Objective RNA

The *C. glutamicum* strains 2256ΔpAM330 and 2256ΔrncΔpAM330 were introduced with each of the plasmids pVC7, pVC7-Pf1-U1Ainsert, and pVC7-Pf1-Hv-iap-Pf1rev by the electric pulse method, applied to CM-Dex agar medium containing 5 μg/mL of chloramphenicol, and cultured at 30° C. overnight. Thereby, transformant strains 2256ΔpAM330/pVC7 and 2256ΔrncΔpAM330/pVC7, 2256ΔpAM330/pVC7-Pf1-U1Ainsert and 2256ΔrncΔpAM330/pVC7-Pf1-U1Ainsert, and 2256ΔpAM330/pVC7-Pf1-Hv-iap-Pf1rev and 2256ΔrncΔpAM330/pVC7-Pf1-Hv-iap-Pf1rev were obtained.

Colonies of the transformants obtained above were each spread on CM-Dex agar medium containing 5 μg/mL of chloramphenicol, and cultured at 30° C. for about 16 hr. Then, a part of the cultured cells was used for test-tube culture. Culture was carried out in 2 mL of CM-Dex medium containing 5 μg/mL of chloramphenicol at 30° C. with shaking for 24 hr. Then, 200 μL of the culture broth was treated with RNAprotect Bacteria Reagent, and the supernatant was removed. Then, 225 μL of TE buffer containing 15 mg/mL of lysozyme (SIGMA) was added thereto to perform a reaction at the room temperature for 30 min, 25 μL of 20 mg/mL proK (TAKARA BIO) was further added thereto to perform a reaction at the room temperature for 30 min, and then, RNA was extracted with TRIzol LS (Thermo Fisher Scientific). The extracted RNA was dissolved with 50 μL of RNase-free water to prepare a total RNA solution. The obtained total RNA solutions were subject to total RNA analysis using Novex TBE Gels, 6% (Thermo Fisher Scientific). That is, 1 μL each of the total RNA solutions was applied to a lane of the gel, and poly-acrylamide gel electrophoresis (PAGE) was performed under non-denaturing conditions.

As a result, when comparing the total RNAs extracted from the strains 2256ΔpAM330/pVC7-Pf1-U1Ainsert and 2256ΔrncΔpAM330/pVC7-Pf1-U1Ainsert, an RNA band derived from U1Ainsert was confirmed at a predicted position only for the strain deficient in the rnc gene (FIG. 6). Similarly, also when comparing the total RNAs extracted from the strains 2256ΔpAM330/pVC7-Pf1-Hv-iap-Pf1rev and 2256ΔrncΔpAM330/pVC7-Pf1-Hv-iap-Pf1rev, an RNA band derived from Hv-iap was confirmed at a predicted position only for the strain deficient in the rnc gene (FIG. 6). Thus, it was shown that deletion of the rnc gene is effective for RNA production using *Corynebacterium* bacteria.

<6> Acquisition of High Copy Number Variation Plasmids

Sixty clones of a transformant 2256/pVC7 were each cultured in CM-Dex medium containing 5 μg/mL of chloramphenicol overnight. A 500-4, aliquot of the culture broth was centrifuged (14,400×g, 2 min), and the collected cells were added with 200 μL of 15 mg/mL lysozyme from chicken egg white (Sigma-Aldrich) dissolved in P1 buffer (QIAGEN) to perform a reaction at 37° C. for 30 min. Then, plasmid was extracted from cells of each of the clones with QIAprep Spin Miniprep Kit (QIAGEN), and subject to agarose gel electrophoresis to compare the plasmid amounts. As a result, it was observed that a plasmid extracted from one of the clones provides a DNA band clearly bolder than those extracted from the other clones. Hence, this plasmid was anew introduced into the 2256 strain, the plasmid was similarly extracted from the transformant, and the yield amount thereof was analyzed by agarose gel electrophoresis. As above, this plasmid provides a DNA band clearly bolder than that of pVC7 as a control, and that is, it was revealed that this plasmid is a plasmid maintained at a high copy number in cells of coryneform bacteria as compared with the original plasmid pVC7. This plasmid was designated as pVC7H1.

The mutation site of the obtained pVC7H1 was analyzed with a DNA sequencer, Genetic Analyzer 3500xl (Applied Biosystems). As a result, it was revealed that, in pVC7H1, the $1172^{nd}$ nucleotide of the total 6679 bp nucleotide sequence of pVC7 has been mutated from cytosine (C) to adenine (A), in which the nucleotide A at $2^{nd}$ position counted from the 5' terminus of the digestion recognition site of the restriction enzyme HindIII is regarded as "+1". Hereinafter, this mutation is referred to as "C1172A". Thus, it was revealed that this mutation is a cause of high copy number variation of pVC7H1.

Because it was revealed that the C1172A mutation significantly increases the copy number of pVC7, the mutations at this region shown in Table 1 were each introduced into pVC7, and effect of these mutations on the copy number of the plasmid was evaluated.

The mutant plasmids were each constructed with KOD-Plus-Mutagenesis Kit (TOYOBO). There were constructed pVC7H2 by using primers of SEQ ID NOS: 33 and 34, pVC7H3 by using primers of SEQ ID NOS: 33 and 35, pVC7H4 by using primers of SEQ ID NOS: 36 and 37, pVC7H5 by using primers of SEQ ID NOS: 36 and 38, pVC7H6 by using primers of SEQ ID NOS: 33 and 39, and pVC7H7 by using primers of SEQ ID NOS: 33 and 40, in combination with the plasmid pVC7 as the template, according to the construction protocol attached to the kit (Table 1). The total nucleotide sequences thereof were confirmed to be correct with a DNA sequencer.

TABLE 1 pVC7 mutant plasmids

| No. | Plasmid name | Type of mutation | Nucleotide sequence (mutation name) 5'-CTACCAA-3' (wild-type) |
|---|---|---|---|
| 1 | PVC7H2 | Single-nucleotide substitution | 5'-CTACGAA-3' (C1172G mutation) |
| 2 | PVC7H3 | Single-nucleotide substitution | 5'-CTACTAA-3' (C1172T mutation) |
| 3 | PVC7H4 | Single-nucleotide substitution | 5'-CTAACAA-3' (C1171A mutation) |
| 4 | pVC7H5 | Two-nucleotide substitution | 5'-CTAAAAA-3' (C1171A, C1172A mutation) |
| 5 | PVC7H6 | Single-nucleotide deletion | 5'-CTAC*AA-3' (C1172Δ mutation) |
| 6 | PVC7H7 | Two-nucleotide deletion | 5'-CTAC ** A-3' (C1172Δ, A1173Δ mutation) |

In the nucleotide sequences, nucleotide(s) different from that/those of the wild-type was/were underlined, and deletion site(s) was/were represented by "*".

The constructed plasmids were each transformed into the 2256ΔpAM330 strain in the usual manner. CM-Dex agar medium containing 5 μg/mL of chloramphenicol was used as the selection medium. Colonies were well formed in cases of transformation of any of the plasmids. Hence, colonies harboring the respective plasmids were each inoculated into the same agar medium with an inoculation loop, and cultured at 30° C. for about 1 day. Then, grown cells of each strain in an amount of about 2-cm-square region were inoculated into CM-Dex medium containing 5 μg/mL of chloramphenicol, and cultured at 30° C. with shaking overnight.

The harbored plasmid was extracted from each culture broth in the usual manner. A part of the prepared plasmid solution was subject to agarose gel electrophoresis to analyze the DNA band of each plasmid. The results are shown in Table 2.

TABLE 2

Band intensity of plasmids on electrophoretogram

| No. | Plasmid name | Intensity of DNA band *1 |
|---|---|---|
| 1 | pVC7H2 | ++++++ |
| 2 | pVC7H3 | ++++ |
| 3 | pVC7H4 | ++++++ |
| 4 | pVC7H5 | +++++ |
| 5 | PVC7H6 | ++++ |
| 6 | pVC7H7 | +++ |
| 7 | pVC7H1 | ++++ |
| 8 | pVC7 | + |

*1: Each plasmid was extracted from cells harboring the plasmid, and the intensity of the DNA band thereof was evaluated by visual observation in agarose gel electrophoresis. A larger number of "+" indicates a larger yield amount of plasmid.

As a result, there were obtained mutant plasmids of which the copy numbers are apparently higher than that of the originally-obtained pVC7H1. One of them, pVC7H2, was used for the following experiments. It is estimated that the copy number of pVC7 is about 10 copies/cell, the copy number of pVC7H1 is about 100 copies/cell, and the copy number of pVC7H2 is about 250 copies/cell.

<7> RNA Production Using High Copy Number Variation Plasmids

High copy number variations of pVC7-Pf1-U1Ainsert and pVC7-Pf1-Hv-iap-Pf1rev were constructed in the following manner. Specifically, inverse PCR was performed by using pVC7-Pf1-U1Ainsert or pVC7-Pf1-Hv-iap-Pf1rev as the template, primers of SEQ ID NOS: 33 and 41 for introduction of pVC7H1 mutation or primers of SEQ ID NOS: 33 and 34 for introduction of pVC7H2 mutation, and KOD-Plus-Mutagenesis Kit (TOYOBO). Then, the obtained DNA fragments were subject to DpnI treatment, phosphorylation reaction, and self-ligation reaction to thereby be cyclized, and transformed into competent cells of the *Escherichia coli* JM109 strain (TAKARA BIO). The cells were applied to LB agar medium containing 25 μg/mL of chloramphenicol, and cultured at 37° C. overnight. Then, single colonies were isolated from colonies that appeared to obtain transformants. Plasmids were extracted from the obtained transformants in the usual manner. Objective plasmids were identified by DNA sequencing analysis, and designated as pVC7H1-Pf1-U1Ainsert, pVC7H2-Pf1-U1Ainsert, pVC7H1-Pf1-Hv-iap-Pf1rev, and pVC7H2-Pf1-Hv-iap-Pf1rev.

Figure 7:
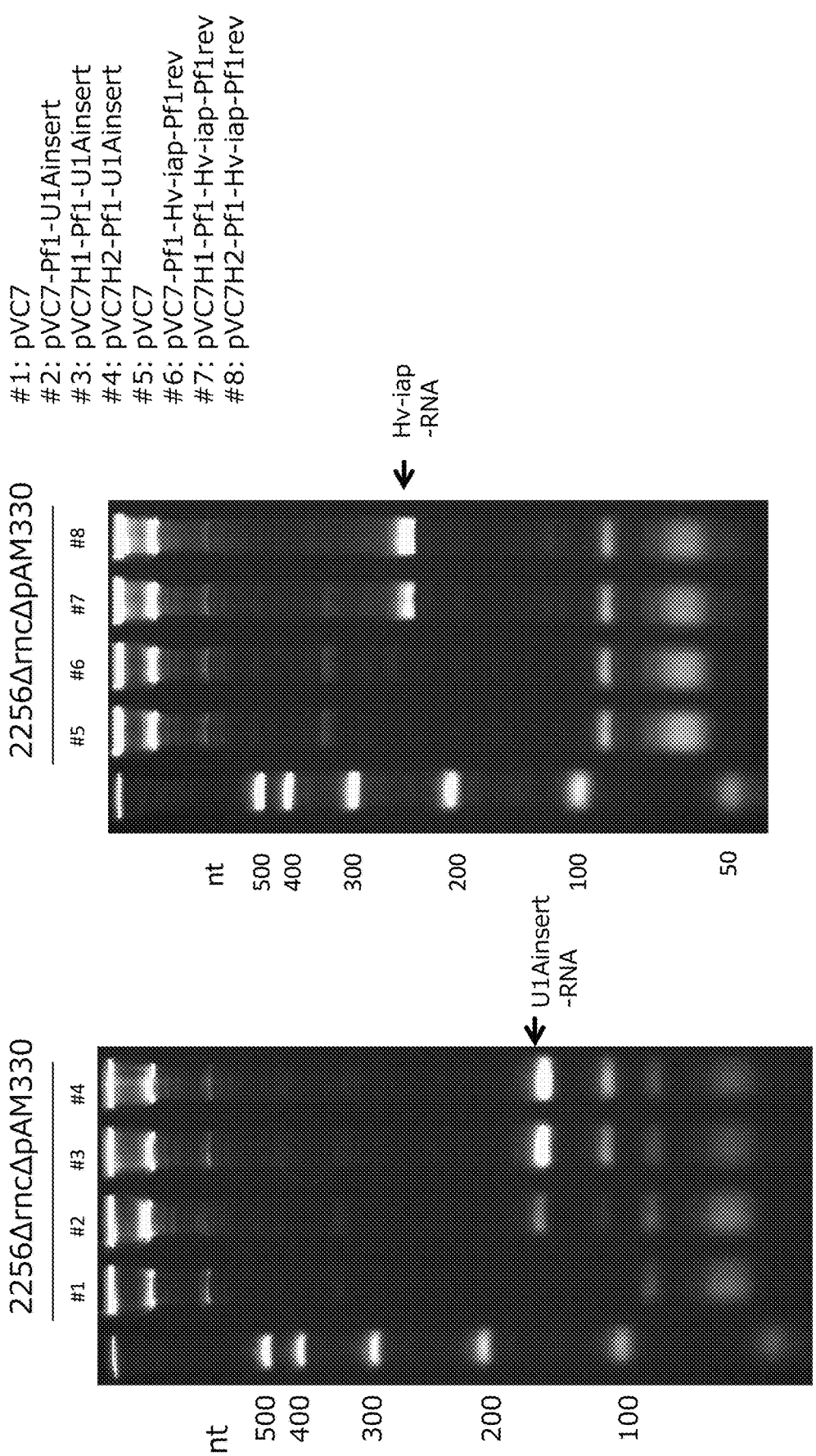
FIG. 7 shows agarose gel electrophoretograms (photographs) showing an improved effect in RNA production due to high copy number variations of RNA expression plasmid.

Next, the 2256ΔrncΔpAM330 strain was introduced with each of the plasmids pVC7, pVC7-Pf1-U1Ainsert, pVC7H1-Pf1-U1Ainsert, pVC7H2-Pf1-U1Ainsert, pVC7-Pf1-Hv-iap-Pf1rev, pVC7H1-Pf1-Hv-iap-Pf1rev, and pVC7H2-Pf1-Hv-iap-Pf1rev by the electric pulse method, applied to CM-Dex agar medium containing 5 μg/mL of chloramphenicol, and cultured at 30° C. overnight. Thereby, transformant strains 2256ΔrncΔpAM330/pVC7, 2256ΔrncΔpAM330/pVC7-Pf1-U1Ainsert, 2256ΔrncΔpAM330/pVC7H1-Pf1-U1Ainsert, 2256ΔrncΔpAM330/pVC7H2-Pf1-U1Ainsert, 2256ΔrncΔpAM330/pVC7-Pf1-Hv-iap-Pf1rev, 2256ΔrncΔpAM330/pVC7H1-Pf1-Hv-iap-Pf1rev, and 2256ΔrncΔpAM330/pVC7H2-Pf1-Hv-iap-Pf1rev were obtained. Then, these strains were each cultured in a test tube, and RNA produced by the strains was evaluated. A part of cells cultured on the agar medium from a colony of each of the transformants was inoculated into 2 mL of CM-Dex medium containing 5 μg/mL of chloramphenicol, and cultured at 30° C. with shaking for 24 hr. Then, RNA was extracted from 200 µL of the culture broth in the same manner including RNAprotect Bacteria Reagent treatment as the above-mentioned Example, and finally the RNA sample was dissolved with 50 µL of RNase-free water to prepare a total RNA solution. The obtained total RNA solutions were subject to total RNA analysis by PAGE under non-denaturing conditions using Novex TBE Gels (6%). As a result, the accumulation amount of U1Ainsert-RNA was increased in the order of pVC7-Pf1-U1Ainsert<<pVC7H1-Pf1-U1Ainsert approximately equal to pVC7H2-Pf1-U1Ainsert (FIG. 7). Similarly, the accumulation amount of Hv-iap-dsRNA was increased in the order of pVC7-Pf1-Hv-iap-Pf1rev<<<pVC7H1-Pf1-Hv-iap-Pf1rev<pVC7H2-Pf1-Hv-iap-Pf1rev (FIG. 7). Thus, it was shown that the intracellular accumulation amount of objective RNA is increased by increasing the copy number of a plasmid for transcription of the RNA.

<8> Comparison with RNA Production by T7-Promoter-Induced-Expression System in *E. coli*

As described previously (Timmons, L., Court, D. L., & Fire, A. (2001). Ingestion of bacterially expressed dsRNAs can produce specific and potent genetic interference in *Caenorhabditis elegans*. Gene, 263(1), 103-112.), there has been reported an RNA production system using T7 RNA polymerase in the *Escherichia coli* HT115(DE3) strain, which is a rnc gene deficient strain. Hence, a comparison was performed between RNA production by F1-promoter-expression system in the *C. glutamicum* 2256ΔrncΔpAM330 strain and RNA production by T7-promoter-induced-expression system in *E. coli*.

For this, a plasmid, pL4440-Pt7-U1Ainsert, for transcription of the U1A-binding sequence under control of T7 promoter in a single direction, and a plasmid, pL4440-Pt7-Hv-iap-Pt7rev, for transcription of Hv-iap RNA under control of T7 promoter in dual directions were constructed in the following manner.

Figure 8:
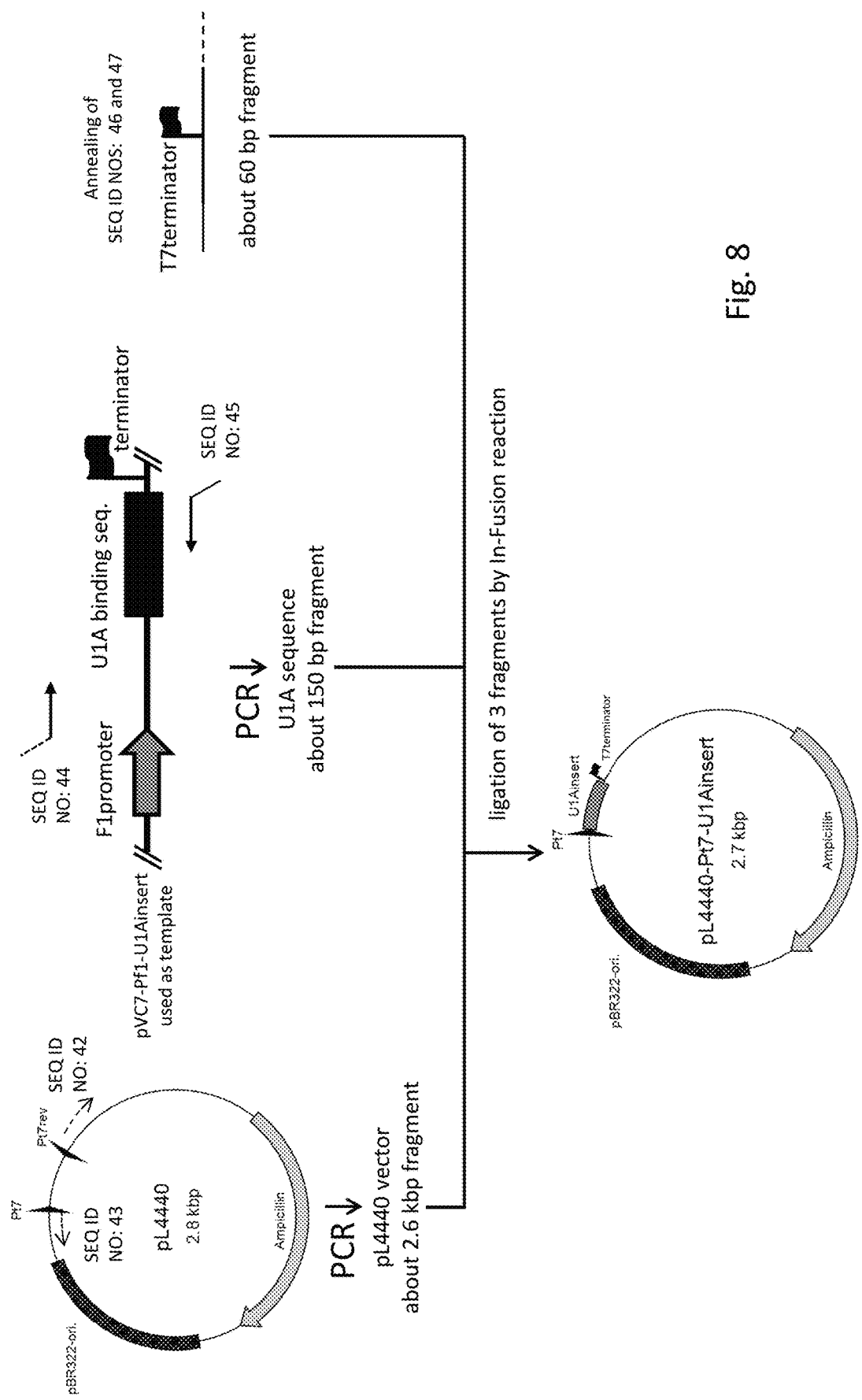
FIG. 8 shows a diagram of the construction scheme of plasmid pL4440-Pt7-U1Ainsert.

PCR was performed by using a plasmid pL4440 (GE Healthcare) as the template, primers of SEQ ID NOS: 42 and 43, and KOD FX NEO to obtain a DNA fragment of pL4440. Separately, PCR was performed by using pVC7-Pf1-U1Ainsert as the template, primers of SEQ ID NOS: 44 and 45, and PrimeSTAR HS (TAKARA BIO) to obtain a DNA fragment containing the U1Ainsert sequence. Separately, a DNA chain of SEQ ID NO: 46 and a DNA chain of SEQ ID NO: 47, wherein the DNA chain of SEQ ID NO: 47 has a sequence corresponding to the complementary sequence of the DNA chain of SEQ ID NO: 46, were mixed and mutually annealed, and purified with MinElute PCR Purification Kit to obtain a DNA fragment of the T7 terminator sequence. These three DNA fragments were mixed, and mutually ligated by using In-Fusion HD Cloning Kit. Then, competent cells of the *Escherichia coli* JM109 strain were transformed with the reaction mixture, applied to LB agar medium containing 100 µg/mL of ampicillin, and cultured at 37° C. overnight. Then, single colonies were isolated from colonies that appeared. Plasmids were extracted from the obtained transformants in the usual manner. Objective plasmids were identified by DNA sequencing analysis, and one of them was designated as pL4440-Pt7-U1Ainsert (FIG. 8).

Figure 9:
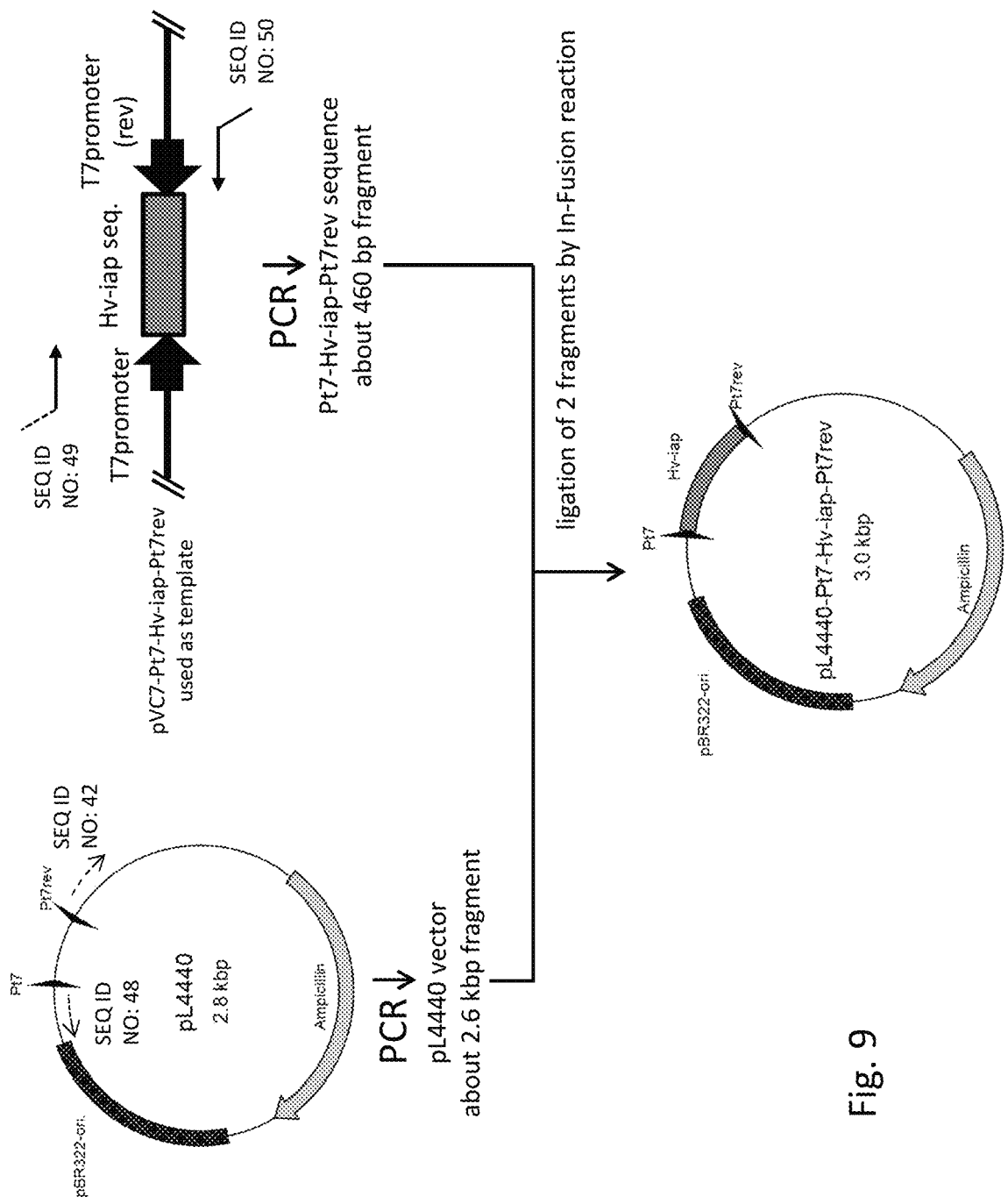
FIG. 9 shows a diagram of the construction scheme of plasmid pL4440-Pt7-Hv-iap-Pt7rev.

PCR was performed by using the plasmid pL4440 as the template, primers of SEQ ID NOS: 42 and 48, and KOD FX NEO to obtain a DNA fragment of pL4440. Separately, PCR was performed by using a plasmid pVC7-Pt7-Hv-iap-Pt7rev (described below in Example <9> (2-2)) as the template, primers of SEQ ID NOS: 49 and 50, and KOD FX NEO to obtain a DNA fragment of the "Pt7-Hv-iap-Pt7rev" region. These DNA fragments were mixed, and mutually ligated by using In-Fusion HD Cloning Kit. Then, competent cells of the *Escherichia coli* JM109 strain were transformed with the reaction mixture, applied to LB agar medium containing 100 µg/mL of ampicillin, and cultured at 37° C. overnight. Then, single colonies were isolated from colonies that appeared to obtain transformants. Plasmids were extracted from the obtained transformants in the usual manner. Objective plasmids were identified by DNA sequencing analysis, and one of them was designated as pL4440-Pt7-Hv-iap-Pt7rev (FIG. 9).

Figure 10:
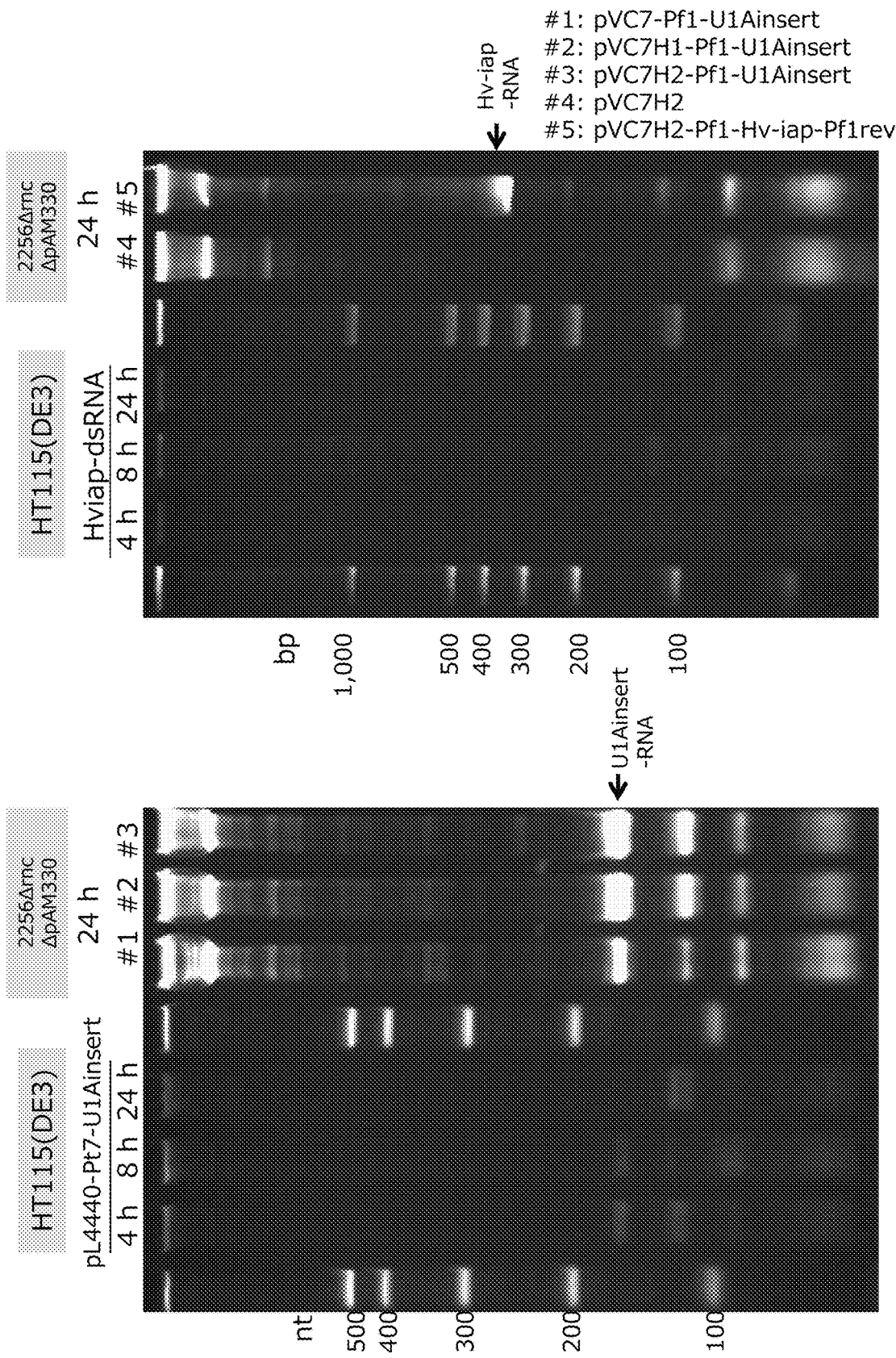
FIG. 10 shows agarose gel electrophoretograms (photographs) showing a comparison between RNA production amounts observed for F1-promoter-expression system in *C. glutamicum* and those observed for T7-promoter-induced-expression system in *E. coli*.

The *E. coli* HT115(DE3) strain was introduced with each of pL4440-Pt7-U1Ainsert and pL4440-Pt7-Hv-iap-Pt7rev by the electric pulse method to obtain transformant strains HT115(DE3)/pL4440-Pt7-U1Ainsert and HT115(DE3)/pL4440-Pt7-Hv-iap-Pt7rev. The strains were each cultured in LB liquid medium containing 100 µg/mL of ampicillin in a test tube at 37° C. with shaking overnight to prepare a seed culture broth. Next, the seed culture broth was added to LB liquid medium containing 100 µg/mL of ampicillin in a volume of 1/50 of the medium to start main culture at 37° C. After 3 hr culture with shaking, IPTG was added thereto at a final concentration of 1 mM, culture was further continued, and sampling was carried out at 4 hr, 8 hr, and 24 hr after addition of IPTG. A 200-4, aliquot of the culture broth was centrifuged (13,800×g, 2 min) to collect cells. RNA was extracted with TRIzol (Thermo Fisher Scientific) according to the protocol thereof, and dissolved with 50 µL of RNase-free water to prepare a total RNA solution. For comparison, the total RNA solution of *C. glutamicum* obtained in Example <7> was used. PAGE was carried out under non-denaturing conditions by using Novex TBE Gels (6%) and 1 µL each of the RNA samples. As a result, the amount of U1Ainsert-ssRNA produced by F1-promoter-expression system in the *C. glutamicum* was larger than the amount of U1Ainsert-ssRNA produced by T7-promoter-induced-expression system in *E. coli* (FIG. 10). Similarly, the amount of Hv-iap-dsRNA produced by F1-promoter-expression system in the *C. glutamicum* was larger than the amount of Hv-iap-dsRNA produced by T7-promoter-induced-expression system in *E. coli* (FIG. 10). Hence, it was revealed that coryneform bacteria such as *C. glutamicum* are useful for production of objective RNA.

<9> RNA Production by T7-Promoter-Induced-Expression System in *C. glutamicum*

(1) Production of Hairpin Like Structured RNA (1-1) Construction of Plasmid pPK-T7lac-vd-antiOlac for Transcription of Hairpin Like Structured RNA A plasmid, pPK-T7lac-vd-antiOlac, for transcription of a hairpin like structured RNA as objective RNA under control of T7 promoter in a single direction was constructed in the following manner.

(1-1-1) Construction of pUC57-VD

A DNA fragment of SEQ ID NO: 53 encoding the hairpin like structured RNA was prepared by chemical synthesis based on the genome sequence of a potato spindle tuber viroid (PSTVd).125 (Mol Biol (Mosk). 2013 January-February; 47(1):94-106). The DNA fragment was cloned into pUC57 (ATG Servis-Gen, St. Petersburg, Russia) to construct pUC57-VD.

(1-1-2) Construction of pPK-T7lac

At first, a fragment (131 bp) containing terminator T7 (TT7) was amplified from pET22b(+) (Novagen) with primers of SEQ ID NOS: 54 and 55 by PCR. Then, the fragment was digested with KpnI and SalI, and cloned into pPK4

Figure 11:
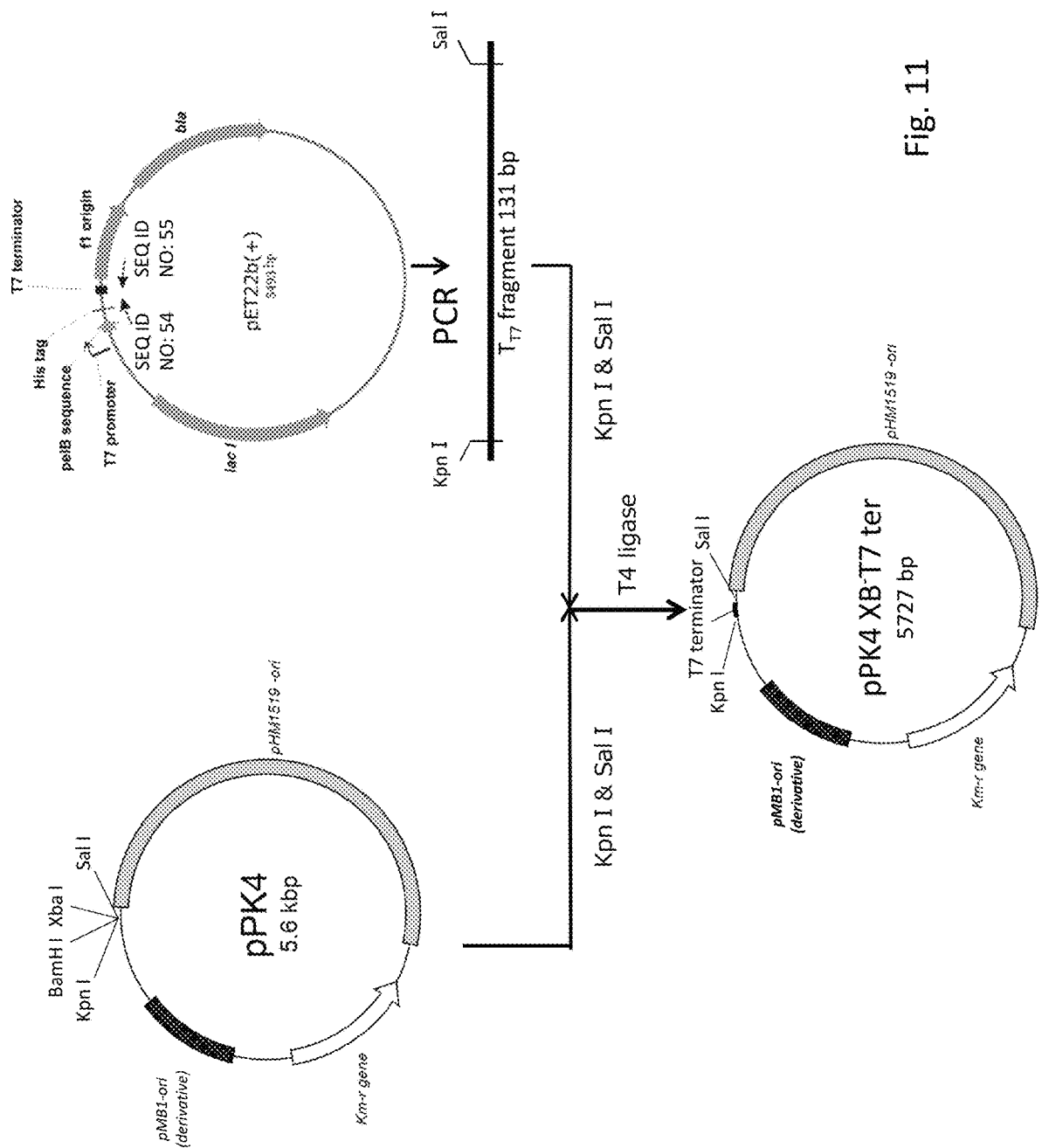
FIG. 11 shows a diagram of the construction scheme of plasmid pPK4 XB⁻T7 ter.

(U.S. Pat. No. 6,090,597) linearized by the same restriction enzymes. The constructed plasmid was named pPK4 XB⁻T7 ter (FIG. 11).

Figure 12:
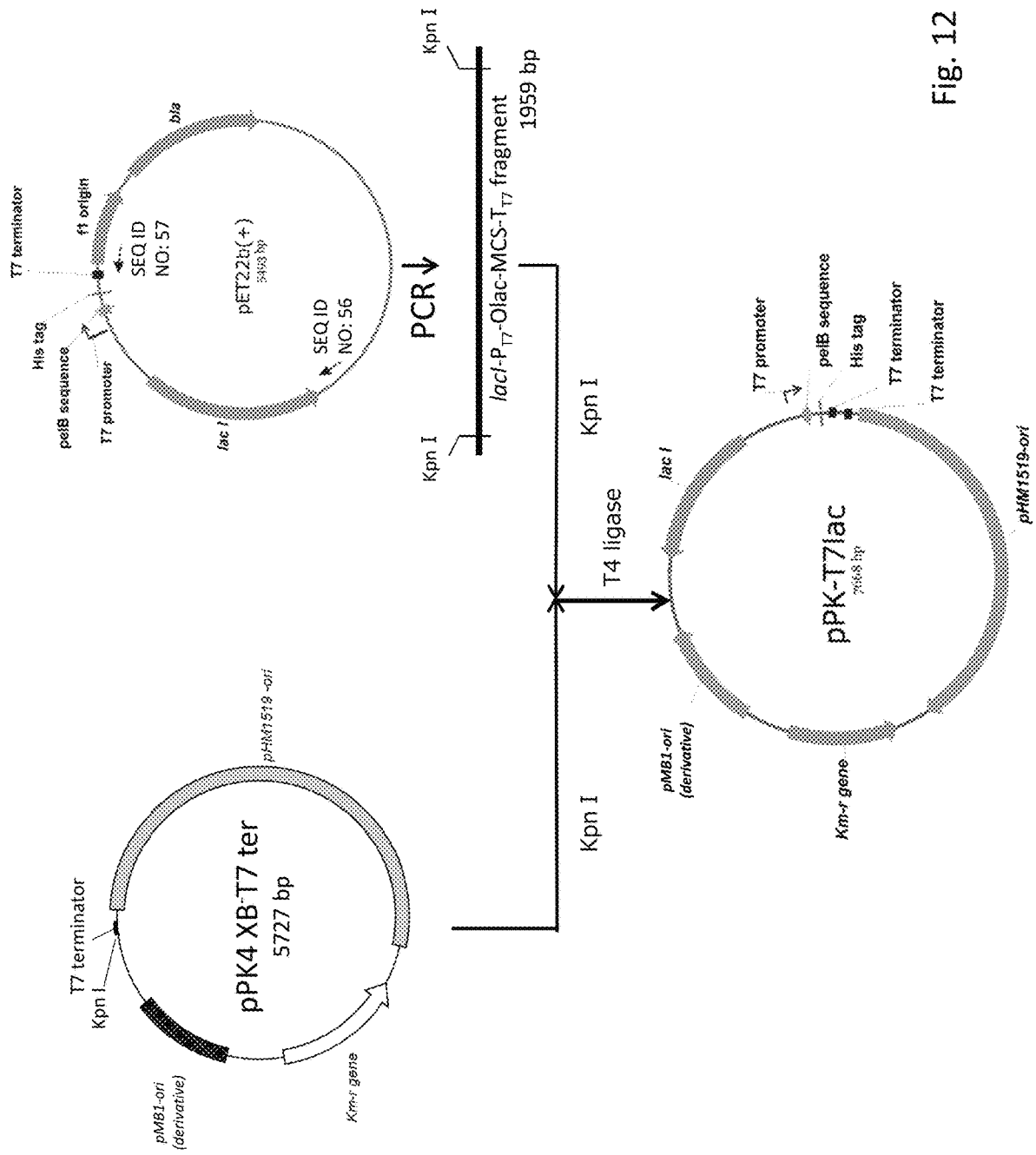
FIG. 12 shows a diagram of the construction scheme of plasmid pPK-T7lac.

Then, another fragment (1959 bp) containing DNA region of lacI-P$_{77}$-Olac-MCS-TT7 was amplified from pET22b(+) with primers of SEQ ID NOS: 56 and 57 by PCR. The amplified fragment was digested with KpnI, and cloned into pPK4 XB⁻T7 ter linearized by KpnI. The constructed plasmid was named pPK-T7lac (FIG. 12).

(1-1-3) Construction of pPK-T7lac-vd-antiOlac

Figure 13:
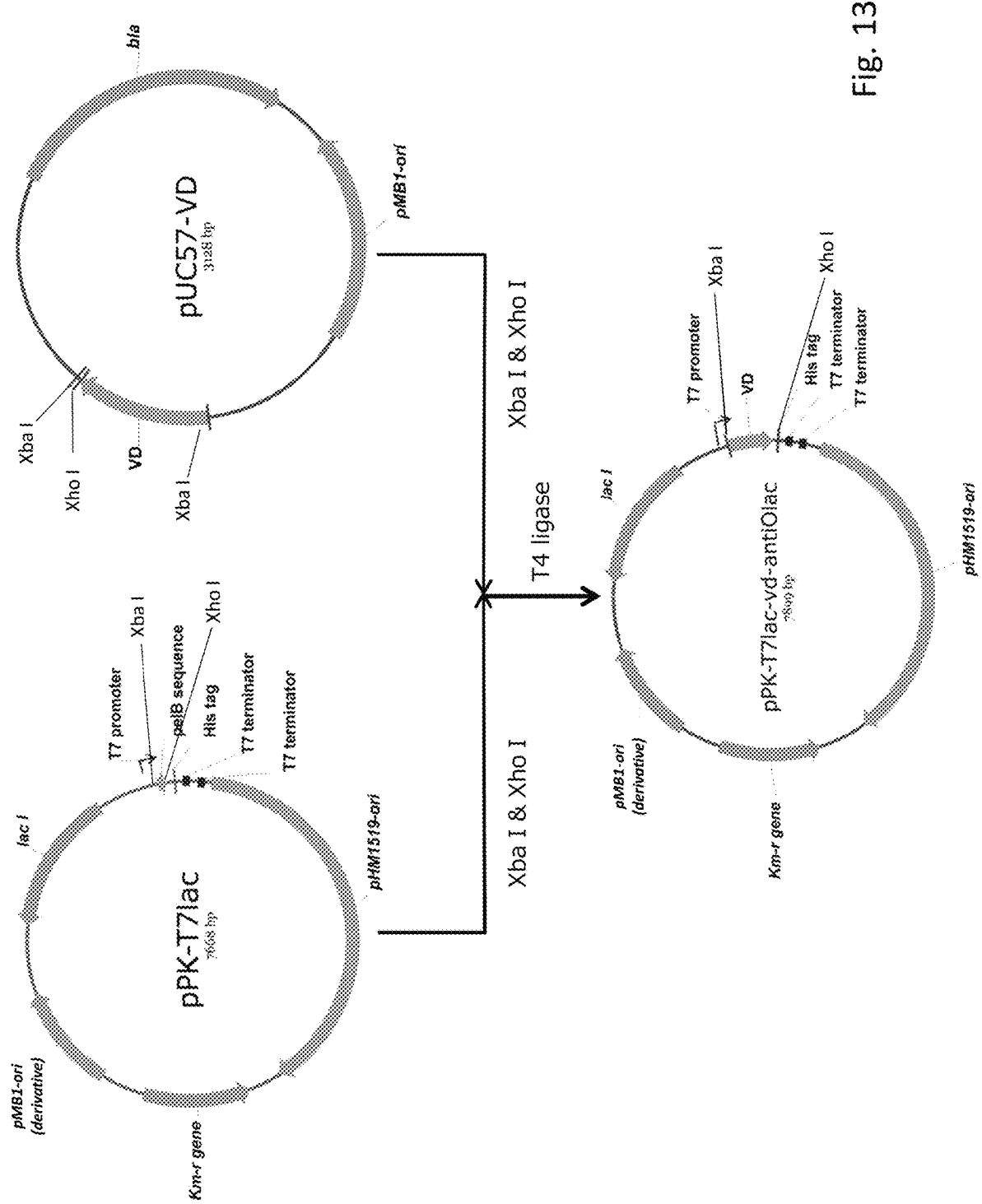
FIG. 13 shows a diagram of the construction scheme of plasmid pPK-T7lac-vd-antiOlac.

A DNA fragment VD-aOlac was cut out from pUC57-VD with XbaI and XhoI, and cloned into pPK-T7lac with T4DNA ligase. The ligation mixture was transformed into competent cells of the *E. coli* LE392 strain (Promega) by electroporation. Standard electroporation procedure for *E. coli* cells was applied. After growth of cells for 1.5 hr at 37° C., the cells were seeded on LB agar-medium plate supplemented with 50 μg/ml of kanamycin (Km) to obtain kanamycin-resistance (Km$^r$) transformants. Plasmids were extracted from the transformants, and the objective plasmid was selected and named pPK-T7lac-vd-antiOlac (FIG. 13).

(1-2) Construction of Plasmid pVC54-T7Pol for Expression of T7 RNA Polymerase

A plasmid, pVC54-T7Pol, for expression of T7 RNA polymerase was constructed in the following manner.

(1-2-1) Construction of pVC54

For the construction of pVC54, the region of SEQ ID NO: 58 containing the promoter region for chloramphenicol-resistance (Cm$^r$) gene and a portion derived from pAM330 of pVC7 (U.S. Pat. No. 5,804,414) was displaced by a region containing a strong promoter in the following manner.

Figure 14:
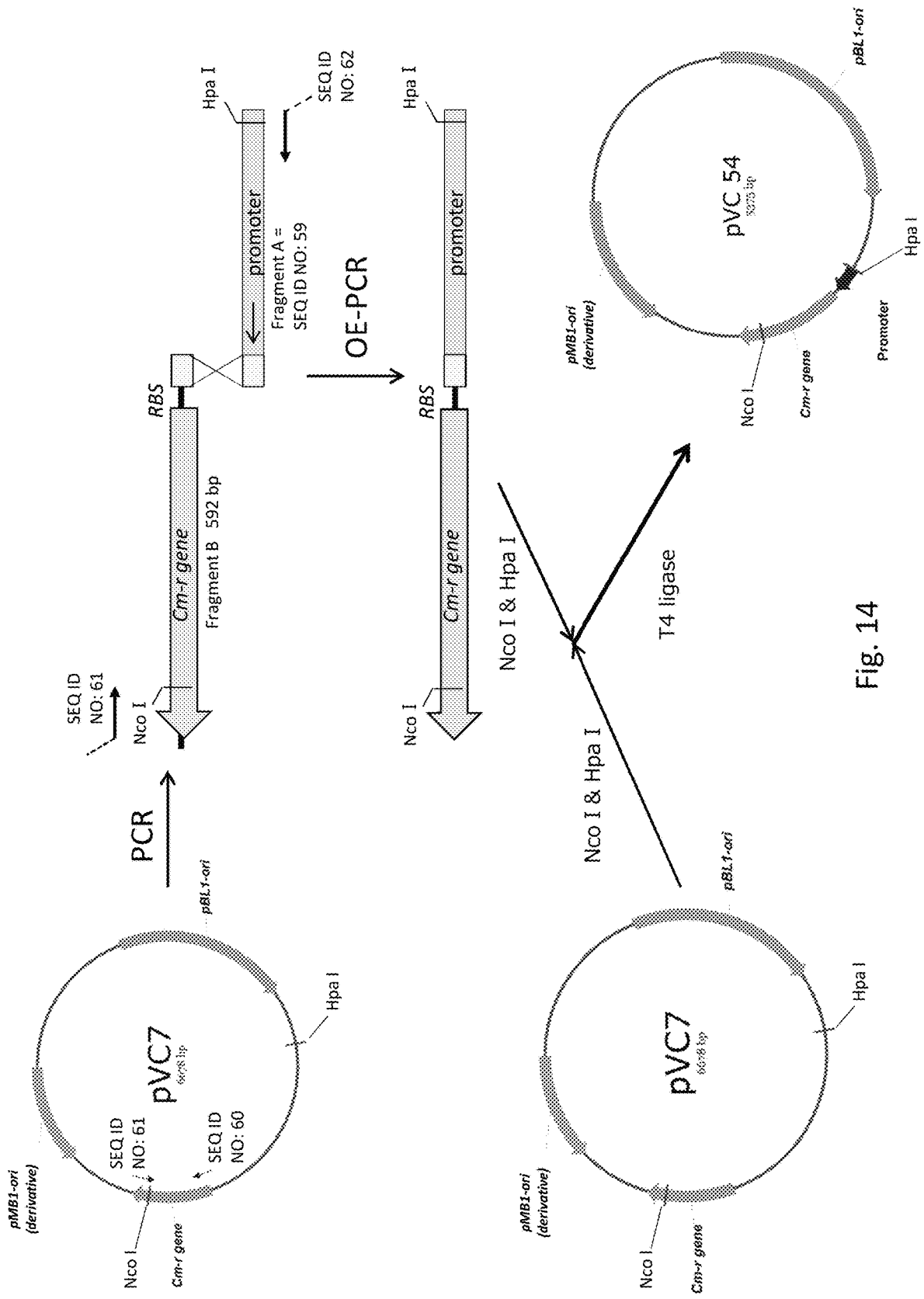
FIG. 14 shows a diagram of the construction scheme of plasmid pVC54.

A DNA fragment-A of SEQ ID NO: 58 (161 bp) containing the strong promoter was prepared by chemical synthesis. Separately, a DNA fragment-B was amplified by PCR using primers of SEQ ID NOS: 60 (L54-Cm) and 61 (R55-Cm) with pVC7 plasmid as the template. Overlapping-PCR was carried out by using the fragment-A and fragment-B, and the resulting PCR fragment was amplified again by PCR using flanking primers of SEQ ID NOS: 62 (L54-hpa) and 61 (R55-Cm). Then, the amplified fragment was digested with HpaI and NcoI, and ligated into HpaI-NcoI sites on pVC7. The ligation mixture was transformed into competent cells of the *E. coli* TG1 strain (Zymo Research) to obtain Cm$^r$ transformants. Plasmids were extracted from the transformants, and the objective plasmid was selected and named pVC54 (FIG. 14).

(1-2-2) Construction of pBS5t-ptrB*-T7pol

Figure 15:
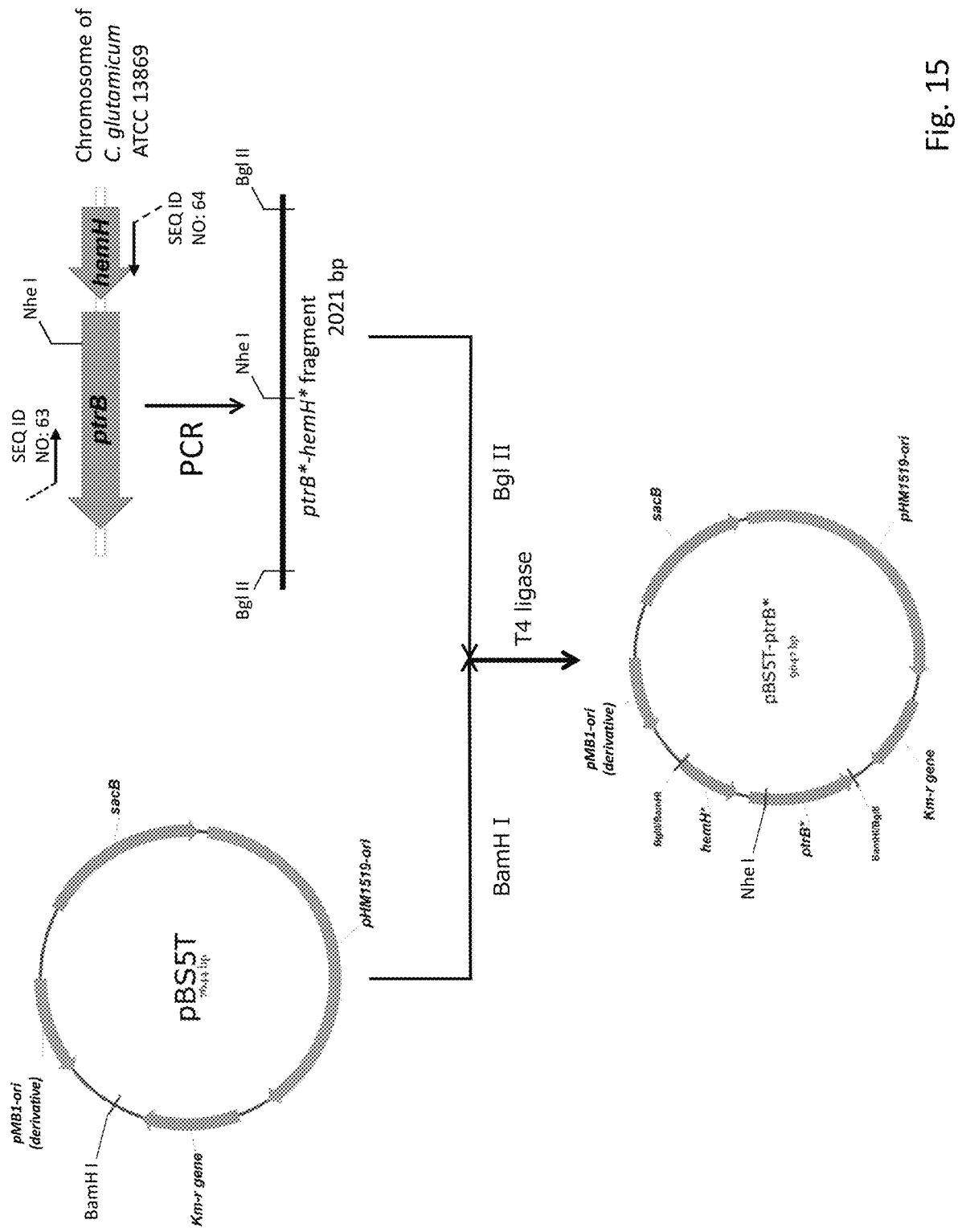
FIG. 15 shows a diagram of the construction scheme of plasmid pBS5t-ptrB*.

A DNA fragment (2021 bp) containing a part of ptrB and hemH genes was amplified by PCR using primers of SEQ ID NOS: 63 (×550) and 64 (×551) with genomic DNA of the 2256 strain as the template. The amplified fragment was digested with BglII, and cloned into BamHI site of pBS5t (WO2006/057450). The resulting plasmid was named pBS5t-ptrB* (FIG. 15). It contains unique NheI site in the part of ptrB gene.

Figure 16:
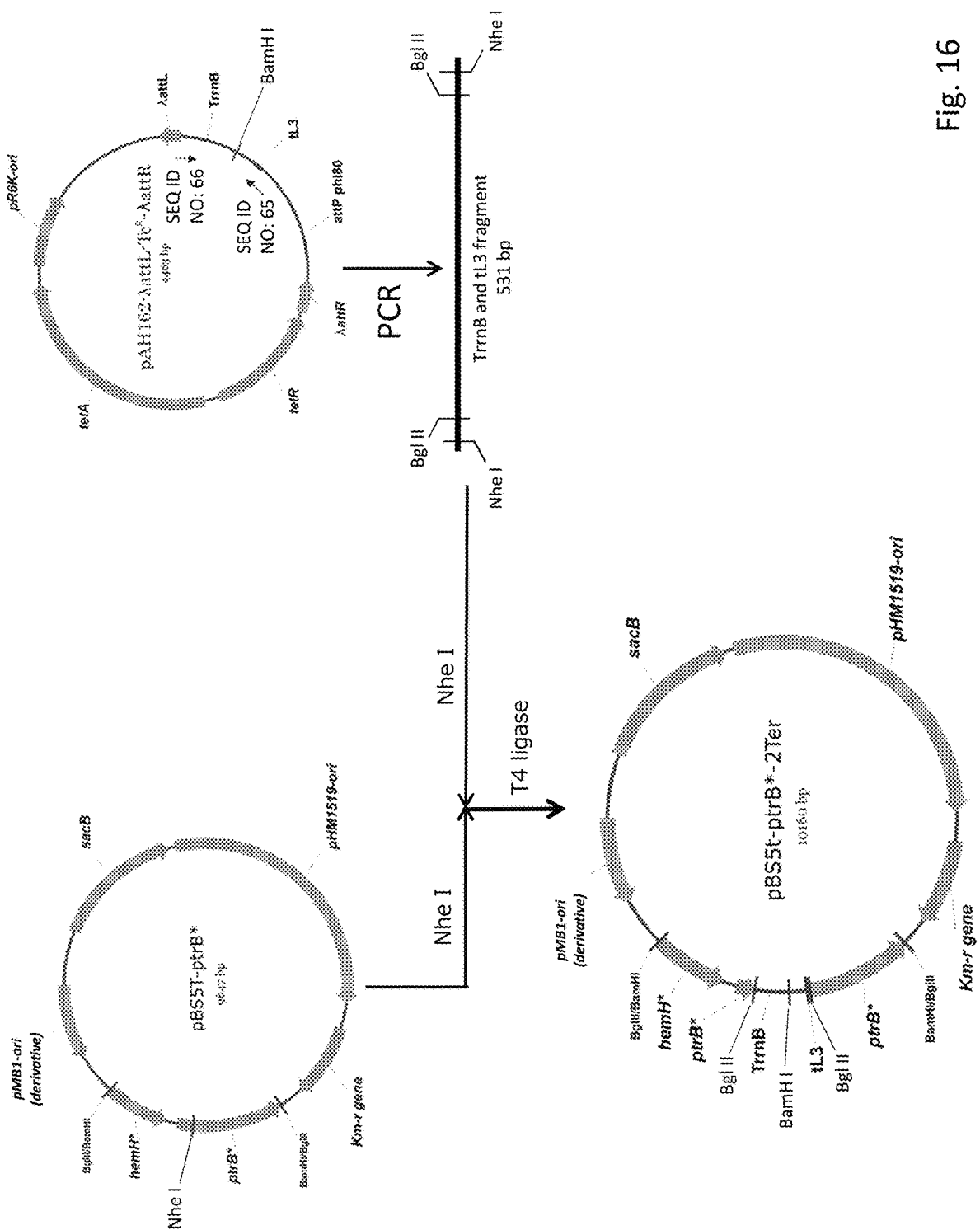
FIG. 16 shows a diagram of the construction scheme of plasmid pBS5t-ptrB*-2Ter.

Separately, another DNA fragment (531 bp) containing rrnB terminator (TrrnB) and L3 terminator (tL3) was amplified by PCR using primers of SEQ ID NOS: 65 (×553) and 66 (×554) with pAH162-λattL-Tc$^R$-λattR (*BMC Biotechnology* 2008, 8:63) as the template. The amplified fragment was digested with NheI, and cloned into NheI site of pBS5t-ptrB*. The resulting plasmid was named pBS5t-ptrB*-2Ter (FIG. 16). It contains unique BamHI site between the terminators TrrnB and tL3, and both the terminators are flanked by BglII sites.

Figure 17:
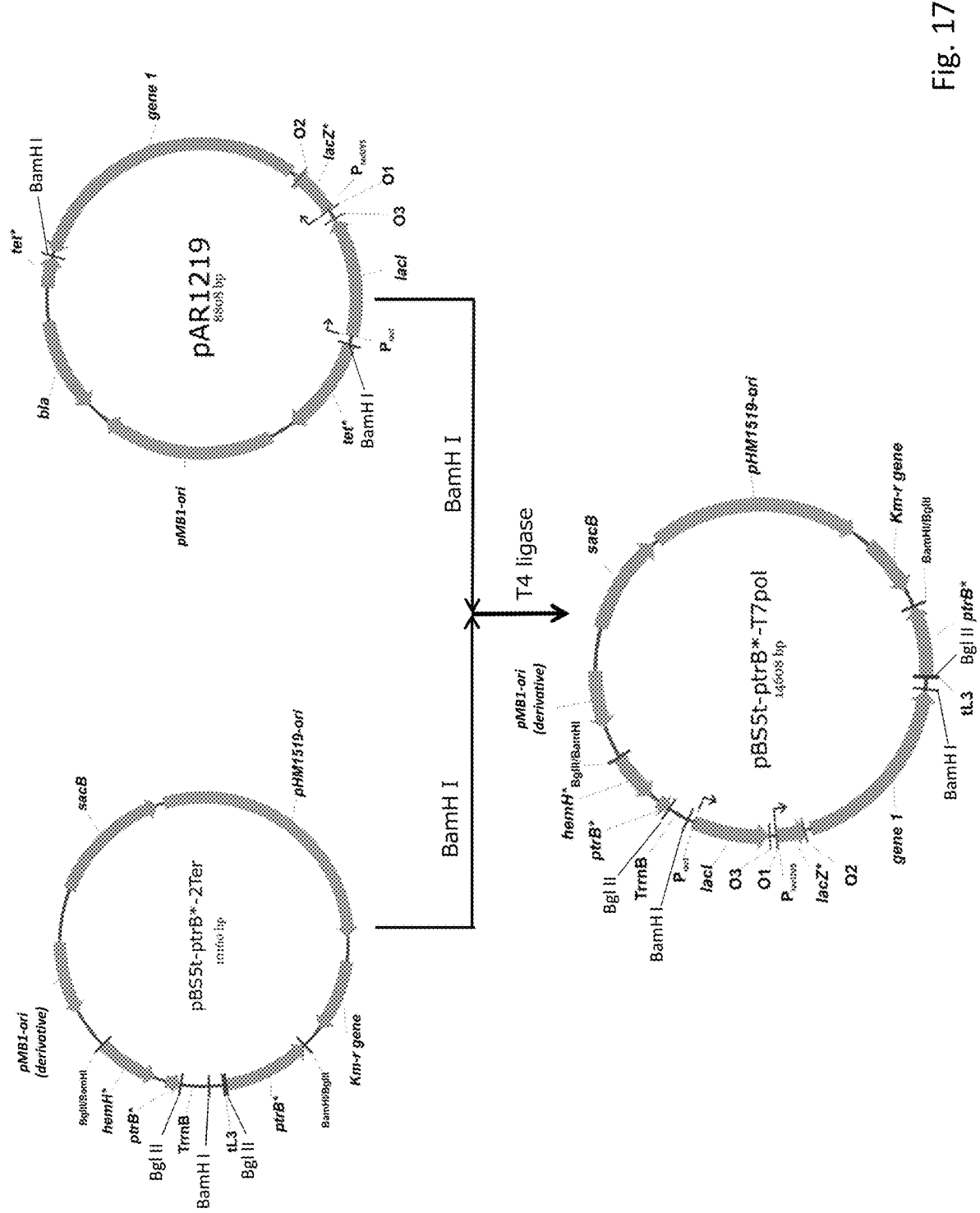
FIG. 17 shows a diagram of the construction scheme of plasmid pBS5t-ptrB*-T7pol.

Finally, a DNA fragment (4452 bp) containing lacI-PlacUV5-gene1 was cut out from pAR1219 (Proc Natl Acad Sci USA. 1984 April; 81(7): 2035-2039) with BamHI, and cloned into the unique BamHI site of pBS5t-ptrB*-2Ter. The lacI-PlacUV5-gene1 fragment contains gene1 encoding T7 RNA polymerase and expressed under control of lacUV5 promoter (PlacUV5). A plasmid with genetic orientation of gene1 to tL3 was selected and named pBS5t-ptrB*-T7pol (FIG. 17).

(1-2-3) Construction of pVC54-T7pol

The Plasmid pVC54-T7pol for expression of T7RNA polymerase was constructed from pVC54 and pBS5t-ptrB*-T7pol in the following manner.

Figure 18:
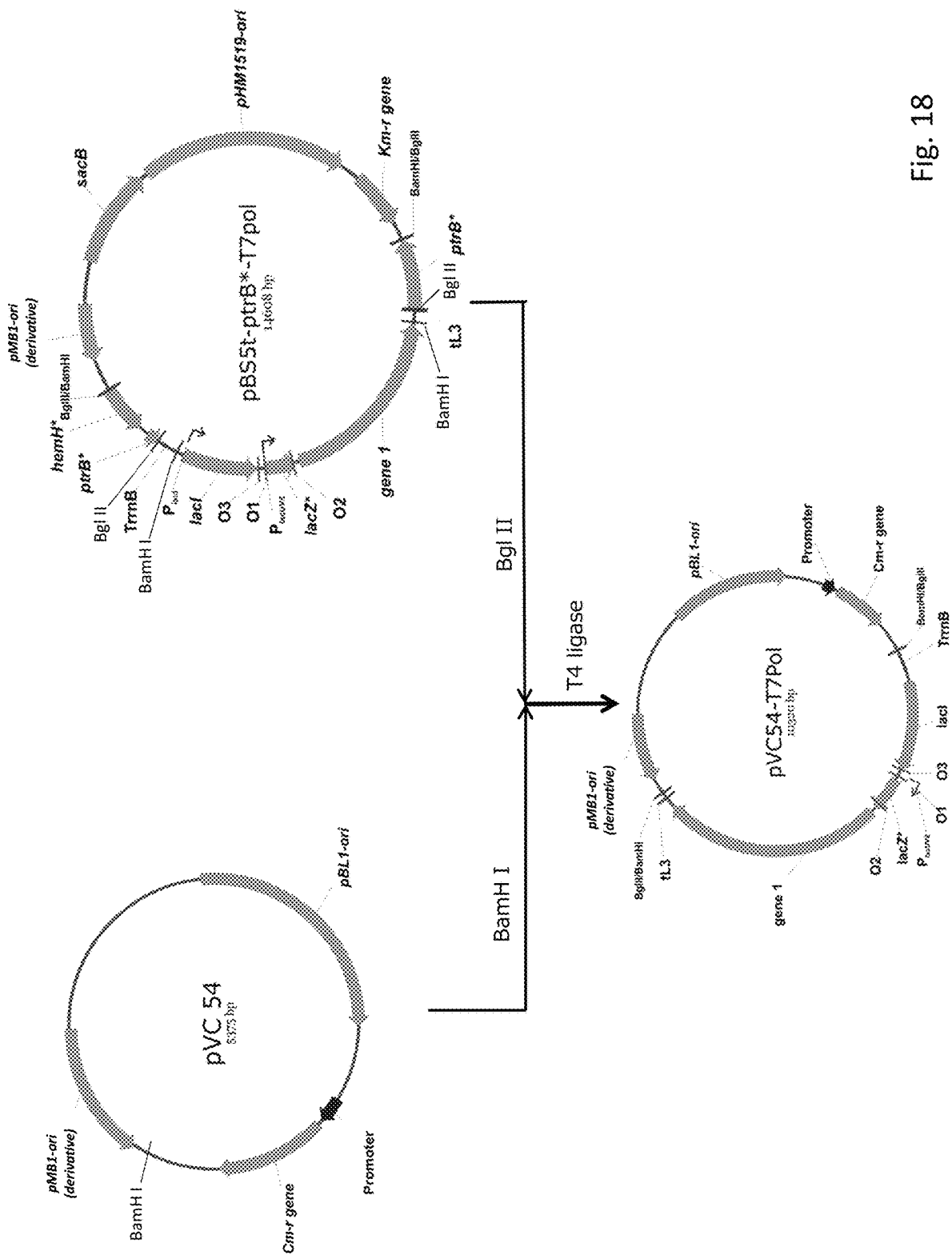
FIG. 18 shows a diagram of the construction scheme of plasmid pVC54-T7pol.

At first, a DNA fragment containing lacI-PlacUV5-gene1 was cut out from pBS5t-ptrB*-T7pol with BglII. Then, the DNA fragment was ligated into pVC54 at BamHI site to construct pVC54-T7pol (FIG. 18).

(1-3) Construction of RNA-Producing *C. glutamicum*

The *C. glutamicum* 2256ΔrncΔpAM330 strain was initially transformed with pVC54-T7Pol by electro-transformation method. Transformants were selected on a plate with CM2G medium (5 g/L of glucose, 10 g/L of tryptone, 10 g/L of yeast extract, 5 g/L of NaCl, adjusted to pH 7.0) supplemented with 10 μg/mL of chloramphenicol (Cm) in 24 hr growth at 30° C. Then, a single colony isolation method was applied for obtaining colonies of two independent clones of *C. glutamicum* 2256ΔrncΔpAM330 having pVC54-T7Pol. Those two clones were subject to another transformation with pPK-T7lac-vd-antiOlac. Transformants were selected on a plate with CM2G medium supplemented with 10 μg/mL of Cm and 25 μg/ml of Km in 24 hr growth at 30° C. Again, single colony isolation method was applied for obtaining colonies of two independent clones (named clones A and B) of *C. glutamicum* 2256ΔrncΔpAM330 having pVC54-T7Pol and pPK-T7lac-vd-antiOlac (named *C. glutamicum* 2256ΔrncΔpAM330/pVC54-T7Pol/pPK-T7lac-vd-antiOlac).

(1-4) RNA Production by T7-Promoter-Induced-Expression System in *C. glutamicum*

The *C. glutamicum* 2256ΔrncΔpAM330/pVC54-T7Pol/pPK-T7lac-vd-antiOlac strain (each of clones A and B) was inoculated into 5 ml of CM2G medium supplemented with 10 μg/mL of Cm and 25 μg/ml of Km, and cultured overnight at 32° C. On the next morning, the strain was inoculated into the same fresh medium (5 ml) at the OD$_{600}$ value of 0.2-0.3, and cultured at 32° C. for 4-5 hr. At this time, the induction was made by addition of 2 mM IPTG into the culture broth. After induction, the cultivation was continued for additional 3 hr and 19 hr, and also the OD$_{600}$ values of the culture broths were measured. Then, an aliquot (1-2 ml) of each of the culture broths was immediately mixed with RNAprotect Bacteria Reagent (QIAGEN 76506) according to manufacture recommendation, and pellet of cells was immediately frozen at −70° C.

Figure 19:
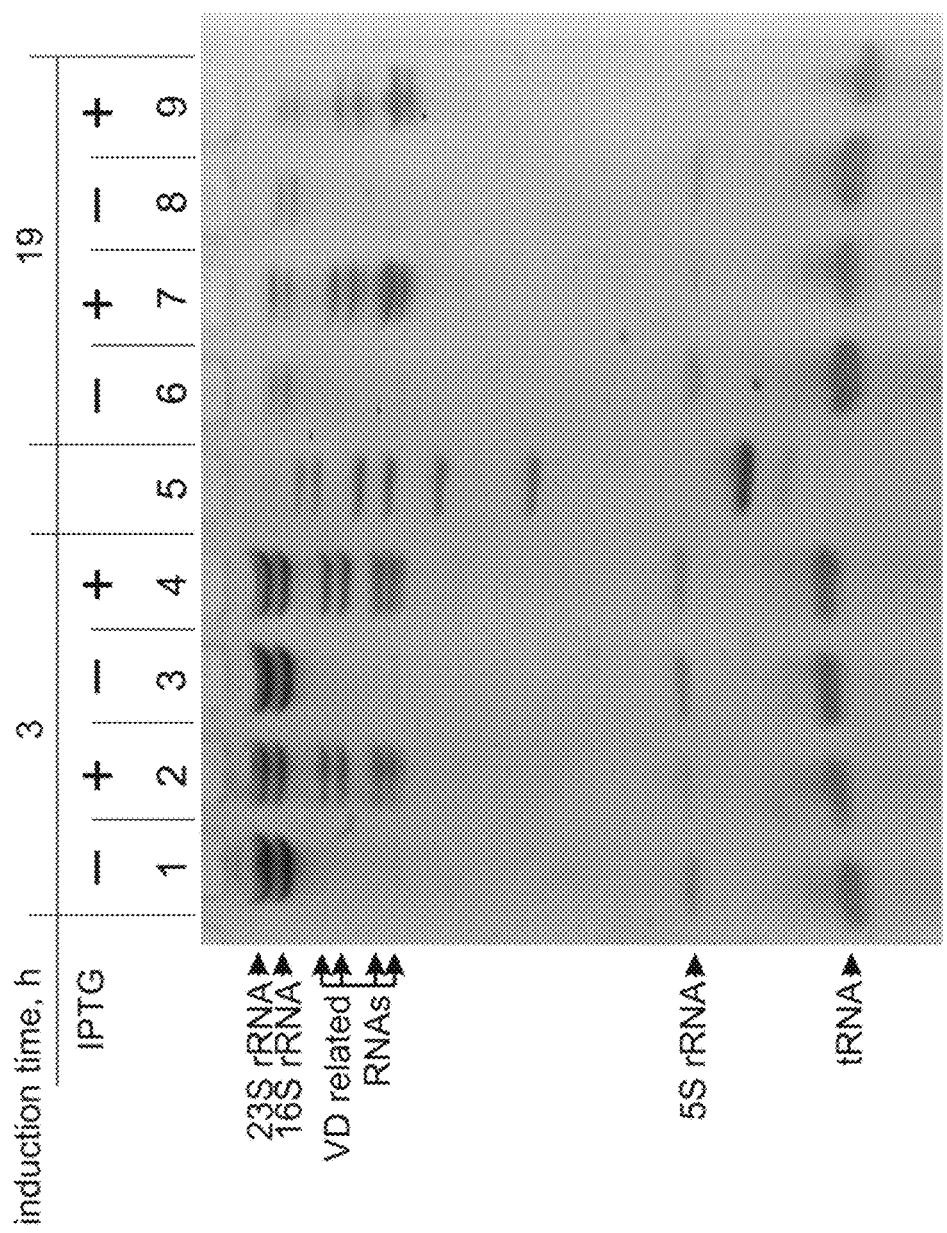
FIG. 19 shows an agarose gel electrophoretogram (photograph) showing RNA production by using T7-promoter-induced-expression system in *C. glutamicum*. Lanes 1-2 and 6-7, clone A; Lanes 3-4 and 8-9, clone B; and Lane 5, Century-Plus RNA Marker (Ambion AM7145).

All the samples were each melted at 4° C., and RNA isolation procedure using Trizol LS (Ambion 10296028) was applied. The isolated total RNA was diluted in 30 μl of DEPC-treated water to prepare a total RNA solution, the concentration of RNA in the solution was measured by Nanodrop spectrophotometer, and then an aliquot of the solution was applied for denaturing urea-PAGE (5%). Typically 3 μg each of total RNA solutions was applied to a well of the gel. After the electrophoresis, staining of RNA in the gel was done with ethidium bromide (EthBr). As a result, objective RNA bands (VD related RNAs) were observed for IPTG-induced samples (FIG. 19). That is, RNA production by using T7-promoter-induced-expression system in *C. glutamicum* was confirmed.

(2) Production of Hv-iap RNA (2-1) Construction of Plasmid pPK4-T7pol for Expression of T7 RNA Polymerase A plasmid, pPK4-T7pol, for expression of T7 RNA polymerase was constructed in the following manner.

Figure 20:
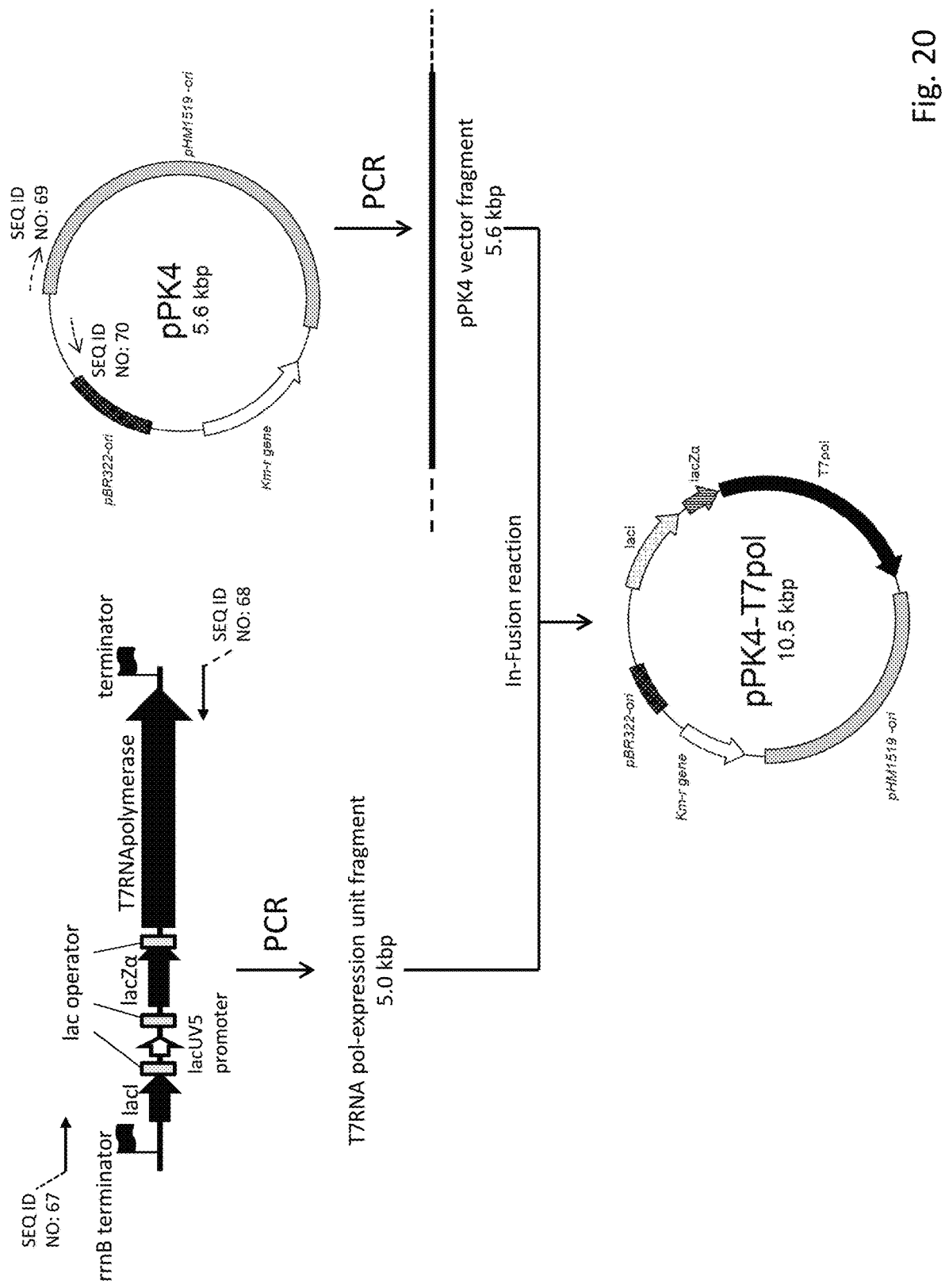
FIG. 20 shows a diagram of the construction scheme of plasmid pPK4-T7pol.

A DNA fragment containing gene 1 (T7pol) encoding T7 RNA polymerase was amplified by PCR using KOD FX NEO polymerase, primers of SEQ ID NOS: 67 and 68, and pVC54-T7pol as the template. Another DNA fragment was obtained by PCR using primers of SEQ ID NOS: 69 and 70, and a plasmid pPK4 (U.S. Pat. No. 6,090,597) as the template. Both the DNA fragments were mixed, and ligated to each other by using In-Fusion HD Cloning Kit (TAKARA BIO). Then, E. coli JM109 competent cells were transformed with the reaction mixture, applied to LB agar medium containing Km (50 µg/mL), and cultured at 37° C. for 16 hr to obtain Km$^R$ transformants. Among them, several colonies were isolated, and plasmids were extracted from the transformants. After the confirmation of the DNA sequences of the plasmids, an objective plasmid was selected and named pPK4-T7pol (FIG. 20).

(2-2) Construction of Plasmid pVC7-Pt7-Hv-iap-Pt7rev for Transcription of Hv-iap RNA A plasmid, pVC7-Pt7-Hv-iap-Pt7rev, for transcription of Hv-iap RNA as objective RNA under control of T7 promoter in dual directions was constructed in the following manner.

(2-2-1) Construction of pVC7-Pt7-KpnI-XhoI-Pt7rev

Figure 21:
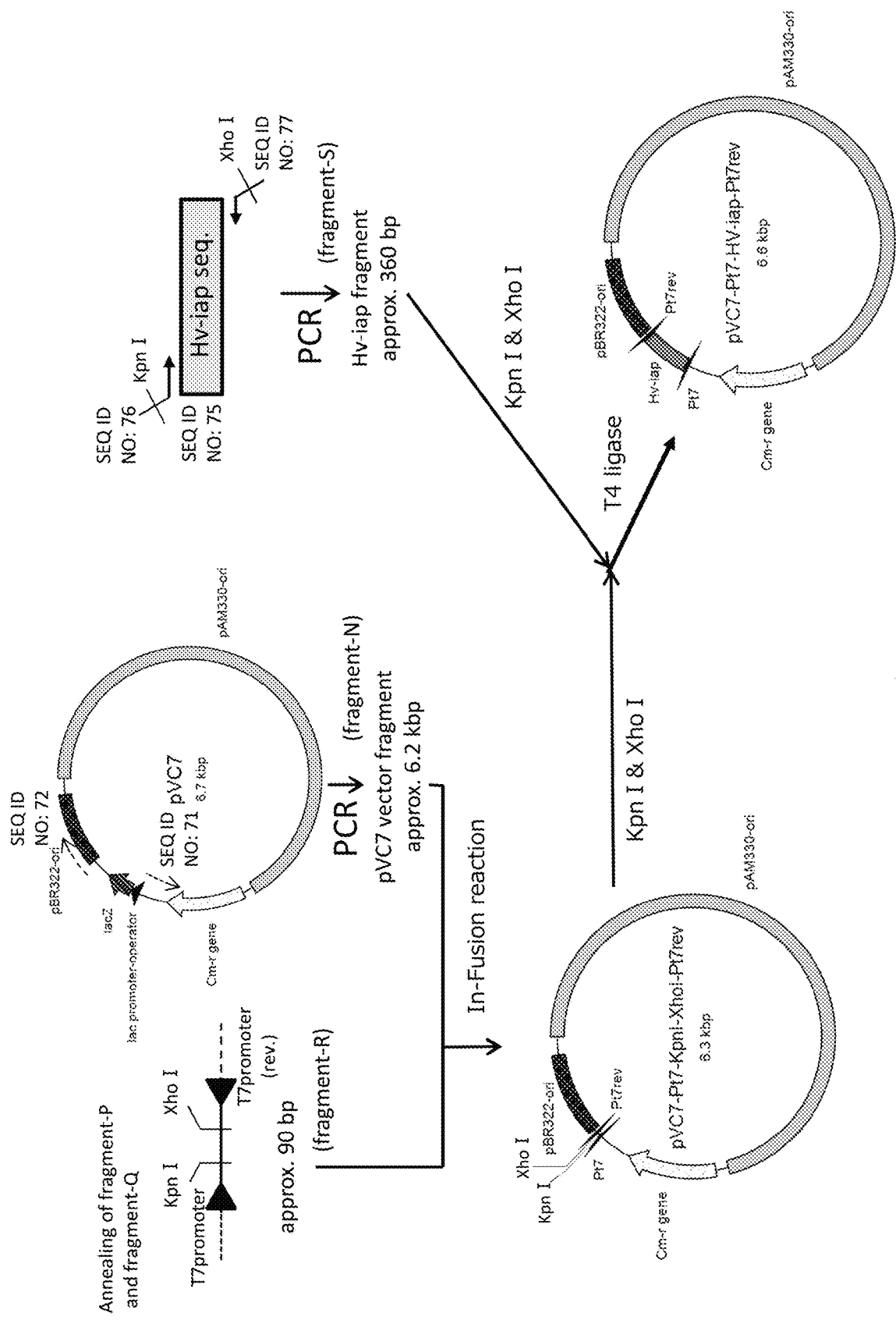
FIG. 21 shows a diagram of the construction scheme of plasmid pVC7-Pt7-Hv-iap-Pt7rev.

A DNA fragment-N was obtained by PCR using KOD FX NEO, primers of SEQ ID NOS: 71 and 72, and pVC7 as the template. Separately, a DNA fragment-P of SEQ ID NO: 73 containing T7 promoter (forward-direction), KpnI restriction site, XhoI restriction site, and T7-promoter (reversed-direction) in this order, and another DNA fragment-Q of SEQ ID NO: 74 containing the complimentary sequence of the fragment-P were prepared by chemical synthesis, and both the single-stranded DNA fragments were mixed and annealed to produce a DNA fragment-R. Then, both the DNA fragment-N and DNA fragment-R were ligated to each other by using In-Fusion HD Cloning Kit. E. coli JM109 competent cells were transformed with the reaction mixture, applied to LB agar medium containing Cm (25 µg/ml), and cultured at 37° C. for 16 hr to obtain Cm$^R$ transformants. Among them, several colonies were isolated, and plasmids were extracted from the transformants. After the confirmation of the DNA sequences of the plasmids, an objective plasmid was selected and named pVC7-Pt7-KpnI-XhoI-Pt7rev (FIG. 21).

(2-2-2) Construction of pVC7-Pt7-Hv-iap-Pt7rev

A DNA fragment-S containing KpnI restriction site, Hv-iap, and XhoI restriction site in this order was amplified by PCR using a DNA fragment of SEQ ID NO: 75 as the template, and primers of SEQ ID NOS: 76 and 77. Then, the DNA fragment-S and pVC7-Pt7-KpnI-XhoI-Pt7rev were each digested with KpnI and XhoI, and purified with MinElute PCR Purification Kit (Qiagen). Both the purified products were mixed, and ligated to each other by using Ligation high ver. 2 (TOYOBO). E. coli JM109 competent cells were transformed with the reaction mixture, applied to LB agar medium containing Cm (25 µg/ml), and cultured at 37° C. for 16 hr to obtain Cm$^R$ transformants. Among them, several colonies were isolated, and plasmids were purified from the transformants. After the confirmation of the DNA sequences of the plasmids, an objective plasmid was selected and named pVC7-Pt7-Hv-iap-Pt7rev (FIG. 21).

(2-3) Construction of RNA-Producing C. glutamicum

The C. glutamicum 2256ΔrncΔpAM330 strain was introduced with pPK4-T7pol by electroporation. The cell suspension was applied to CM-Dex agar medium containing Km (25 µg/ml), and cultured at 30° C. for 16 hr to obtain transformants. Subsequently, one of the transformants was introduced with pVC7-Pt7-Hv-iap-Pt7rev. The cell suspension was applied to CM-Dex agar medium containing Km (25 µg/ml) and Cm (5 µg/ml), and cultured at 30° C. for 24 hr to obtain transformants. Thus, finally C. glutamicum 2256ΔrncΔpAM330/pPK4-T7pol/pVC7-Pt7-Hv-iap-Pt7rev was obtained.

(2-4) RNA Production by T7-Promoter-Induced-Expression System in C. glutamicum

The C. glutamicum 2256ΔrncΔpAM330/pPK4-T7pol/pVC7-Pt7-Hv-iap-Pt7rev strain was grown at 30° C. in a test tube containing CM-Dex medium containing Km (25 µg/ml) and Cm (5 µg/ml) for 16 hr to prepare a seed culture broth. Then, the seed culture broth was inoculated into a fresh CM-Dex medium with a one-tenth of the volume of the medium to start main culture at 30° C. After 6 hr incubation, an aliquot of the culture broth was sampled, and the rest of the culture broth was added with 2 mM IPTG and further cultured. At 3 hr and 27 hr after IPTG addition, aliquots of the culture broth were sampled. RNA was extracted from 200 µL of the culture broth in the same manner including RNAprotect Bacteria Reagent treatment as the above-mentioned Example, and finally the RNA sample was dissolved with 50 µL of RNase-free water to prepare a total RNA solution.

Figure 22:
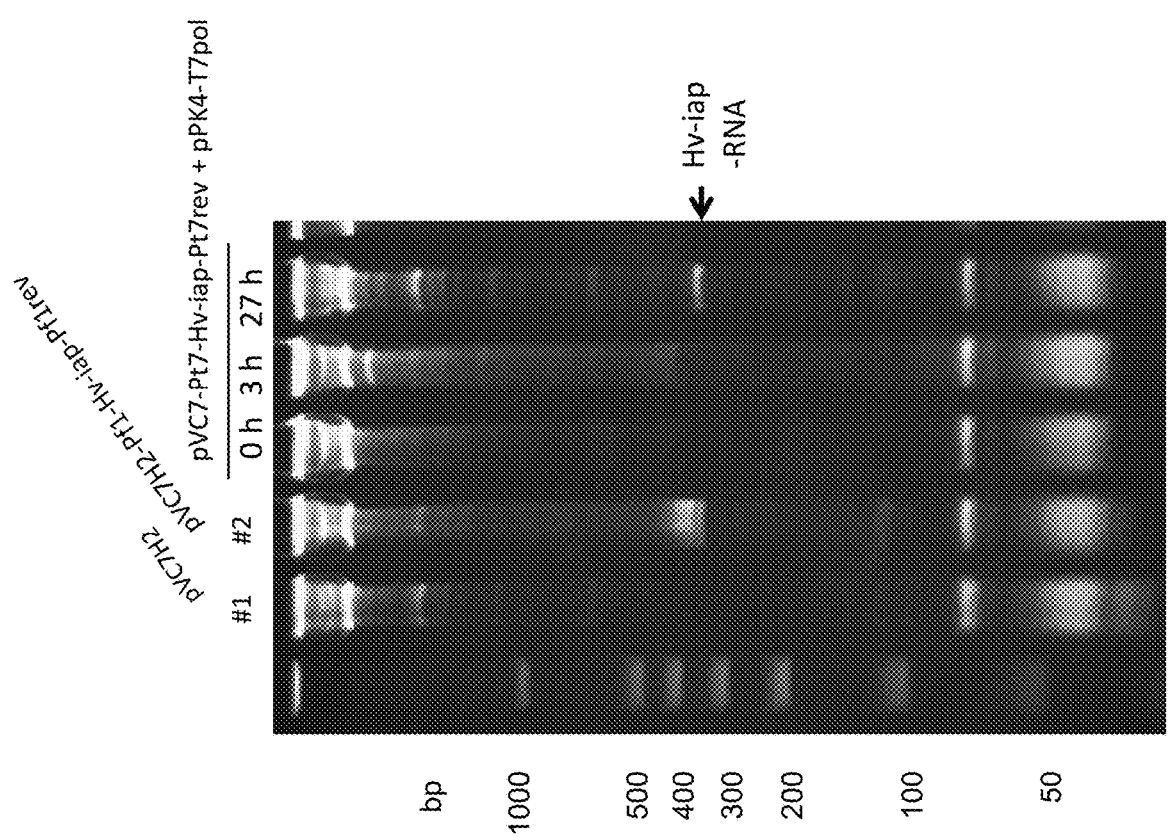
FIG. 22 shows an agarose gel electrophoretogram (photograph) showing RNA production by using T7-promoter-induced-expression system in *C. glutamicum*.

The total RNA solutions were each applied to Novex TBE gels (6%), and RNA production was analyzed. As a result, an objective RNA band (Hv-iap RNA) was observed for the sample obtained at 27 hr after IPTG induction (FIG. 22). That is, RNA production by using T7-promoter-induced-expression system in C. glutamicum was again confirmed.

<10> Acquisition of High Copy Number Variation Plasmids of pPK4

The plasmid pPK4 is a composite plasmid of a plasmid pHSG399 usable for E. coli and a plasmid pHM1519 possessed by C. glutamicum ATCC 13058, and hence, pPK4 serves as a shuttle vector replicable in both bacteria (U.S. Pat. No. 6,090,597).

The mutations shown in Table 3 were each introduced into pPK4, and effect of these mutations on the copy number of the plasmid was evaluated.

The mutant plasmids were each constructed with KOD-Plus-Mutagenesis Kit (TOYOBO). There were constructed pPK4H1 by using primers of SEQ ID NOS: 79 and 80, pPK4H2 by using primers of SEQ ID NOS: 81 and 82, pPK4H3 by using primers of SEQ ID NOS: 83 and 82, pPK4H4 by using primers of SEQ ID NOS: 84 and 82, pPK4H5 by using primers of SEQ ID NOS: 85 and 82, and pPK4H6 by using primers of SEQ ID NOS: 86 and 82, in combination with the plasmid pPK4 as the template, according to the construction protocol attached to the kit (Table 3). The total nucleotide sequences thereof were confirmed to be correct with a DNA sequencer.

TABLE 3 pPK4 mutant plasmids

| No. | Plasmid name | Type of mutation | Nucleotide sequence 5'-AAAGGAAAT-3' (wild-type) |
|---|---|---|---|
| 1 | pPK4H1 | Single-nucleotide substitution | 5'-AAAG<u>A</u>AAAT-3' |
| 2 | pPK4H2 | Single-nucleotide substitution | 5'-AAAG<u>C</u>AAAT-3' |

TABLE 3-continued pPK4 mutant plasmids

| No. | Plasmid name | Type of mutation | Nucleotide sequence 5'-AAAGGAAAT-3' (wild-type) |
|---|---|---|---|
| 3 | pPK4H3 | Two-nucleotide substitution | 5'-AAA<u>AA</u>AAT-3' |
| 4 | pPK4H4 | Two-nucleotide substitution | 5'-AAAG<u>AC</u>AAT-3' |
| 5 | pPK4H5 | Two-nucleotide substitution | 5'-AAA<u>CC</u>AAAT-3' |
| 6 | pPK4H6 | Two-nucleotide substitution | 5'-AAA<u>C</u>A<u>A</u>AAT-3' |

In the nucleotide sequences, nucleotide(s) different from that/those of the wild-type was/were underlined.

The copy numbers of the constructed plasmids were analyzed in the same manner as Example <5>. As a result, it was revealed that all the pPK4 mutant plasmids shown in Table 3 showed a higher copy number in *C. glutamicum* than the original plasmid pPK4. Among them, pPK4H1 showed the highest copy number, which reached about 200 copies or higher per chromosome of the host.

<11> RNA Production Using pPK4H1

The expression system of U1A-RNA was integrated into the plasmid pPK4H1 in the following manner.

PCR amplification was performed by using pVC7-Pf1-U1Ainsert as the template, primers of SEQ ID NOS: 87 and 88, and KOD FX NEO (TOYOBO) to obtain an amplified fragment of the U1Ainsert RNA transcription unit. Separately, PCR amplification was performed by using pPK4H1 as the template, primers of SEQ ID NOS: 89 and 90, and KOD FX NEO (TOYOBO) to obtain an amplified fragment of pPK4H1. These amplified fragments were mixed, and mutually ligated by using In-Fusion HD Cloning Kit (Clontech). Then, competent cells of the *Escherichia coli* JM109 strain (TAKARA BIO) were transformed with the reaction mixture, applied to LB agar medium containing 50 µg/mL of kanamycin, and cultured at 37° C. overnight. Then, single colonies were isolated from colonies that appeared to obtain transformants. Plasmids were extracted from the obtained transformants in the usual manner. An objective plasmid was identified by DNA sequencing analysis, and designated as pPK4H1-Pf1-U1Ainsert.

The *C. glutamicum* strain 2256ΔrncΔpAM330 was introduced with each of the plasmids pPK4H1 and pPK4H1-Pf1-U1Ainsert by the electric pulse method, applied to CM-Dex agar medium containing 25 µg/mL of kanamycin, and cultured at 30° C. overnight. Thereby, transformant strains 2256ΔrncΔpAM330/pPK4H1 and 2256ΔrncΔpAM330/pPK4H1-Pf1-U1Ainsert were obtained.

Two colonies each for the transformant strains were selected, spread on CM-Dex agar medium containing 25 µg/mL of kanamycin, and cultured at 30° C. for about 16 hr. Then, a part of the cultured cells was used for test-tube culture. Culture was carried out in 2 mL of CM-Dex medium containing 25 µg/mL of kanamycin at 30° C. with shaking for 24 hr. Then, 200 µL of the culture broth was treated with RNAprotect Bacteria Reagent, and the supernatant was removed. Then, 225 µL of TE buffer containing 15 mg/mL of lysozyme (SIGMA) was added thereto to perform a reaction at the room temperature for 30 min, 25 µL of 20 mg/mL proK (TAKARA BIO) was further added thereto to perform a reaction at the room temperature for 30 min, and then, RNA was extracted with TRIzol LS (Thermo Fisher Scientific). The extracted RNA was dissolved with 50 µL of RNase-free water to prepare a total RNA solution. The obtained total RNA solutions were subject to total RNA analysis using Novex TBE Gels, 6% (Thermo Fisher Scientific). That is, 1 µL each of the total RNA solutions was applied to a lane of the gel, and poly-acrylamide gel electrophoresis (PAGE) was performed under non-denaturing conditions.

Figure 23:
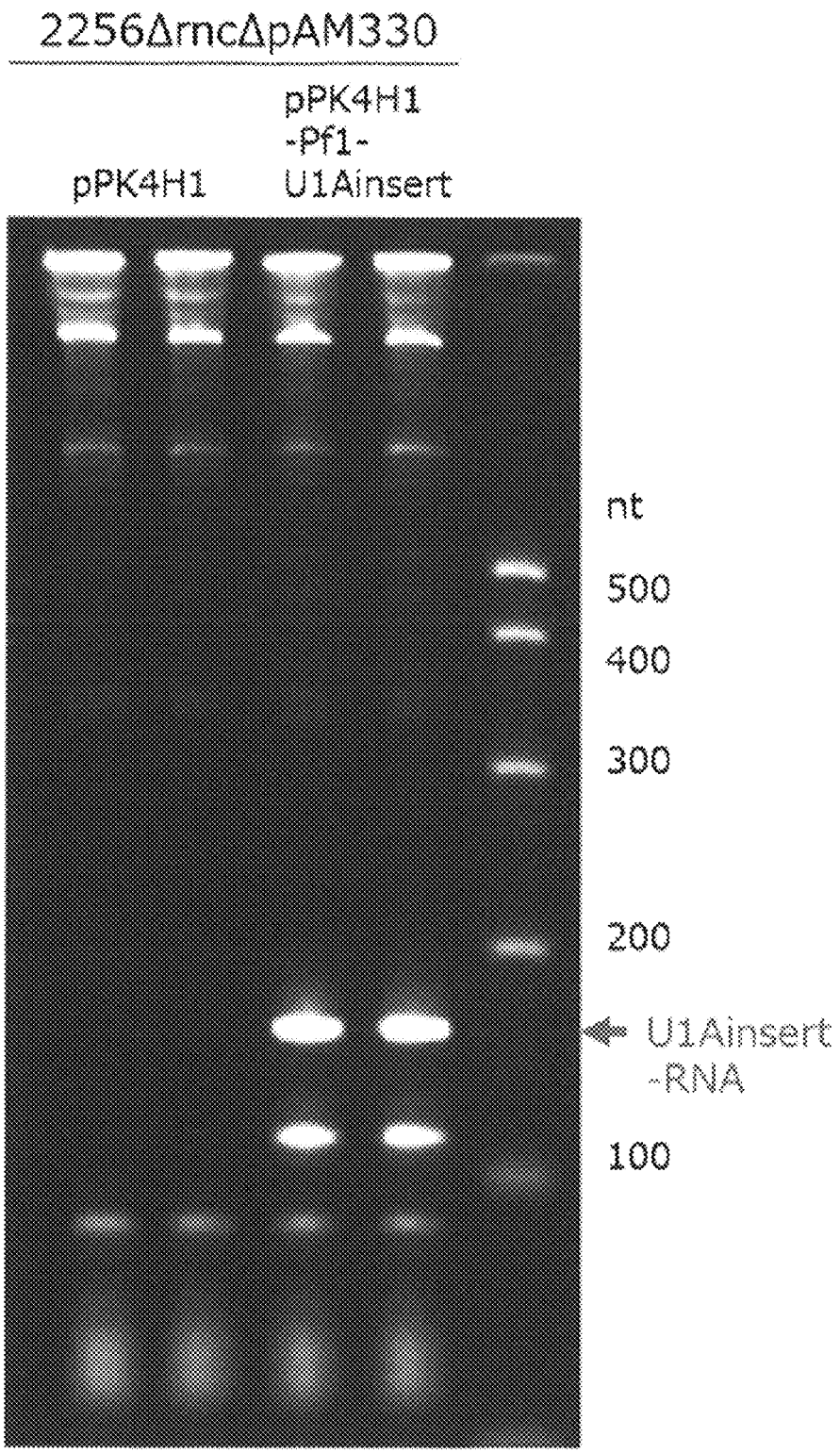
FIG. 23 shows an agarose gel electrophoretogram (photograph) showing RNA production by using high copy number plasmid pPK4H1.

As a result, an RNA band derived from U1Ainsert was confirmed at a predicted position only for the strain 2256ΔrncΔpAM330/pPK4H1-Pf1-U1Ainsert (FIG. 23). Thus, a large amount of objective RNA was successfully produced in a *Corynebacterium* bacterium as a host even when using a pHM1519-derived vector, which is different from pVC7-derived vectors used in former Examples.

INDUSTRIAL APPLICABILITY

According to the present invention, RNA can be efficiently produced.

EXPLANATION OF SEQUENCE LISTING

SEQ ID NOS:
1-12: Primers
13: Nucleotide sequence of F1 promoter
14: Nucleotide sequence of terminator region of BFK20
15: Nucleotide sequence of U1A-binding sequence
16: Nucleotide sequence of transcription unit for U1Ainsert RNA
17-20: Primers
21: Nucleotide sequence of Hv-iap
22-50: Primers
51: Nucleotide sequence of rnc gene of *C. glutamicum* 2256 (ATCC 13869)
52: Amino acid sequence of Rnc protein of *C. glutamicum* 2256 (ATCC 13869)
53: Nucleotide sequence of DNA fragment
54-57: Primers
58: Nucleotide sequence of DNA fragment
59: Nucleotide sequence of DNA fragment-A
60-72: Primers
73: Nucleotide sequence of DNA fragment-P
74: Nucleotide sequence of DNA fragment-Q
75: Nucleotide sequence of DNA fragment
76-77: Primers
78: Nucleotide sequence of T7 promoter
79-90: Primers

We claim:

1. A method for producing objective RNA, the method comprising:
   A) culturing a coryneform bacterium having an expression unit for the objective RNA in a medium, to express the objective RNA and accumulate the objective RNA in cells of the bacterium; and
   B) collecting the objective RNA from the cells,
   wherein the bacterium has been modified so that the activity of ribonuclease III is reduced as compared with a non-modified strain by attenuating the expression of a gene encoding ribonuclease III;
   wherein the ribonuclease III is a protein selected from the group consisting of:
   (a) a protein comprising the amino acid sequence of SEQ ID NO: 52;
   (b) a protein comprising the amino acid sequence of SEQ ID NO: 52, but which includes substitution, deletion, insertion, and/or addition of 1 to 10 amino acid residues, and having ribonuclease III activity; and
   (c) a protein comprising an amino acid sequence having an identity of 90% or higher to the amino acid sequence of SEQ ID NO: 52, and having ribonuclease III activity.

2. The method according to claim 1, wherein the bacterium comprises 5 copies/cell or more of the expression unit.

3. The method according to claim 1, wherein the bacterium comprises 70 copies/cell or more of the expression unit.

4. The method according to claim 1, wherein the bacterium comprises a vector containing the expression unit.

5. The method according to claim 1, wherein the expression unit comprises a promoter sequence that functions in the coryneform bacterium and a nucleotide sequence encoding the objective RNA in the direction from 5' to 3'.

6. The method according to claim 5, wherein the promoter sequence is a promoter derived from a phage.

7. The method according to claim 5, wherein the promoter sequence is F1 promoter or T7 promoter.

8. The method according to claim 5, wherein the promoter sequence is a promoter selected from the group consisting of:
   (a) a promoter comprising the nucleotide sequence of SEQ ID NO: 13 or 78; and
   (b) a promoter comprising a nucleotide sequence having an identity of 90% or higher to the nucleotide sequence of SEQ ID NO: 13 or 78.

9. The method according to claim 1, wherein the bacterium is a bacterium belonging to the genus *Corynebacterium*.

10. The method according to claim 1, wherein the bacterium is *Corynebacterium glutamicum*.

* * * * *

SEQUENCE LISTING

<160> NUMBER OF SEQ ID NOS: 90

<210> SEQ ID NO 1
<211> LENGTH: 35
<212> TYPE: DNA

```
<213> ORGANISM: Artificial Sequence
<220> FEATURE:
<223> OTHER INFORMATION: primer

<400> SEQUENCE: 1
aaaacgacgg ccagtggctg aatctgagcg cctgg                              35

<210> SEQ ID NO 2
<211> LENGTH: 35
<212> TYPE: DNA
<213> ORGANISM: Artificial Sequence
<220> FEATURE:
<223> OTHER INFORMATION: primer

<400> SEQUENCE: 2
tcaacttcag gcagtaggaa cttctccaaa ccagc                              35

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
actgcctgaa gttgaggtgg tg                                            22

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
gaccatgatt acgccaagaa aatcgacact gtcag                              35

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
ggcgtaatca tggtcatagc tgtttc                                        26

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
actggccgtc gttttacaac gtcg                                          24

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
ggctgaatct gagcgcctgg tc                                            22
```

```
<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
aagaaaatcg acactgtcag ccag                                          24

<210> SEQ ID NO 9
<211> LENGTH: 38
<212> TYPE: DNA
<213> ORGANISM: Artificial Sequence
<220> FEATURE:
<223> OTHER INFORMATION: primer

<400> SEQUENCE: 9
gacgttgatc ggcacgacga tcctttttaa cccatcac                           38

<210> SEQ ID NO 10
<211> LENGTH: 39
<212> TYPE: DNA
<213> ORGANISM: Artificial Sequence
<220> FEATURE:
<223> OTHER INFORMATION: primer

<400> SEQUENCE: 10
agacgtagac aagctcatat gggattcacc tttatgttg                          39

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
agcttgtcta cgtctgatgc tttg                                          24

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
gtgccgatca acgtctcatt ttc                                           23

<210> SEQ ID NO 13
<211> LENGTH: 139
<212> TYPE: DNA
<213> ORGANISM: Bacteriophage BFK20

<400> SEQUENCE: 13
gatctactcg ttactcaagg caaggtcgag cgggacggtc gaaccagctt caagcgaccg    60
gatgagtatg ttcagtagaa tagcgagcgg gagaccgctc gaccttagtt ctcctgttgc   120
gggggagttc atgggatcc                                                139

<210> SEQ ID NO 14
<211> LENGTH: 50
<212> TYPE: DNA
```

<213> ORGANISM: Bacteriophage BFK20

<400> SEQUENCE: 14
atagcataaa ataacgcccc accttcttaa cgggaggtgg ggcgttattt        50

<210> SEQ ID NO 15
<211> LENGTH: 18
<212> TYPE: DNA
<213> ORGANISM: Homo sapiens

<400> SEQUENCE: 15
gggcattgca ctccgccc                                           18

<210> SEQ ID NO 16
<211> LENGTH: 259
<212> TYPE: DNA
<213> ORGANISM: Artificial Sequence
<220> FEATURE:
<223> OTHER INFORMATION: U1Ainsert RNA transcription unit

<400> SEQUENCE: 16
gatctactcg ttactcaagg caaggtcgag cgggacggtc gaaccagctt caagcgaccg        60
gatgagtatg ttacagtaga tagcgagcgg gagaccgctc gaccttagtt ctcctgttgc       120
gggggagttc atgggatcca cgtaccctgc gagacaggag taatcctaaa cagggcattg       180
cactccgccc ttgctagcat agcataaaat aacgccccac cttcttaacg ggaggtgggg       240
cgttattttt acggggatc                                                   259

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
taggcacccc aggctgatct actcgttact caaggcaag                    39

<210> SEQ ID NO 18
<211> LENGTH: 35
<212> TYPE: DNA
<213> ORGANISM: Artificial Sequence
<220> FEATURE:
<223> OTHER INFORMATION: primer

<400> SEQUENCE: 18
ggaagcggaa gaagcgatcc ccgtaaaaat aacgc                        35

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gcttcttccg cttcctcgct c                                       21

<210> SEQ ID NO 20
<211> LENGTH: 20
<212> TYPE: DNA
<213> ORGANISM: Artificial Sequence
<220> FEATURE:
<223> OTHER INFORMATION: primer

```
<400> SEQUENCE: 20
agcctggggt gcctaatgag                                                    20

<210> SEQ ID NO 21
<211> LENGTH: 346
<212> TYPE: DNA
<213> ORGANISM: Henosepilachna vigintioctopunctata

<400> SEQUENCE: 21
cctcggaatc ggcgaccaga cgttgtgctt ctactgcggc ggcggtctga aagattgggt        60
cgaagaagac gatccgtggg aacagcacgc gctttggttc ccccagtgta attatctatt       120
attgaagaaa acacccgctt tcgtcaaaga cgtccaagaa aaacataaag gcgatttgtc       180
gtcatccaag caaaacgaga ccgaagtggt agcaagtagt agcagtagtc acaactccaa       240
agaatctcca agtgcggtgg tagaagagcg agaaagaaac aacgcagagg aaagctcgac       300
attatgcaaa atatgttata aaaatgaatt ggctgttgta tttcta                      346

<210> SEQ ID NO 22
<211> LENGTH: 36
<212> TYPE: DNA
<213> ORGANISM: Artificial Sequence
<220> FEATURE:
<223> OTHER INFORMATION: primer

<400> SEQUENCE: 22
gctgttgtat ttctaaaggc caggaaccgt aaaaag                                  36

<210> SEQ ID NO 23
<211> LENGTH: 36
<212> TYPE: DNA
<213> ORGANISM: Artificial Sequence
<220> FEATURE:
<223> OTHER INFORMATION: primer

<400> SEQUENCE: 23
taggcacccc aggctgatct actcgttact caaggc                                  36

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
tcgctatcta ctgtaacata ctc                                                23

<210> SEQ ID NO 25
<211> LENGTH: 34
<212> TYPE: DNA
<213> ORGANISM: Artificial Sequence
<220> FEATURE:
<223> OTHER INFORMATION: primer

<400> SEQUENCE: 25
tacagtagat agcgacctcg gaatcggcga ccag                                    34

<210> SEQ ID NO 26
<211> LENGTH: 21
<212> TYPE: DNA
<213> ORGANISM: Artificial Sequence
<220> FEATURE:
```

```
<223> OTHER INFORMATION: primer

<400> SEQUENCE: 26
tagaaataca acagccaatt c                                           21

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
aaggccagga accgtaaaaa g                                           21

<210> SEQ ID NO 28
<211> LENGTH: 36
<212> TYPE: DNA
<213> ORGANISM: Artificial Sequence
<220> FEATURE:
<223> OTHER INFORMATION: primer

<400> SEQUENCE: 28
acggttcctg gccttgatct actcgttact caaggc                           36

<210> SEQ ID NO 29
<211> LENGTH: 38
<212> TYPE: DNA
<213> ORGANISM: Artificial Sequence
<220> FEATURE:
<223> OTHER INFORMATION: primer

<400> SEQUENCE: 29
taggcacccc aggcttcgct atctactgta acatactc                         38

<210> SEQ ID NO 30
<211> LENGTH: 42
<212> TYPE: DNA
<213> ORGANISM: Artificial Sequence
<220> FEATURE:
<223> OTHER INFORMATION: primer

<400> SEQUENCE: 30
ggtaccggat cccctcgagt cgctatctac tgtaacatac tc                    42

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
ccaggtaccg atctactcgt tactcaaggc                                  30

<210> SEQ ID NO 32
<211> LENGTH: 31
<212> TYPE: DNA
<213> ORGANISM: Artificial Sequence
<220> FEATURE:
<223> OTHER INFORMATION: primer

<400> SEQUENCE: 32
cgaactcgag tagaaataca acagccaatt c                                31
```

```
<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33
gtagctcgca cggggtttg tcttg                                          25

<210> SEQ ID NO 34
<211> LENGTH: 28
<212> TYPE: DNA
<213> ORGANISM: Artificial Sequence
<220> FEATURE:
<223> OTHER INFORMATION: primer

<400> SEQUENCE: 34
gaactcatat gcacgggggc cacataac                                      28

<210> SEQ ID NO 35
<211> LENGTH: 28
<212> TYPE: DNA
<213> ORGANISM: Artificial Sequence
<220> FEATURE:
<223> OTHER INFORMATION: primer

<400> SEQUENCE: 35
taactcatat gcacgggggc cacataac                                      28

<210> SEQ ID NO 36
<211> LENGTH: 24
<212> TYPE: DNA
<213> ORGANISM: Artificial Sequence
<220> FEATURE:
<223> OTHER INFORMATION: primer

<400> SEQUENCE: 36
tagctcgcac ggggtttgt cttg                                           24

<210> SEQ ID NO 37
<211> LENGTH: 29
<212> TYPE: DNA
<213> ORGANISM: Artificial Sequence
<220> FEATURE:
<223> OTHER INFORMATION: primer

<400> SEQUENCE: 37
acaactcata tgcacggggg ccacataac                                     29

<210> SEQ ID NO 38
<211> LENGTH: 29
<212> TYPE: DNA
<213> ORGANISM: Artificial Sequence
<220> FEATURE:
<223> OTHER INFORMATION: primer

<400> SEQUENCE: 38
aaaactcata tgcacggggg ccacataac                                     29

<210> SEQ ID NO 39
<211> LENGTH: 27
<212> TYPE: DNA
<213> ORGANISM: Artificial Sequence
<220> FEATURE:
<223> OTHER INFORMATION: primer
```

```
<400> SEQUENCE: 39
aactcatatg cacgggggcc acataac                                          27

<210> SEQ ID NO 40
<211> LENGTH: 26
<212> TYPE: DNA
<213> ORGANISM: Artificial Sequence
<220> FEATURE:
<223> OTHER INFORMATION: primer

<400> SEQUENCE: 40
actcatatgc acggggccca cataac                                           26

<210> SEQ ID NO 41
<211> LENGTH: 28
<212> TYPE: DNA
<213> ORGANISM: Artificial Sequence
<220> FEATURE:
<223> OTHER INFORMATION: primer

<400> SEQUENCE: 41
aaactcatat gcacggggggc cacataac                                        28

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
ctcactggcc gtcgttttac                                                  20

<210> SEQ ID NO 43
<211> LENGTH: 26
<212> TYPE: DNA
<213> ORGANISM: Artificial Sequence
<220> FEATURE:
<223> OTHER INFORMATION: primer

<400> SEQUENCE: 43
gtgagtcgta ttaatttcga taagcc                                           26

<210> SEQ ID NO 44
<211> LENGTH: 40
<212> TYPE: DNA
<213> ORGANISM: Artificial Sequence
<220> FEATURE:
<223> OTHER INFORMATION: primer

<400> SEQUENCE: 44
attaatacga ctcactatag gagcgagcgg gagaccgctc                            40

<210> SEQ ID NO 45
<211> LENGTH: 38
<212> TYPE: DNA
<213> ORGANISM: Artificial Sequence
<220> FEATURE:
<223> OTHER INFORMATION: primer

<400> SEQUENCE: 45
aaggggttat gctaggctag caagggcgga gtgcaatg                              38

<210> SEQ ID NO 46
<211> LENGTH: 63
```

```
<212> TYPE: DNA
<213> ORGANISM: Artificial Sequence
<220> FEATURE:
<223> OTHER INFORMATION: primer

<400> SEQUENCE: 46
ctagcataac cccttggggc ctctaaacgg gtcttgaggg gttttttgct cactggccgt    60
cgt                                                                 63

<210> SEQ ID NO 47
<211> LENGTH: 63
<212> TYPE: DNA
<213> ORGANISM: Artificial Sequence
<220> FEATURE:
<223> OTHER INFORMATION: primer

<400> SEQUENCE: 47
acgacggcca gtgagcaaaa aaccccctcaa gacccgttta gaggcccccaa ggggttatgc    60 tag                                                                 63

<210> SEQ ID NO 48
<211> LENGTH: 24
<212> TYPE: DNA
<213> ORGANISM: Artificial Sequence
<220> FEATURE:
<223> OTHER INFORMATION: primer

<400> SEQUENCE: 48
atttcgataa gccaggttgc ttcc                                          24

<210> SEQ ID NO 49
<211> LENGTH: 36
<212> TYPE: DNA
<213> ORGANISM: Artificial Sequence
<220> FEATURE:
<223> OTHER INFORMATION: primer

<400> SEQUENCE: 49
ctggcttatc gaaattaggc accccaggct taatac                             36

<210> SEQ ID NO 50
<211> LENGTH: 37
<212> TYPE: DNA
<213> ORGANISM: Artificial Sequence
<220> FEATURE:
<223> OTHER INFORMATION: primer

<400> SEQUENCE: 50
acgacggcca gtgagacggt tcctggcctt taatacg                            37

<210> SEQ ID NO 51
<211> LENGTH: 744
<212> TYPE: DNA
<213> ORGANISM: Corynebacterium glutamicum

<400> SEQUENCE: 51
gtgagcagga aaagaatcg cctcaccggg gtagacgcac tcaatgaagc attcgatgca    60
gtagatcatc agccgctgct tgaccacctt ggtgtggaca tccagcgcga tctgttggtg   120
cttgcgttga ctcaccgctc tttcgccaac gaaaacggca tgctgcccaa taatgagcgc   180
ttggagttcc tcggcgacgc cgtcttgggt ctctccgtgg ccaacaagct ctatgagcag   240
taccccagca gccctgaatc tgatgtctcc aagatgcgcg cttcaattgt cagccgttac   300
```

```
ggcctggcag atatcgctcg cgaaattgat cttggcaacc acatattgct gggcaaaggc      360
gaattgctca ccgaaggtcg cagtaaggat tccattcttg cggacaccac agaggcgtta      420
ttcggcgcga ttttccgcca gcacggtttt gaaaccgccc gcgacgtaat tttgcgcctg      480
tttgcctaca agatcgataa cgcatcggcc aggggcattc accaggactg aagaccacg      540 ctgcaggagg aacttgccca cgcaagcgc cccatggctg aatattccgc cacctcagtc      600
ggtccggatc acgatctagt gttcaccgcc atcgtgacgc tggaaggtga agaaatgggt      660
cggggagaag gcccgaacaa gaagctggcc gagcaggaag cagcgcacca ggcattccga      720
aagcttcggg agtcccgtgc ctga                                             744
```

```
<210> SEQ ID NO 52
<211> LENGTH: 247
<212> TYPE: PRT
<213> ORGANISM: Corynebacterium glutamicum

<400> SEQUENCE: 52
```

Met Ser Arg Lys Lys Asn Arg Leu Thr Gly Val Asp Ala Leu Asn Glu
1               5                   10                  15

Ala Phe Asp Ala Val Asp His Gln Pro Leu Leu Asp His Leu Gly Val
                20                  25                  30

Asp Ile Gln Arg Asp Leu Leu Val Leu Ala Leu Thr His Arg Ser Phe
            35                  40                  45

Ala Asn Glu Asn Gly Met Leu Pro Asn Asn Glu Arg Leu Glu Phe Leu
        50                  55                  60

Gly Asp Ala Val Leu Gly Leu Ser Val Ala Asn Lys Leu Tyr Glu Gln
65                  70                  75                  80

Tyr Pro Ser Ser Pro Glu Ser Asp Val Ser Lys Met Arg Ala Ser Ile
                85                  90                  95

Val Ser Arg Tyr Gly Leu Ala Asp Ile Ala Arg Glu Ile Asp Leu Gly
                100                 105                 110

Asn His Ile Leu Leu Gly Lys Gly Glu Leu Leu Thr Glu Gly Arg Ser
            115                 120                 125

Lys Asp Ser Ile Leu Ala Asp Thr Thr Glu Ala Leu Phe Gly Ala Ile
        130                 135                 140

Phe Arg Gln His Gly Phe Glu Thr Ala Arg Asp Val Ile Leu Arg Leu
145                 150                 155                 160

Phe Ala Tyr Lys Ile Asp Asn Ala Ser Ala Arg Gly Ile His Gln Asp
                165                 170                 175

Trp Lys Thr Thr Leu Gln Glu Glu Leu Ala Gln Arg Lys Arg Pro Met
            180                 185                 190

Ala Glu Tyr Ser Ala Thr Ser Val Gly Pro Asp His Asp Leu Val Phe
        195                 200                 205

Thr Ala Ile Val Thr Leu Glu Gly Glu Glu Met Gly Arg Gly Glu Gly
    210                 215                 220

Pro Asn Lys Lys Leu Ala Glu Gln Glu Ala Ala His Gln Ala Phe Arg
225                 230                 235                 240

Lys Leu Arg Glu Ser Arg Ala
                245

```
<210> SEQ ID NO 53
<211> LENGTH: 405
<212> TYPE: DNA
<213> ORGANISM: Potato spindle tuber viroid

<400> SEQUENCE: 53
```

```
tctagacgga actaaactcg tggttcctgt ggttcacacc tgacctcctg agcagaaaag    60 aaaaagaag gcggctcgga ggagcgcttc agggattccc ggggaaacct ggagcgaact    120
ggcaacaagg acggtgggga gtgcccagcg gccgacagga gtaattcccg ccgaaacagg    180
gttttcaccc ttcctttctt cgggtgtcct tcctcgcgcc cgcaggacca cccctcgccc    240
cctttgcgct gtcgcttcgg ctactacccg gtggaaacaa ctgaagctcc cgagaaccgc    300 ttttctcta tcttacttgc ttcggggcga gggtgtttag cccttggaac cgcagttggt    360
tcctggatcc ggggaattgt tatttgttta aattttccc tcgag                    405
```

<210> SEQ ID NO 54
<211> LENGTH: 45
<212> TYPE: DNA
<213> ORGANISM: Artificial Sequence
<220> FEATURE:
<223> OTHER INFORMATION: primer

<400> SEQUENCE: 54

```
caacatggta cctctggaac gtacatgcca ccgctgagca ataac                   45
```

<210> SEQ ID NO 55
<211> LENGTH: 37
<212> TYPE: DNA
<213> ORGANISM: Artificial Sequence
<220> FEATURE:
<223> OTHER INFORMATION: primer

<400> SEQUENCE: 55

```
ctgcaggtcg accaatccgg atatagttcc tcctttc                            37
```

<210> SEQ ID NO 56
<211> LENGTH: 33
<212> TYPE: DNA
<213> ORGANISM: Artificial Sequence
<220> FEATURE:
<223> OTHER INFORMATION: primer

<400> SEQUENCE: 56

```
gaatatggta ccggagctga ctgggttgaa ggc                                33
```

<210> SEQ ID NO 57
<211> LENGTH: 36
<212> TYPE: DNA
<213> ORGANISM: Artificial Sequence
<220> FEATURE:
<223> OTHER INFORMATION: primer

<400> SEQUENCE: 57

```
ctacatggta ccaatccgga tatagttcct cctttc                             36
```

<210> SEQ ID NO 58
<211> LENGTH: 1464
<212> TYPE: DNA
<213> ORGANISM: Artificial Sequence
<220> FEATURE:
<223> OTHER INFORMATION: DNA fragment

<400> SEQUENCE: 58

```
gggggtagtt ttattccccc tagtggtttt tcagtacgac aatcgagaaa gacctgtttc    60
agccagttcg ggtcatgttc gtcggtatgg ccacgtgcat agcgaccagt tttcgagttc   120
actgggattt ttggtgcatc gaacaagatg taggacaatg cggtttctag gtctactttt   180
```

| | |
|---|---|
| tgctttatgc cgtacaagcc ccgtgggtat tcagcgattg attccaaggc ggcttcccag | 240 |
| tcctgttttg tgaaggactg gcttagttct aggtctgtgt ctgggtagta ctgcttgttt | 300 |
| gtgtaagcgc cgttggtgct cattgatgat tcctttgaag tgtttggagt tcggctagta | 360 |
| gtgcggcgta tggtgctgct ttttgctcgt gatagctcgc cttggctatg aggtcggcta | 420 |
| ggtaggtttc cggggtgcct aggttgcgta ggtctagcaa atcccggtat gtggcctgtg | 480 |
| cgctgcgctg gtggtgcata cagtcgttaa gctgggcttt tacgtctgcg atgcggtggc | 540 |
| ggttaggcat gttggtgtgc ttcttccaag tactcacggg cgggttttgt gtatgcctgg | 600 |
| cgtgatgctt ctttgagctg ttggagttcc gcttggagtg cgggtagttc gtccgcgaac | 660 |
| tgcttgtggt actcgtattt ctcttgttcc tgggcgatca gatttgcgtt gaattgcagg | 720 |
| gcggtgagtt cgtccacgcg tcgttttgct gcgttggtca tggtggcgtg ccatttgcgg | 780 |
| ttgtggacgc ggggttcaag gttgcgcacg gctgcttcgg ctaggttggt ggctgctttt | 840 |
| ttcagtgctc gggcttcccg ttcctcgtcc aacgagagca cctttggttt gttggcttcg | 900 |
| gctagttttt gcttctccgc tttgatgagt tggtcaactt cgtgttggga gaggtcgttt | 960 |
| ttcacgatgc gtcgaatgtg gtcgttgtgg gtgctgagtt ggtgtgagag gtagtggggt | 1020 |
| tctgggattt cggcgagttg gtcgaggttg gtgtagtgcg ggttgcggcc tggttggttg | 1080 |
| ggttcgctgg ggaggtcgat gtatccggtt gagtctccgg cgtggttgaa gtgaattagg | 1140 |
| cgttggtagc cgtattcctg gttggggagg tacgacagaa tgaggaagtt tggtgcttct | 1200 |
| cctgcaatga gtcgtgcgtg ttcgtagttc ggtactgggt cgtgctcggg gagaatgttc | 1260 |
| ttttgggtca tggcttctct ttctgttgct ctgtaagtcc gtatgtgggc atgggaaagc | 1320 |
| cccggcaacc ctttgggtca accggggcta gatagtcgct tagaatggct tctaggctgc | 1380 |
| gtctcggggt gtggcaagct gtaagaggtt ccaactttca ccataatgaa ataagatcac | 1440 |
| taccgggcgt attttttgag ttat | 1464 |

<210> SEQ ID NO 59
<211> LENGTH: 161
<212> TYPE: DNA
<213> ORGANISM: Artificial Sequence
<220> FEATURE:
<223> OTHER INFORMATION: DNA fragment

<400> SEQUENCE: 59

| | |
|---|---|
| ggtgcctatg aagctgggta tgaagatggg ttaagaacag attgaaatat taacaacatg | 60 |
| tagtgtaatg tcttagttgt gcctttgtga gatggggcca atgggataag cgcccccggt | 120 |
| tgtgtagtat aagaaccatg agttcctaca tcaccggggc | 161 |

<210> SEQ ID NO 60
<211> LENGTH: 40
<212> TYPE: DNA
<213> ORGANISM: Artificial Sequence
<220> FEATURE:
<223> OTHER INFORMATION: primer

<400> SEQUENCE: 60

| | |
|---|---|
| gagttcctac atcaccgggg cccgagattt tcaggagcta | 40 |

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
cgccttgcgt ataatatttg                                               20

<210> SEQ ID NO 62
<211> LENGTH: 32
<212> TYPE: DNA
<213> ORGANISM: Artificial Sequence
<220> FEATURE:
<223> OTHER INFORMATION: primer

<400> SEQUENCE: 62
tctgtcgtta acggtgccta tgaagctggg ta                                 32

<210> SEQ ID NO 63
<211> LENGTH: 35
<212> TYPE: DNA
<213> ORGANISM: Artificial Sequence
<220> FEATURE:
<223> OTHER INFORMATION: primer

<400> SEQUENCE: 63
caagtaagat ctatgcgacg gtgtagattt cctcg                              35

<210> SEQ ID NO 64
<211> LENGTH: 37
<212> TYPE: DNA
<213> ORGANISM: Artificial Sequence
<220> FEATURE:
<223> OTHER INFORMATION: primer

<400> SEQUENCE: 64
ctagtaagat ctcgattttc ctaatcacct tgcaggt                            37

<210> SEQ ID NO 65
<211> LENGTH: 42
<212> TYPE: DNA
<213> ORGANISM: Artificial Sequence
<220> FEATURE:
<223> OTHER INFORMATION: primer

<400> SEQUENCE: 65
agtgtggcta gcttagatct gctgtgcttt cagtggattt cg                      42

<210> SEQ ID NO 66
<211> LENGTH: 41
<212> TYPE: DNA
<213> ORGANISM: Artificial Sequence
<220> FEATURE:
<223> OTHER INFORMATION: primer

<400> SEQUENCE: 66
tgaacagcta gcaaagatct cccgatggta gtgtggggtc t                       41

<210> SEQ ID NO 67
<211> LENGTH: 37
<212> TYPE: DNA
<213> ORGANISM: Artificial Sequence
<220> FEATURE:
<223> OTHER INFORMATION: primer

<400> SEQUENCE: 67
tatgaccatg attaccccga tggtagtgtg gggtctc                            37

<210> SEQ ID NO 68

```
<211> LENGTH: 37
<212> TYPE: DNA
<213> ORGANISM: Artificial Sequence
<220> FEATURE:
<223> OTHER INFORMATION: primer

<400> SEQUENCE: 68
tctagaggat ccccggctgt gctttcagtg gatttcg                              37

<210> SEQ ID NO 69
<211> LENGTH: 21
<212> TYPE: DNA
<213> ORGANISM: Artificial Sequence
<220> FEATURE:
<223> OTHER INFORMATION: primer

<400> SEQUENCE: 69
cggggatcct ctagagtcga c                                              21

<210> SEQ ID NO 70
<211> LENGTH: 24
<212> TYPE: DNA
<213> ORGANISM: Artificial Sequence
<220> FEATURE:
<223> OTHER INFORMATION: primer

<400> SEQUENCE: 70
gtaatcatgg tcatagctgt ttcc                                           24

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
agcctggggt gcctaatgag                                                20

<210> SEQ ID NO 72
<211> LENGTH: 21
<212> TYPE: DNA
<213> ORGANISM: Artificial Sequence
<220> FEATURE:
<223> OTHER INFORMATION: primer

<400> SEQUENCE: 72
aaggccagga accgtaaaaa g                                              21

<210> SEQ ID NO 73
<211> LENGTH: 87
<212> TYPE: DNA
<213> ORGANISM: Artificial Sequence
<220> FEATURE:
<223> OTHER INFORMATION: DNA fragment

<400> SEQUENCE: 73
taggcacccc aggcttaata cgactcacta gggggtacc ggatcccctc gagcctatag     60
tgagtcgtat taaaggccag gaaccgt                                        87

<210> SEQ ID NO 74
<211> LENGTH: 87
<212> TYPE: DNA
<213> ORGANISM: Artificial Sequence
<220> FEATURE:
<223> OTHER INFORMATION: DNA fragment
```

```
<400> SEQUENCE: 74
acggttcctg gcctttaata cgactcacta taggctcgag gggatccggt accccriginaltatag      60 tgagtcgtat taagcctggg gtgccta                                                 87

<210> SEQ ID NO 75
<211> LENGTH: 346
<212> TYPE: DNA
<213> ORGANISM: Artificial Sequence
<220> FEATURE:
<223> OTHER INFORMATION: DNA fragment

<400> SEQUENCE: 75
cctcggaatc ggcgaccaga cgttgtgctt ctactgcggc ggcggtctga aagattgggt      60
cgaagaagac gatccgtggg aacagcacgc gctttggttc ccccagtgta attatctatt     120
attgaagaaa acacccgctt tcgtcaaaga cgtccaagaa aaacataaag gcgatttgtc     180
gtcatccaag caaaacgaga ccgaagtggt agcaagtagt agcagtagtc acaactccaa     240
agaatctcca agtgcggtgg tagaagagcg agaaagaaac aacgcagagg aaagctcgac     300
attatgcaaa atatgttata aaaatgaatt ggctgttgta tttcta                   346

<210> SEQ ID NO 76
<211> LENGTH: 28
<212> TYPE: DNA
<213> ORGANISM: Artificial Sequence
<220> FEATURE:
<223> OTHER INFORMATION: primer

<400> SEQUENCE: 76
cttggtaccc ctcggaatcg gcgaccag                                        28

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
gttctcgagt agaaatacaa cagccaattc                                      30

<210> SEQ ID NO 78
<211> LENGTH: 18
<212> TYPE: DNA
<213> ORGANISM: Bacteriophage T7

<400> SEQUENCE: 78
taatacgact cactatag                                                   18

<210> SEQ ID NO 79
<211> LENGTH: 25
<212> TYPE: DNA
<213> ORGANISM: Artificial Sequence
<220> FEATURE:
<223> OTHER INFORMATION: primer

<400> SEQUENCE: 79
aaaatcgctt gaccattgca ggttg                                           25

<210> SEQ ID NO 80
<211> LENGTH: 27
<212> TYPE: DNA
```

```
<213> ORGANISM: Artificial Sequence
<220> FEATURE:
<223> OTHER INFORMATION: primer

<400> SEQUENCE: 80
ctttagcttt cctagcttgt cgttgac                                              27

<210> SEQ ID NO 81
<211> LENGTH: 26
<212> TYPE: DNA
<213> ORGANISM: Artificial Sequence
<220> FEATURE:
<223> OTHER INFORMATION: primer

<400> SEQUENCE: 81
gcaaatcgct tgaccattgc aggttg                                               26

<210> SEQ ID NO 82
<211> LENGTH: 26
<212> TYPE: DNA
<213> ORGANISM: Artificial Sequence
<220> FEATURE:
<223> OTHER INFORMATION: primer

<400> SEQUENCE: 82
tttagctttc ctagcttgtc gttgac                                               26

<210> SEQ ID NO 83
<211> LENGTH: 26
<212> TYPE: DNA
<213> ORGANISM: Artificial Sequence
<220> FEATURE:
<223> OTHER INFORMATION: primer

<400> SEQUENCE: 83
aaaaatcgct tgaccattgc aggttg                                               26

<210> SEQ ID NO 84
<211> LENGTH: 26
<212> TYPE: DNA
<213> ORGANISM: Artificial Sequence
<220> FEATURE:
<223> OTHER INFORMATION: primer

<400> SEQUENCE: 84
gacaatcgct tgaccattgc aggttg                                               26

<210> SEQ ID NO 85
<211> LENGTH: 26
<212> TYPE: DNA
<213> ORGANISM: Artificial Sequence
<220> FEATURE:
<223> OTHER INFORMATION: primer

<400> SEQUENCE: 85
ccaaatcgct tgaccattgc aggttg                                               26

<210> SEQ ID NO 86
<211> LENGTH: 26
<212> TYPE: DNA
<213> ORGANISM: Artificial Sequence
<220> FEATURE:
<223> OTHER INFORMATION: primer

<400> SEQUENCE: 86
caaaatcgct tgaccattgc aggttg                                               26
```

```
<210> SEQ ID NO 87
<211> LENGTH: 24
<212> TYPE: DNA
<213> ORGANISM: Artificial Sequence
<220> FEATURE:
<223> OTHER INFORMATION: primer

<400> SEQUENCE: 87
gatctactcg ttactcaagg caag                                              24

<210> SEQ ID NO 88
<211> LENGTH: 28
<212> TYPE: DNA
<213> ORGANISM: Artificial Sequence
<220> FEATURE:
<223> OTHER INFORMATION: primer

<400> SEQUENCE: 88
gatccccgta aaataacgc cccacctc                                           28

<210> SEQ ID NO 89
<211> LENGTH: 28
<212> TYPE: DNA
<213> ORGANISM: Artificial Sequence
<220> FEATURE:
<223> OTHER INFORMATION: primer

<400> SEQUENCE: 89
atttttacgg ggatcctcta gagtcgac                                          28

<210> SEQ ID NO 90
<211> LENGTH: 36
<212> TYPE: DNA
<213> ORGANISM: Artificial Sequence
<220> FEATURE:
<223> OTHER INFORMATION: primer

<400> SEQUENCE: 90
agtaacgagt agatcgcctg gggtgcctaa tgagtg                                 36
```